(12) United States Patent
Kirschenman

(10) Patent No.: US 8,317,744 B2
(45) Date of Patent: Nov. 27, 2012

(54) ROBOTIC CATHETER MANIPULATOR ASSEMBLY

(75) Inventor: Mark B. Kirschenman, Waverly, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 908 days.

(21) Appl. No.: 12/347,826

(22) Filed: Dec. 31, 2008

(65) Prior Publication Data

US 2009/0247942 A1 Oct. 1, 2009

Related U.S. Application Data

(60) Provisional application No. 61/040,143, filed on Mar. 27, 2008, provisional application No. 61/099,904, filed on Sep. 24, 2008.

(51) Int. Cl.
*A61M 37/00* (2006.01)
(52) U.S. Cl. ................................... 604/95.04
(58) Field of Classification Search ............... 604/95.04, 604/95.05, 22; 606/41, 130; 600/141, 145; 424/422; 318/568.11; 607/122
See application file for complete search history.

(56) References Cited

U.S. PATENT DOCUMENTS

| | | |
|---|---|---|
| 4,802,487 A | 2/1989 | Martin et al. |
| 4,884,557 A | 12/1989 | Takehana et al. |
| 5,170,817 A | 12/1992 | Sunderland et al. |
| 5,318,525 A | 6/1994 | West et al. |
| 5,441,483 A | 8/1995 | Avitall |
| 5,545,200 A | 8/1996 | West et al. |
| 5,579,442 A | 11/1996 | Kimoto et al. |
| 5,630,783 A | 5/1997 | Steinberg |
| 5,706,827 A | 1/1998 | Ehr et al. |
| 5,791,908 A | 8/1998 | Gillio |
| 5,807,377 A | 9/1998 | Madhani et al. |
| 5,808,665 A | 9/1998 | Green |
| 6,040,758 A | 3/2000 | Sedor et al. |
| 6,063,095 A | 5/2000 | Wang et al. |
| 6,348,911 B1 | 2/2002 | Rosenberg et al. |
| 6,396,232 B2 | 5/2002 | Haanpaa et al. |

(Continued)

FOREIGN PATENT DOCUMENTS

WO WO-2008/101228 8/2008

(Continued)

OTHER PUBLICATIONS

"International Search Report & Written Opinion", PCT/US2009/069712 Feb. 25, 2010.

(Continued)

*Primary Examiner* — Nicholas Lucchesi
*Assistant Examiner* — Brooke Matney
(74) *Attorney, Agent, or Firm* — Dykema Gossett PLLC

(57) ABSTRACT

A robotic catheter manipulator assembly may include a support member including a catheter manipulation base and a sheath manipulation base movable relative to each other and to the support member. Each respective manipulation base may be releasably connectable to a catheter cartridge and a sheath cartridge. A drive mechanism may be provided for moving the catheter and sheath manipulation bases relative to each other and to the support member. The manipulation base or the cartridge may include a first element engageable with a complementary second element slidably engaged with the other one of the manipulation base or the cartridge for controlling movement of a component connected to the cartridge. The cartridge, for example, may be a transseptal cartridge, a catheter cartridge or a sheath cartridge, and the component may respectively be a surgically insertable device such as a transseptal needle, a catheter or a sheath.

46 Claims, 49 Drawing Sheets

U.S. PATENT DOCUMENTS

| | | |
|---|---|---|
| 6,500,167 B1 | 12/2002 | Webster |
| 6,709,667 B1 | 3/2004 | Lowe et al. |
| 6,850,252 B1 | 2/2005 | Hoffberg |
| 6,869,390 B2 | 3/2005 | Elliott et al. |
| 6,869,396 B2 | 3/2005 | Belson |
| 7,199,790 B2 | 4/2007 | Rosenberg et al. |
| 7,276,044 B2 | 10/2007 | Ferry et al. |
| 2002/0068868 A1 | 6/2002 | Thompson et al. |
| 2002/0072704 A1 | 6/2002 | Mansouri-Ruiz |
| 2002/0087048 A1 | 7/2002 | Brock et al. |
| 2004/0193239 A1 | 9/2004 | Falwell et al. |
| 2005/0075538 A1 | 4/2005 | Banik et al. |
| 2005/0203382 A1 | 9/2005 | Govari et al. |
| 2006/0089637 A1 | 4/2006 | Werneth et al. |
| 2006/0155321 A1 | 7/2006 | Bressler et al. |
| 2006/0276775 A1 | 12/2006 | Rosenberg et al. |
| 2006/0293643 A1 | 12/2006 | Wallace et al. |
| 2007/0043338 A1 | 2/2007 | Moll et al. |
| 2007/0142726 A1 | 6/2007 | Carney et al. |
| 2007/0185486 A1 | 8/2007 | Hauck et al. |
| 2007/0197896 A1 | 8/2007 | Moll et al. |
| 2007/0197939 A1 | 8/2007 | Wallace et al. |
| 2007/0198008 A1 | 8/2007 | Hauck et al. |
| 2007/0233044 A1 | 10/2007 | Wallace et al. |
| 2007/0270685 A1 | 11/2007 | Kang et al. |
| 2007/0298877 A1 | 12/2007 | Rosenberg et al. |
| 2008/0009791 A1 | 1/2008 | Cohen et al. |
| 2008/0013809 A1 | 1/2008 | Zhu et al. |
| 2008/0312536 A1 | 12/2008 | Dala-Krishna |
| 2009/0033623 A1 | 2/2009 | Lin |
| 2009/0247993 A1 | 10/2009 | Kirschenman et al. |
| 2009/0322697 A1 | 12/2009 | Cao |

FOREIGN PATENT DOCUMENTS

| | | |
|---|---|---|
| WO | WO-2009/120992 | 10/2009 |

OTHER PUBLICATIONS

Massey, Joe B. et al., "Medical device introduction systems and methods", WO 2007-146325 A2 Dec. 21, 2007.

Morales, Ruiz, "Robotic surgical system for performing minimally invasive medical procedures", WO 2007-088208 Aug. 9, 2007.

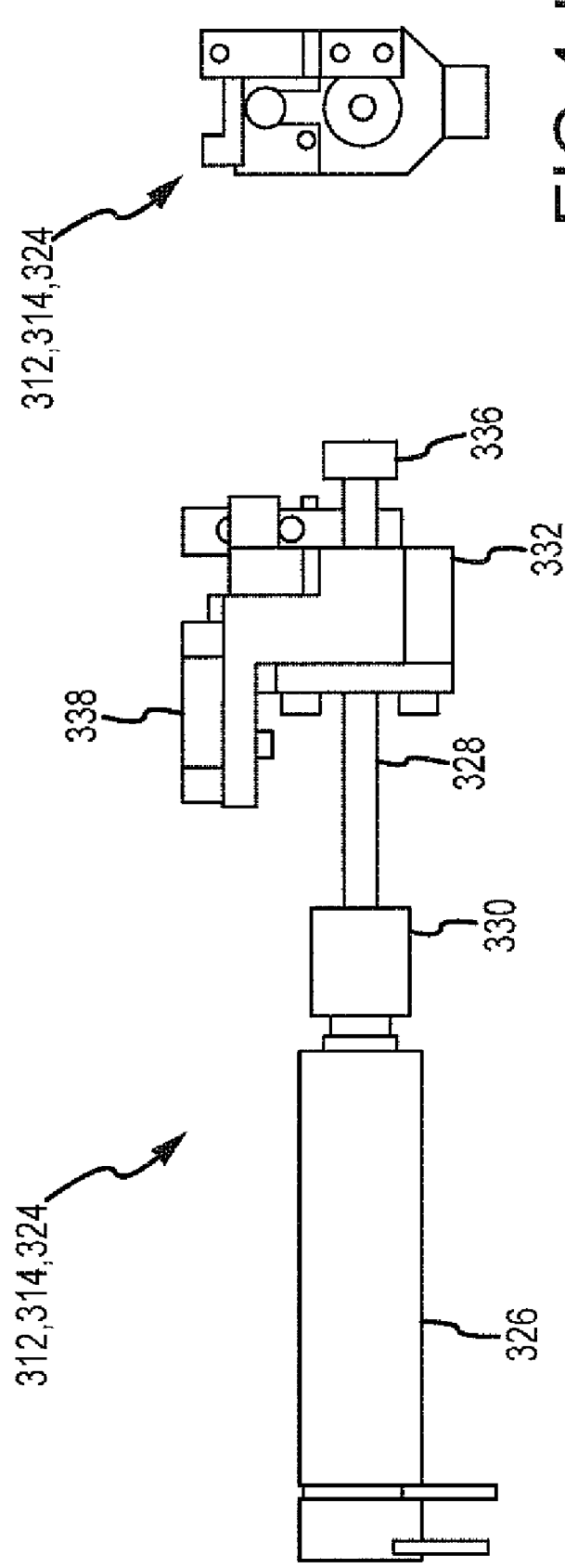

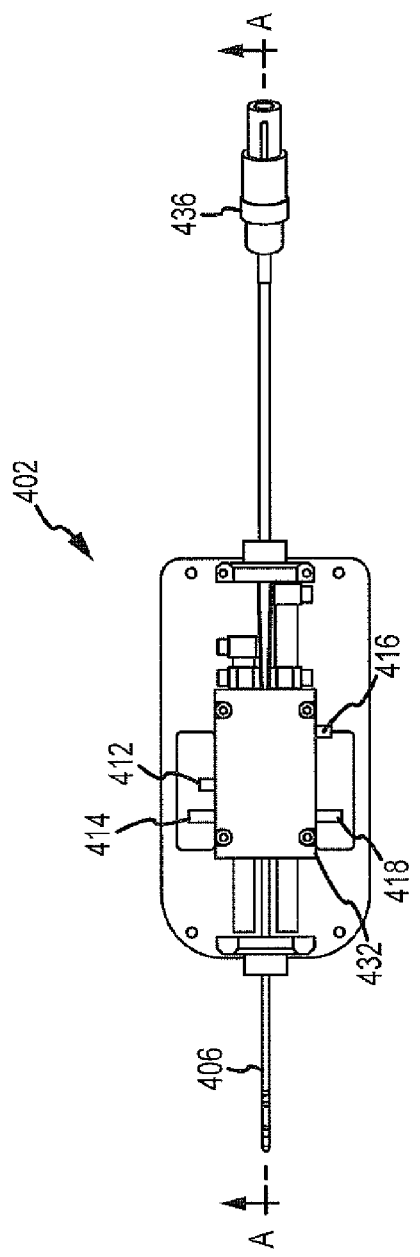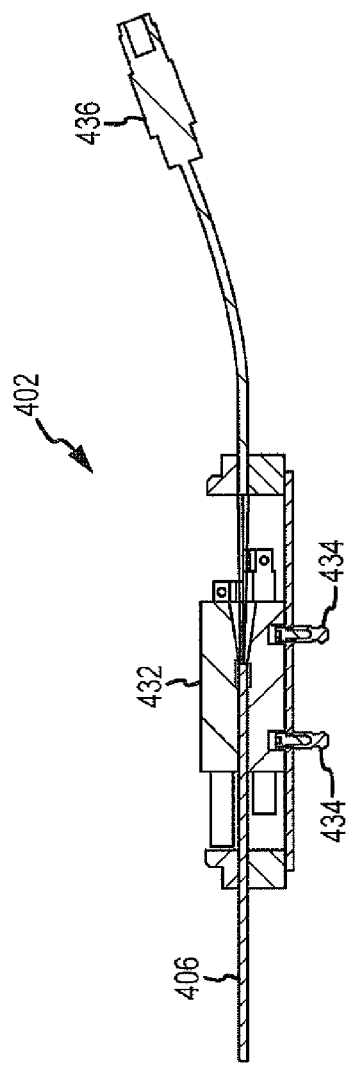

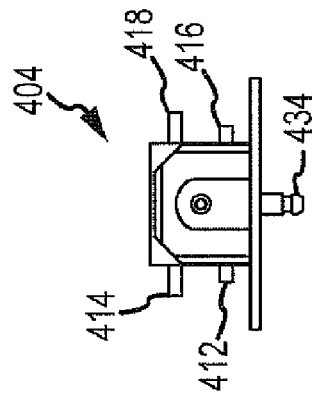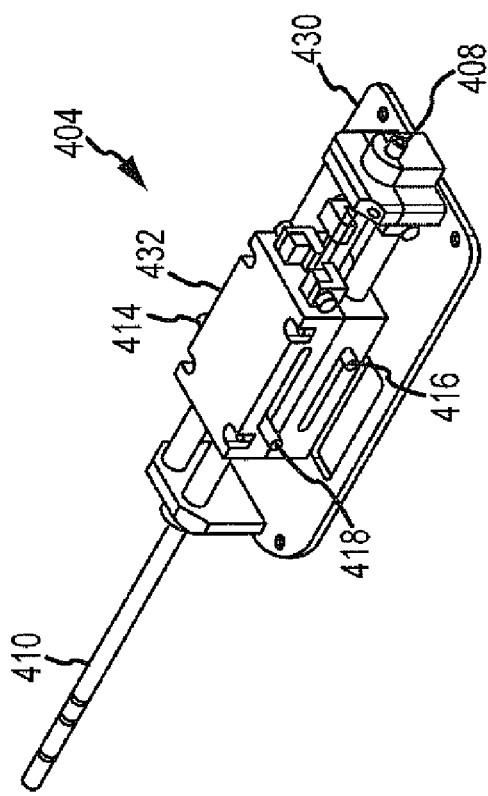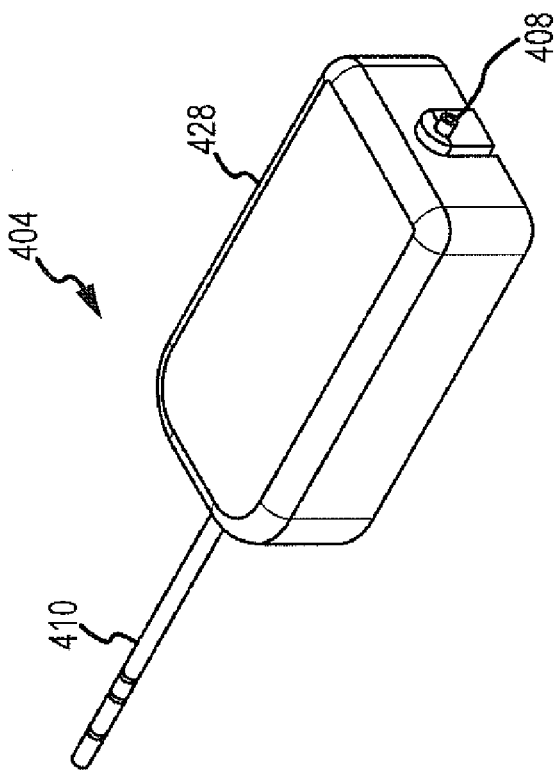

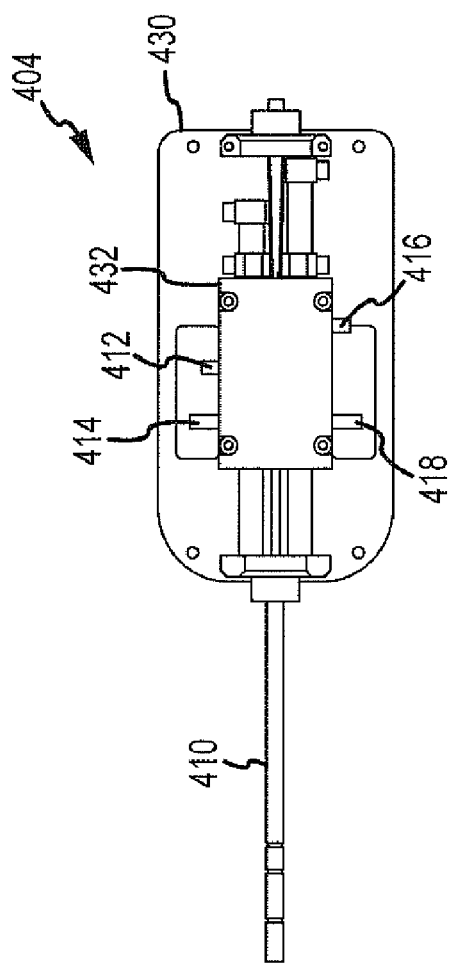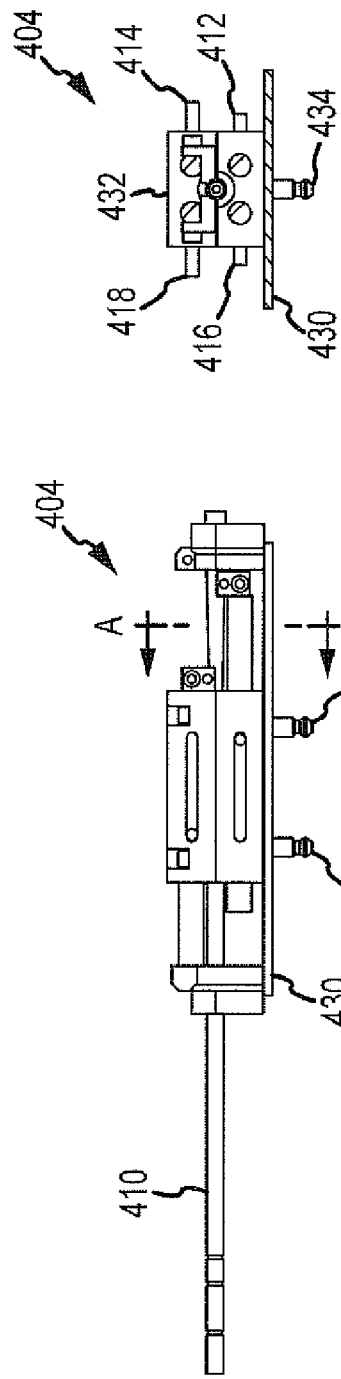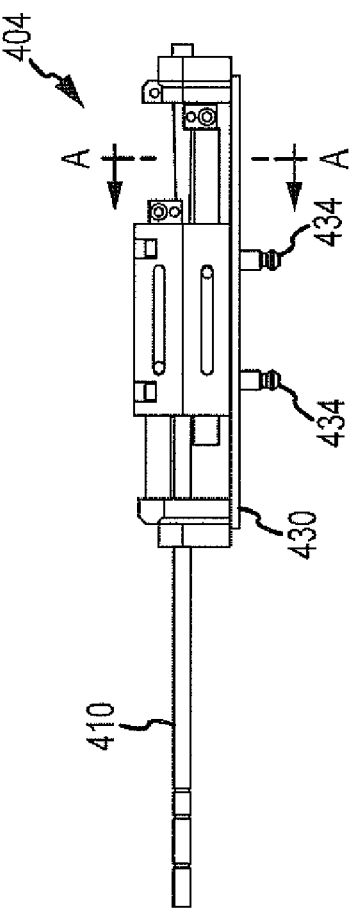

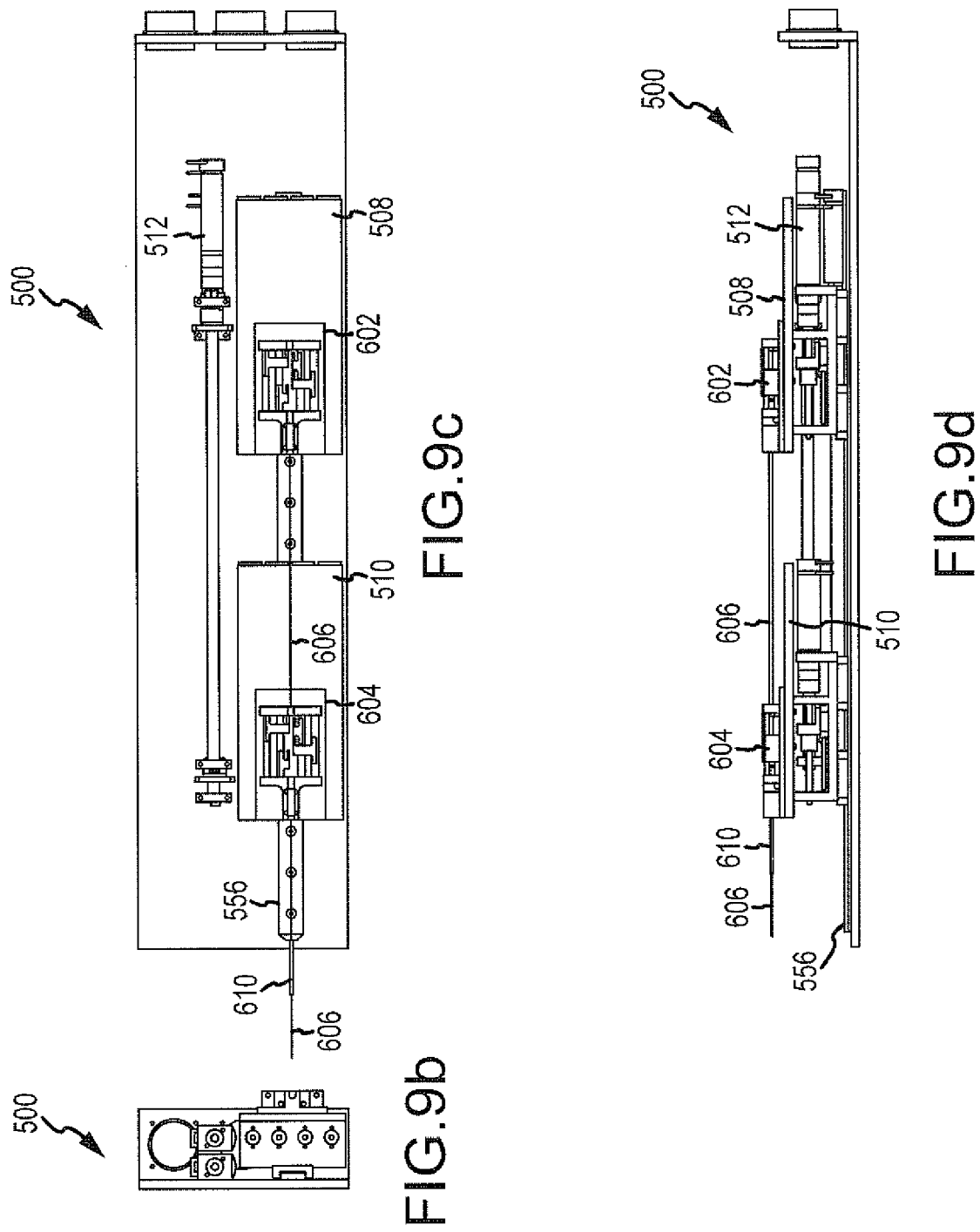

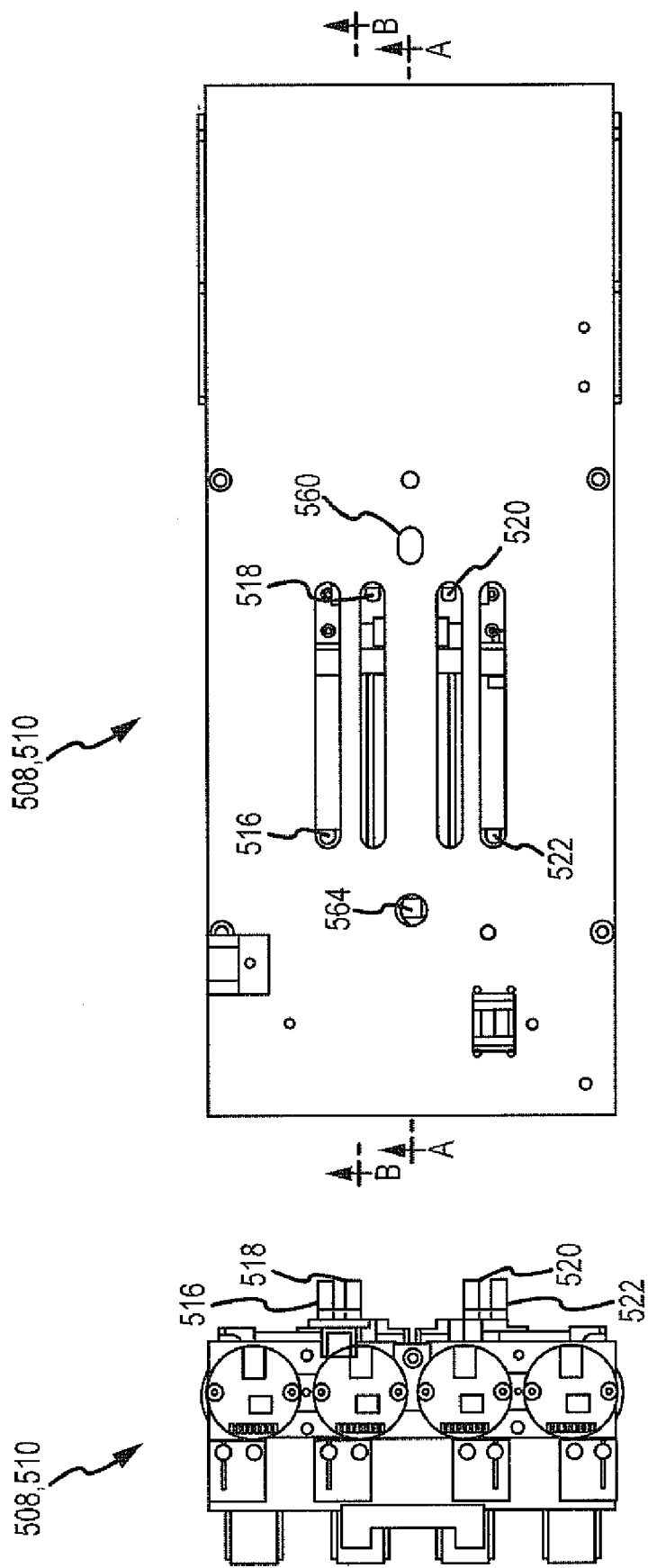

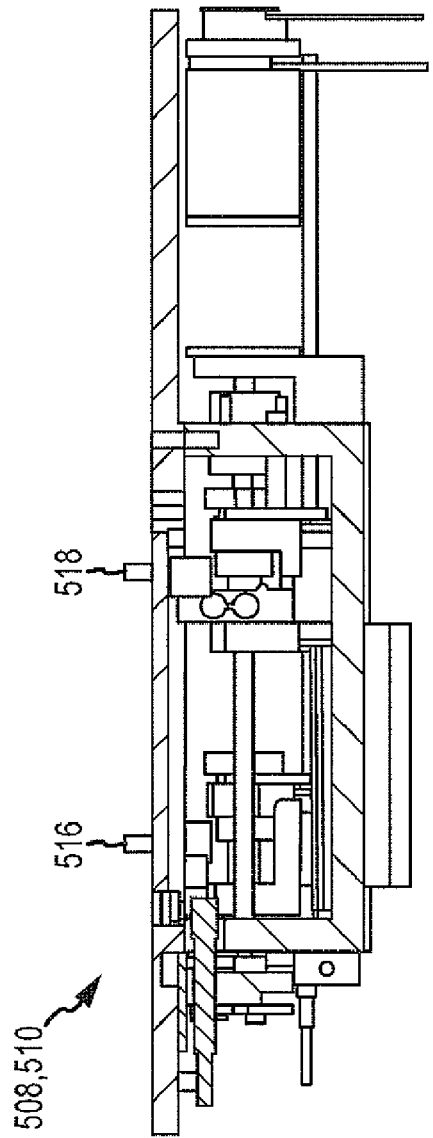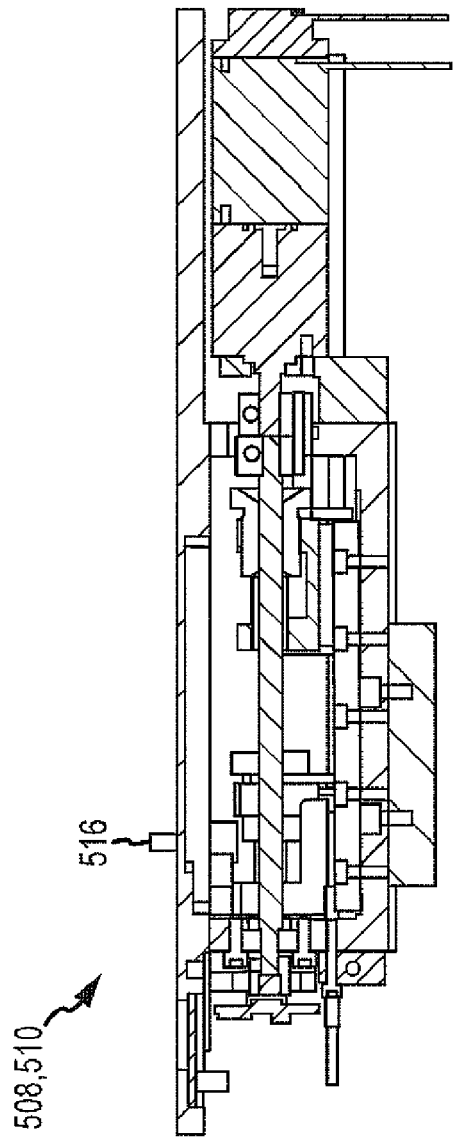

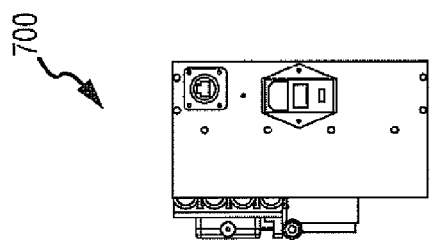
FIG.12e
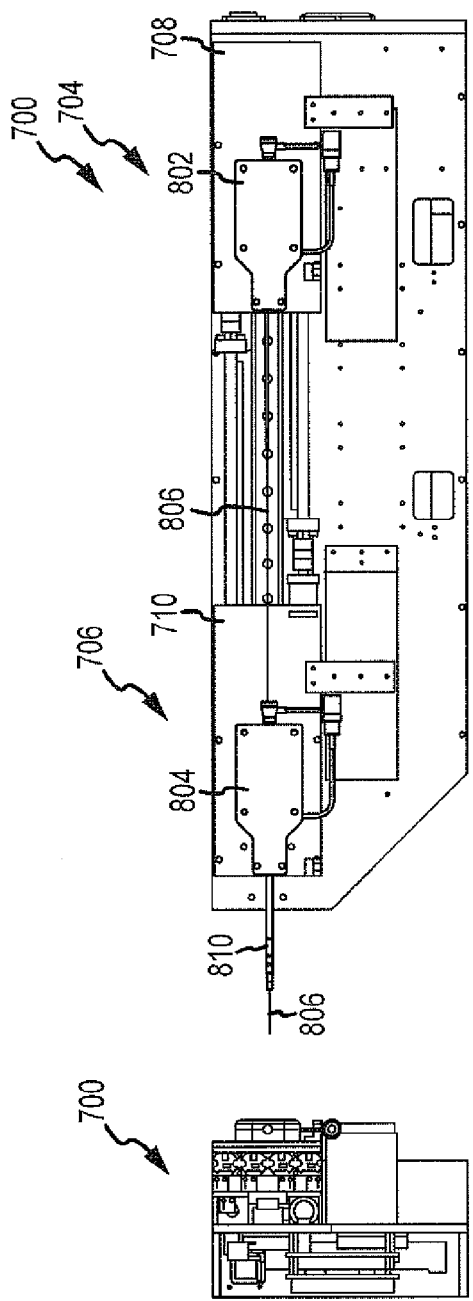
FIG.12f
FIG.12d
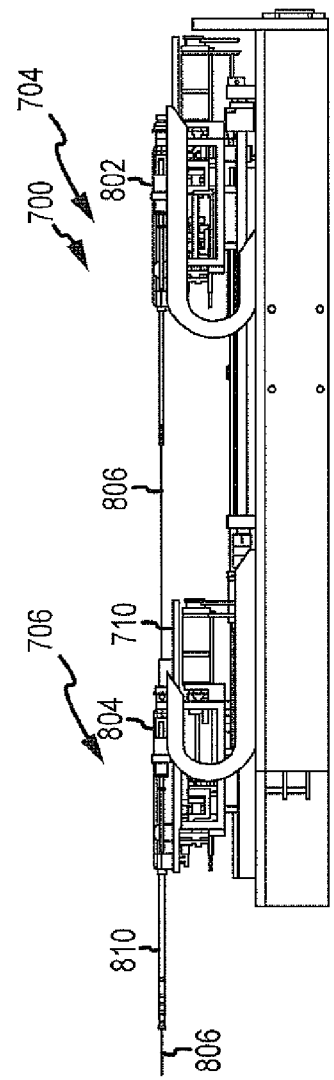
FIG.12g

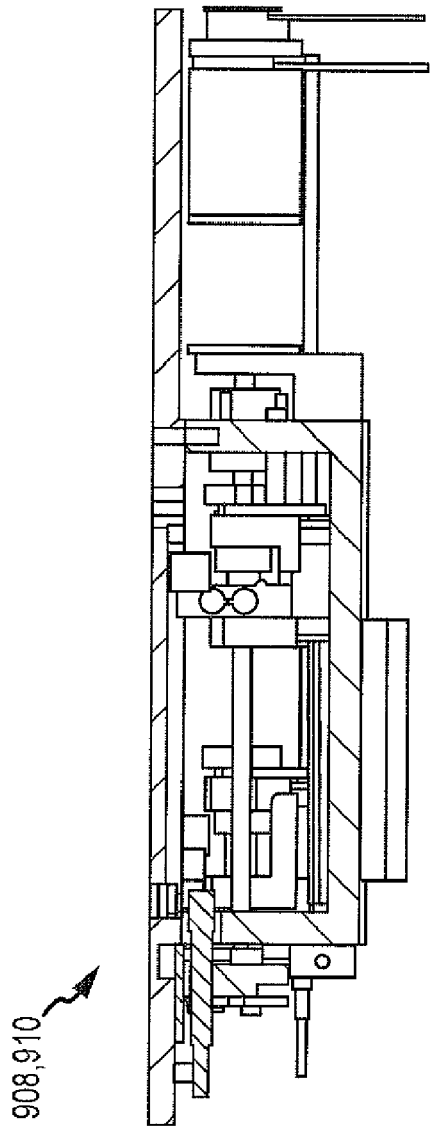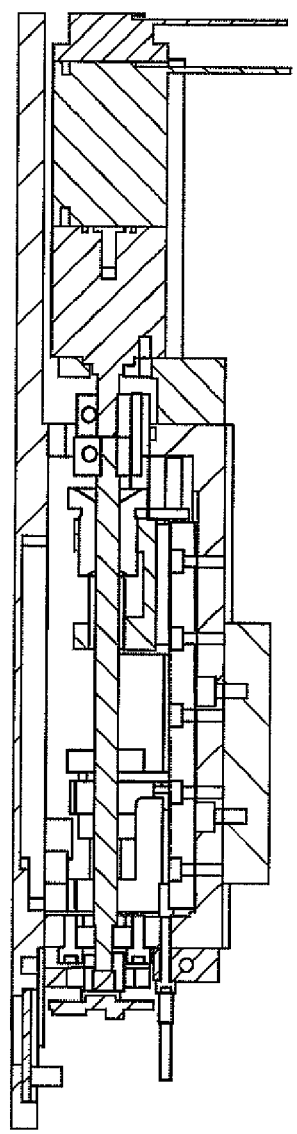

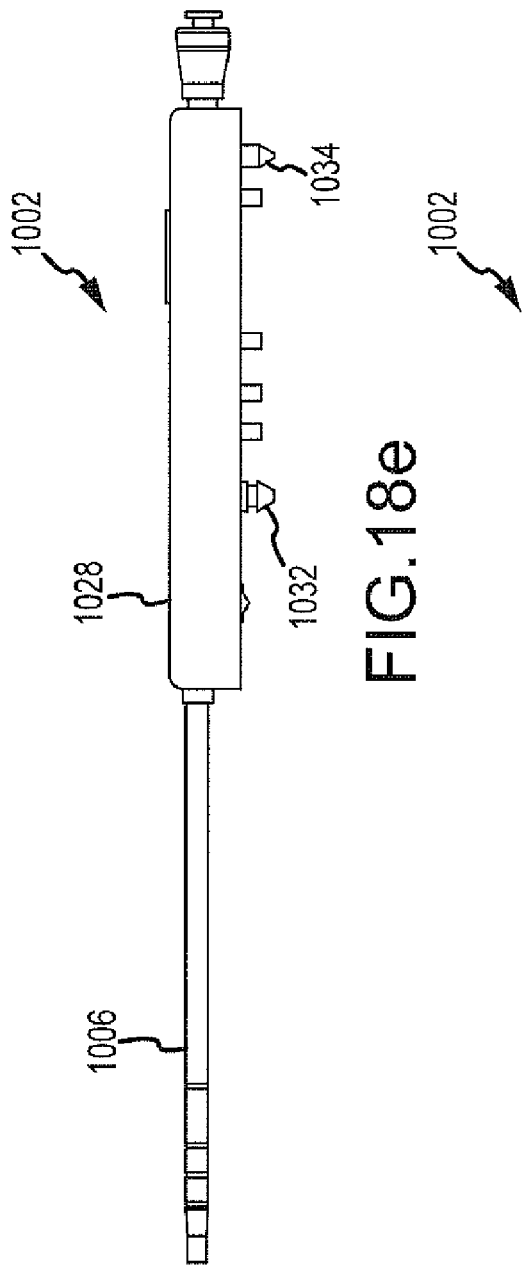
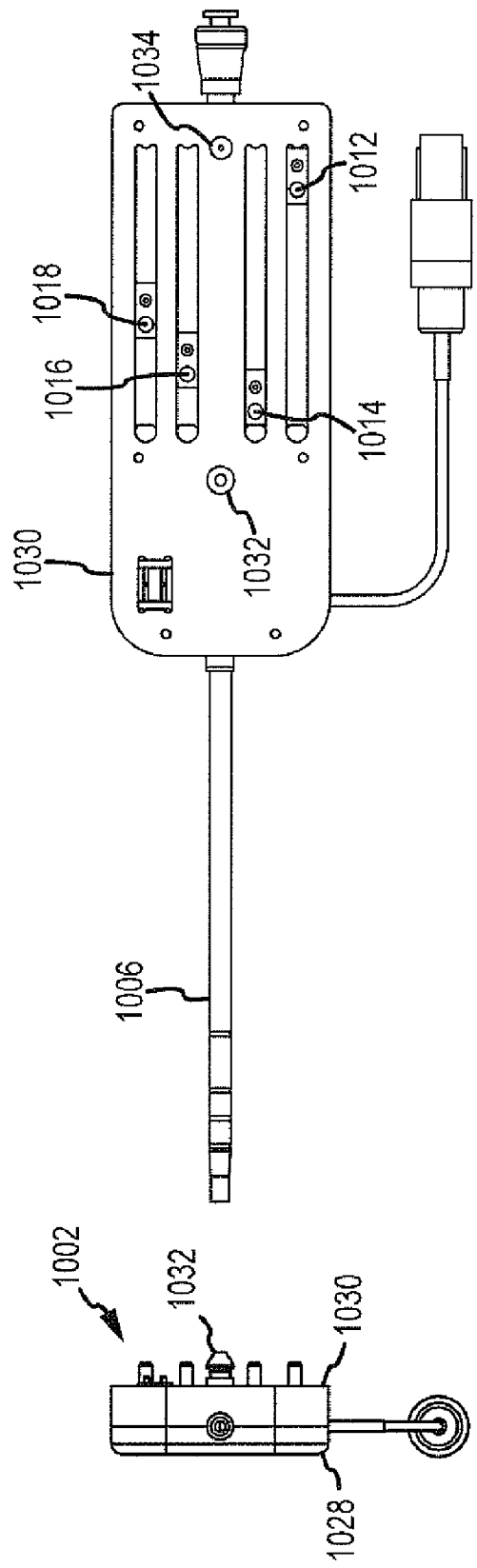
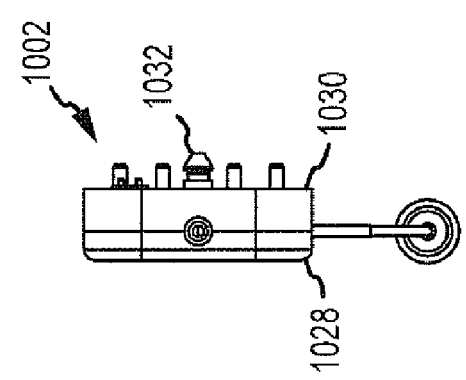
FIG.18e
FIG.18d
FIG.18c

ROBOTIC CATHETER MANIPULATOR ASSEMBLY

CROSS REFERENCE TO RELATED APPLICATIONS

This application claims the benefit of priority to U.S. Provisional Application Nos. 61/040,143, filed Mar. 27, 2008 and 61/099,904, filed Sep. 24, 2008, the entire disclosures of which are incorporated herein by reference.

BACKGROUND OF THE INVENTION a. Field of the Invention

This invention relates to a robotic catheter system and method for automated control of a catheter and related components. In particular, the instant invention relates to a robotic manipulator assembly usable with a robotic catheter system for manipulating a catheter and related components, for example, for diagnostic, therapeutic, mapping, ablative, lead placement, valve repair and other procedures.

b. Background Art

Electrophysiology catheters are used in a variety of diagnostic and/or therapeutic medical procedures to correct conditions such as atrial arrhythmia, including for example, ectopic atrial tachycardia, atrial fibrillation, and atrial flutter. Arrhythmia can create a variety of dangerous conditions including irregular heart rates, loss of synchronous atrioventricular contractions and stasis of blood flow which can lead to a variety of ailments and even death.

Typically in a procedure, a catheter is manipulated through a patient's vasculature to, for example, a patient's heart, and carries one or more electrodes which may be used for mapping, ablation, diagnosis, or other treatments. Once at the intended site, treatment may include radio frequency (RF) ablation, cryoablation, lasers, chemicals, high-intensity focused ultrasound, etc. An ablation catheter imparts such ablative energy to cardiac tissue to create a lesion in the cardiac tissue. This lesion disrupts undesirable electrical pathways and thereby limits or prevents stray electrical signals that lead to arrhythmias. As readily apparent, such treatment requires precise control of the catheter during manipulation to and at the treatment site, which can invariably be a function of a user's skill level.

The inventors herein have thus recognized a need for a system and method for precise and dynamic automated control of a catheter and its related components, for example, for diagnostic, therapeutic, mapping and ablative procedures, that will minimize and/or eliminate procedural variability due to a user's skill level. The inventors herein have also recognized a need for a system and method for performing user-specified procedures at the patient site or from a remote location.

BRIEF SUMMARY OF THE INVENTION

It is desirable to provide a system and method for precise and dynamic automated control of a catheter and its related components. In particular, it is desirable to provide a system and method for precise and dynamic automated control, for example, for diagnostic, therapeutic, mapping and ablative procedures, that will minimize and/or eliminate procedural variability due to a user's skill level, and minimize and/or eliminate radiation exposure from fluoroscopy by moving the staff away from the patient, with the procedures being optionally performed at the patient site or from a remote location.

A system and method for precise and dynamic automated control of a catheter and its related components may include a robotic catheter manipulator assembly including a support member including one or more catheter manipulation bases and one or more sheath manipulation bases movable relative to each other and to the support member. Each respective manipulation base may be releasably connectable to one or more catheter cartridges and one or more sheath cartridges. One or more drive mechanisms may be provided for moving the catheter and sheath manipulation bases relative to each other and to the support member.

For the robotic catheter manipulator assembly described above, in one embodiment, the catheter manipulation base or the catheter cartridge may include one or more fingers engageable with one or more complementary slider blocks in the other one of the catheter manipulation base or the catheter cartridge for controlling movement of a catheter by pulling a steering wire attached to the catheter and the finger or the slider block. In one embodiment, the sheath manipulation base or the sheath cartridge may include one or more fingers engageable with one or more complementary slider blocks in the other one of the sheath manipulation base or the sheath cartridge for controlling movement of a sheath by pulling a steering wire attached to the sheath and the finger or the slider block. In one embodiment, the finger may be movable by a motor driven lead screw or a ball screw (or alternatively, a belt drive, a rolling ring linear drive, or a piezo motor drive).

For the robotic catheter manipulator assembly described above, in one embodiment, the catheter manipulation base or the catheter cartridge may include one or more first elements engageable with one or more complementary second elements slidably engaged with the other one of the catheter manipulation base or the catheter cartridge for controlling movement of a catheter by pulling a steering wire attached to the catheter and the first or second element. In one embodiment, the sheath manipulation base or the sheath cartridge may include one or more first elements engageable with one or more complementary second elements slidably engaged with the other one of the sheath manipulation base or the sheath cartridge for controlling movement of a sheath by pulling a steering wire attached to the sheath and the first or second element.

For the robotic catheter manipulator assembly described above, in one embodiment, the assembly may include one or more recesses in the catheter manipulation base or the catheter cartridge for engagement with: one or more complementary locator detents on the other one of the catheter manipulation base or the catheter cartridge for alignment of the catheter cartridge relative to the catheter manipulation base, or one or more complementary locking detents on the other one of the catheter manipulation base or the catheter cartridge for releasable locking of the catheter cartridge with the catheter manipulation base.

For the robotic catheter manipulator assembly described above, in one embodiment, the assembly may include one or more recesses in the sheath manipulation base or the sheath cartridge for engagement with: one or more complementary locator detents on the other one of the sheath manipulation base or the sheath cartridge for alignment of the sheath cartridge relative to the sheath manipulation base, or one or more complementary locking detents on the other one of the sheath manipulation base or the sheath cartridge for releasable locking of the sheath cartridge with the sheath manipulation base.

For the robotic catheter manipulator assembly described above, in one embodiment, the assembly may include a means for aligning and/or releasably locking the catheter manipulation base with the catheter cartridge. In one embodiment, the assembly may include means for aligning and/or releasably locking the sheath manipulation base with the sheath cartridge. The catheter and sheath manipulation bases may each include a release lever operable to release a respectively connected catheter and sheath cartridge. In one embodiment, the support member may lie in a plane disposed at an acute angle relative to a generally horizontally disposed operation bed. Alternatively, the support member may lie in a plane disposed generally orthogonal to a generally horizontally disposed operation bed. In one embodiment, the catheter and sheath manipulation bases may be movable in a plane disposed at an acute angle relative to a generally horizontally disposed operation bed. Alternatively, the catheter and sheath manipulation bases may be movable in a plane disposed generally orthogonal to a generally horizontally disposed operation bed. In one embodiment, the catheter and sheath manipulation bases may be linearly movable relative to each other and to the support member. In one embodiment, the catheter manipulation base may be disposed generally behind the sheath manipulation base to allow insertion of a catheter into a sheath respectively connected to the catheter and sheath cartridges.

In one embodiment, a system and method for precise and dynamic automated control of a catheter and its related components may include a robotic catheter manipulator assembly including a support member including one or more manipulation bases releasably connectable to one or more cartridges. The manipulation base or the cartridge may include one or more fingers engageable with one or more complementary slider blocks slidably engaged with the other one of the manipulation base or the cartridge for controlling movement of a component connected to the cartridge. A drive mechanism may be provided for moving one or more of the fingers and the slider blocks.

For the robotic catheter manipulator assembly described above, in one embodiment, the cartridge may be a transseptal cartridge, a catheter cartridge or a sheath cartridge, and the component may respectively be a transseptal needle, a catheter or a sheath. In one embodiment, the drive mechanism may be a motor driven lead screw or a ball screw (or alternatively, a belt drive, a rolling ring linear drive, or a piezo motor drive). In one embodiment, the manipulation base may be movable by a motor driven lead screw or a ball screw (or alternatively, a belt drive, a rolling ring linear drive, or a piezo motor drive).

For the robotic catheter manipulator assembly described above, in one embodiment, the assembly may include one or more recesses in the manipulation base or the cartridge for engagement with: one or more complementary locator detents on the other one of the manipulation base or the cartridge for alignment of the cartridge relative to the manipulation base, or one or more complementary locking detents on the other one of the manipulation base or the cartridge for releasable locking of the cartridge with the manipulation base.

For the robotic catheter manipulator assembly described above, in one embodiment, the assembly may include means for aligning and releasably locking the manipulation base with the cartridge. In one embodiment, the manipulation base may include a release lever operable to release a connected cartridge. In one embodiment, the support member may lie in a plane disposed at an acute angle relative to a generally horizontally disposed operation bed. Alternatively, the support member may lie in a plane disposed generally orthogonal to a generally horizontally disposed operation bed. In one embodiment, the manipulation base may be movable in a plane disposed at an acute angle relative to a generally horizontally disposed operation bed. Alternatively, the manipulation base may be movable in a plane disposed generally orthogonal to a generally horizontally disposed operation bed.

In one embodiment, a system and method for precise and dynamic automated control of a catheter and its related components may include a robotic catheter manipulator assembly including a support member including one or more manipulation bases releasably connectable to one or more cartridges. The manipulation base or the cartridge may include one or more first elements engageable with one or more complementary second elements slidably engaged with the other one of the manipulation base or the cartridge for controlling movement of a component connected to the cartridge. A drive mechanism may be provided for moving the first and/or second elements.

For the robotic catheter manipulator assembly described above, in one embodiment, the cartridge may be a transseptal cartridge, a catheter cartridge or a sheath cartridge, and the component may respectively be a transseptal needle, a catheter or a sheath. In one embodiment, the component may be any surgically insertable device.

For the robotic catheter manipulator assembly described above, in one embodiment, the assembly may further include one or more recesses in the manipulation base or the cartridge for engagement with one or more complementary locator detents on the other one of the manipulation base or the cartridge for alignment of the cartridge relative to the manipulation base. In one embodiment, the assembly may include one or more recesses in the manipulation base or the cartridge for engagement with one or more complementary locking detents on the other one of the manipulation base or the cartridge for releasable locking of the cartridge with the manipulation base. In one embodiment, the support member may lie in a plane disposed at an acute angle relative to a generally horizontally disposed operation bed. Alternatively, the support member may lie in a plane disposed generally orthogonal to a generally horizontally disposed operation bed. In one embodiment, the manipulation base may be movable in a plane disposed at an acute angle relative to a generally horizontally disposed operation bed. Alternatively, the manipulation base may be movable in a plane disposed generally orthogonal to a generally horizontally disposed operation bed. In one embodiment, one of the first or second elements may be a finger and the other of the first or second elements may be a pin. In one embodiment, one of the first or second elements may be a finger and the other of the first or second elements may be a slider block. The assembly, in one embodiment, may include integrated force sensors operatively connected to the cartridge for permitting active tensioning of steering wires for controlling movement of the component connected to the cartridge. The assembly, in another embodiment, may include integrated force sensors operatively connected to the cartridge for limiting stress on the component by limiting movement of the cartridge.

The foregoing and other aspects, features, details, utilities and advantages of the present invention will be apparent from reading the following description and claims, and from reviewing the accompanying drawings.

BRIEF DESCRIPTION OF THE DRAWINGS

FIGS. 4c and 4d are respectively front and side views of a drive for the robotic catheter manipulator assembly of FIG. 3a;

FIG. 6c-6e are respectively enlarged side, top, and section A-A taken generally along line A-A in FIG. 6d, views of a first embodiment of a robotic catheter device cartridge, with FIG. 3a illustrating an exemplary usage of the robotic catheter device cartridge;

FIGS. 7a and 7b are enlarged isometric views, and FIG. 7c-7f are respectively enlarged left side, section A-A taken generally along line A-A in FIG. 7f, top and front views of a complementary robotic sheath device cartridge to the FIG. 6a robotic catheter device cartridge, with FIG. 3a illustrating an exemplary usage of the robotic sheath device cartridge;

FIGS. 9a-9d are respectively enlarged isometric, left side, top and front views of a second embodiment of a robotic catheter manipulator assembly;

FIGS. 10d-10g are respectively enlarged top and left side, and respectively sections A-A and B-B taken generally along lines A-A and B-B in FIG. 10d, of a second embodiment of a manipulation base;

FIGS. 12d-12i are respectively enlarged left side, right side, top, front, back and a corresponding left side view of a third embodiment of a robotic catheter manipulator assembly.

FIGS. 17d-17g are respectively enlarged top and right side, and respectively sections A-A and B-B taken generally along lines A-A and B-B in FIG. 17d, of a fourth embodiment of a manipulation base;

FIG. 18c-18e are respectively enlarged left side, bottom and front views of a fourth embodiment of a robotic catheter device cartridge, with FIG. 16a illustrating an exemplary usage of the robotic catheter device cartridge.

DETAILED DESCRIPTION OF EMBODIMENTS OF THE INVENTION

Figure 1:
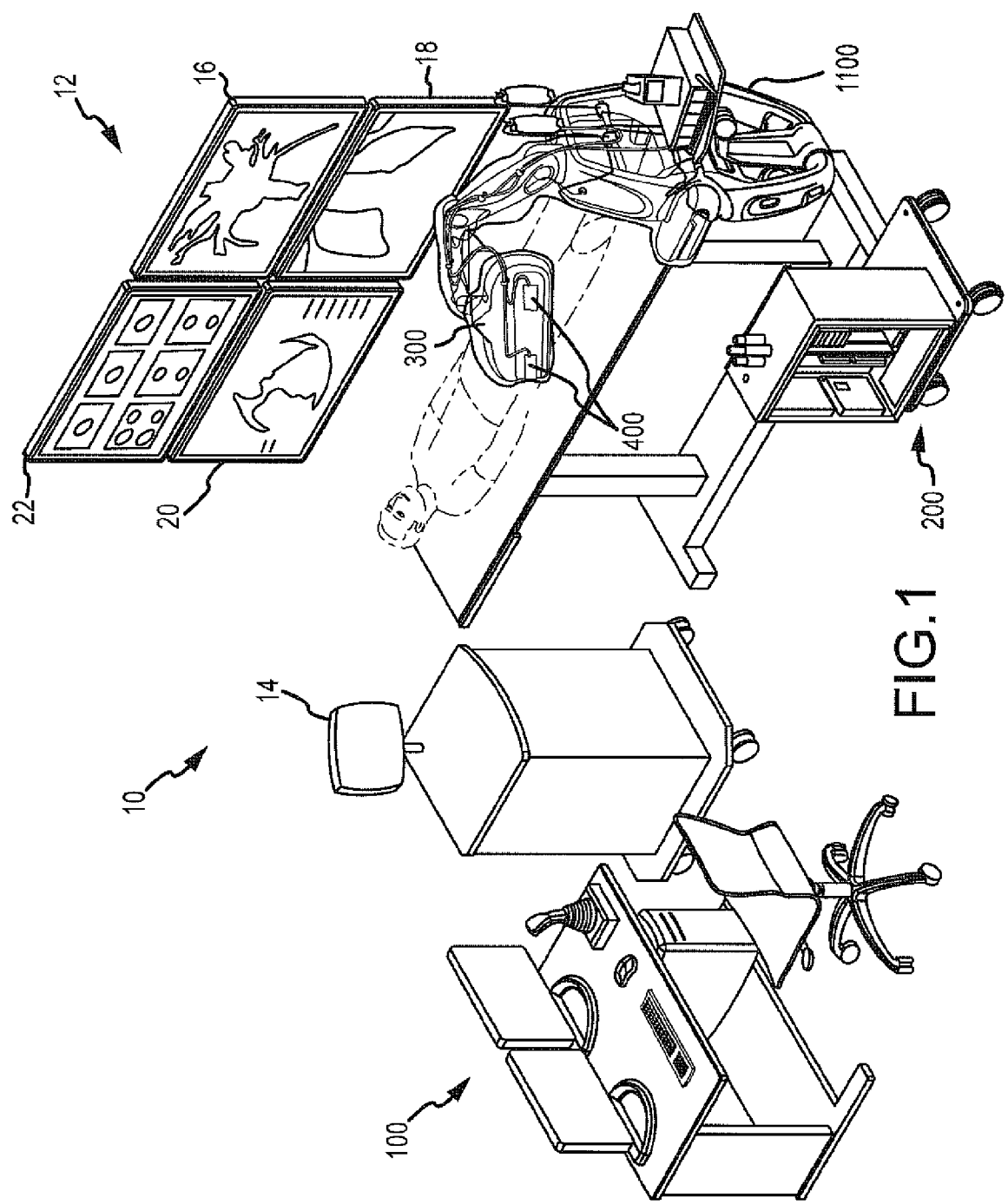
FIG. 1 is an isometric diagrammatic view of a robotic catheter system, illustrating an exemplary layout of various system components.

Referring now to the drawings wherein like reference numerals are used to identify identical components in the various views, an embodiment of robotic catheter system 10 (described in detail in commonly owned and copending application titled "Robotic Catheter System"), also referred to as "the system," may be likened to power steering for a catheter system. The system may be used, for example, to manipulate the location and orientation of catheters and sheaths in a heart chamber or in another body cavity. As shown in FIG. 1 and described in detail below, robotic catheter system 10 may generally incorporate a human input device and control system (referred to as "input control system") 100, e.g., a joystick and related controls (described in detail in commonly owned and copending applications titled "Robotic Catheter System Input Device" and "Robotic Catheter System Including Haptic Feedback"), that a user such as an electrophysiologist (EP) may interact with, an electronic control system 200 (described in detail in commonly owned and copending application titled "Robotic Catheter System with Dynamic Response") that translates motions of the user at the input device into a resulting movement of a catheter tip, and a visualization system 12 that provides a user with real-time or near-real-time positioning information concerning the catheter tip. The system may further include closed-loop feedback using an EnSite NavX system 14 and/or optical force transducers, a robotic catheter manipulator assembly 300 (described in detail below) for operating a robotic catheter device cartridge 400 (described in detail below and in commonly owned and copending applications titled "Robotic Catheter Device Cartridge" and "Robotic Catheter Rotatable Device Cartridge"), and manipulator support structure 1100 (described in detail in commonly owned and copending application titled "Robotic Catheter System"). The system provides the user with a similar type of control provided by a conventional manual system, but allows for repeatable, precise, and dynamic movements. The respective disclosures of the above-identified and other commonly owned and copending applications discussed in this application are incorporated herein by reference.

An embodiment of robotic catheter system 10 may involve automated catheter movement. A user, such as an EP, could identify locations (potentially forming a path) on a rendered computer model of the cardiac anatomy. The system can be configured to relate those digitally selected points to positions within a patient's actual/physical anatomy, and may command and control the movement of a catheter to defined positions. Once in position, either the user or system could then perform the desired treatment or therapy—which may further be in accordance with a defined algorithm. This system could enable full robotic control by using optimized path planning routines together with closed-loop position control. Furthermore, the system could automate certain "best-practices," such as pulling the catheter across the surface, or making contact at an oblique angle.

Referring to FIG. 1, input control system 100 will be described briefly.

Input control system 100 of commonly owned and copending application titled "Robotic Catheter System Input Device," may generally allow a user to control the movement and advancement of both the catheter and sheath. Generally, several types of joysticks may be employed, including, without limitation, instrumented traditional catheter handle controls, oversized catheter models, instrumented, user-wearable gloves, and traditional joysticks. In embodiments, for example and without limitation, the joystick may be spring centering so that any movement from the center position causes an incremental movement of the actual catheter tip, or the joystick may work in absolute terms. Haptic feedback may also be incorporated to provide a user with a sense of when contact has been made.

Referring to FIG. 1, electronic control system 200 will be described briefly.

As discussed in detail in commonly owned and copending applications titled "Robotic Catheter System Input Device," and "Robotic Catheter System with Dynamic Response," many additional features may be included with embodiments of the system to, for example, improve the accuracy or effectiveness of the system. Such features may include, closed-loop feedback using EnSite NavX system 14 for creating realistic cardiac chamber geometries or models, displaying activation timing and voltage data to identify arrhythmias, and guiding precise catheter movement, and/or optical force transducers; active tensioning of "passive" steering wires to reduce the system response time; cumulative ablation while the tip is following a front-to-back ironing motion; and/or reactive/resistive impedance monitoring.

Referring to FIG. 1, visualization system 12 will be described briefly.

As discussed in further detail in commonly owned and copending application titled "Robotic Catheter System," visualization system 12 may provide a user with real-time or near-real-time positioning information concerning the catheter tip. In an exemplary embodiment, system 12 may include an EnSite NavX monitor 16 for displaying cardiac chamber geometries or models, displaying activation timing and voltage data to identify arrhythmias, and for facilitating guidance of catheter movement. A fluoroscopy monitor 18 may be provided for displaying a real-time x-ray image or for assisting a physician with catheter movement. Additional exemplary displays may include an ICE and EP Pruka displays, 20, 22, respectively.

Referring to FIG. 1, EnSite NavX system 14 will be described briefly.

EnSite NavX system 14 (described in detail in U.S. Pat. No. 7,263,397, titled "Method and Apparatus for Catheter Navigation and Location and Mapping in the Heart," incorporated by reference in its entirety) may be provided for creating realistic cardiac chamber geometries or models, displaying activation timing and voltage data to identify arrhythmias, and guiding precise catheter movement. EnSite NavX system 14 may collect electrical data from catheters and use this information to track or navigate their movement and construct three-dimensional (3-D) models of the chamber.

Referring to FIGS. 1-3e and 6a-7f, the catheter and sheath configuration of robotic catheter manipulator assembly 300 and robotic catheter device cartridges 400 will be described in detail.

As generally shown in FIGS. 1, 2, 3a-3e, 9a-9d, 12a-12m and 16a-16m, and described in detail below, robotic catheter system 10 may include one or more robotic catheter manipulator assemblies 300 that serve as the mechanical control for the movements or actions of one or more robotic catheter device cartridges 400 (see FIGS. 1, 2, 6a-7f, 11a-11e, 14a-14e and 18a-19i; described in detail below and in commonly owned and copending applications titled "Robotic Catheter Device Cartridge" and "Robotic Catheter Rotatable Device Cartridge"). Whereas robotic catheter device cartridges 400 are described in detail in the aforementioned commonly owned and copending applications, cartridges 400 will also be described in detail below for facilitating an understanding of robotic catheter manipulator assemblies 300.

As generally shown in FIGS. 1 and 3a-3e and discussed in greater detail below, a first embodiment of a manipulator assembly 302 may respectively include both catheter and sheath manipulator mechanisms 304, 306. In this arrangement, the catheter and sheath manipulator mechanisms 304, 306 may be aligned such that the catheter can pass through the sheath in a coaxial arrangement. Each mechanism 304, 306 may be further capable of independent advancement/retraction (shown generally as directions $D_1$ and $D_2$) and independent four-wire steering control (e.g., eight total steering wires, comprising four sheath control wires and four catheter control wires), as discussed in detail below.

With a configuration of robotic catheter system 10, such as shown in FIGS. 1 and 3a-3e, there will be relative travel of a first embodiment of catheter and sheath cartridges 402, 404 and relative movement associated with a portion of a catheter 406 between the two cartridges 402, 404. For many embodiments, there may be a water-tight fit of a proximal sheath opening 408, which can sometimes create resistance to catheter advancement. In order to help eliminate/reduce the potential issue of columnar buckling of catheter 406, a length of stiff material, such as, for example, a solid metal rod or fiber reinforced composite, may be incorporated on the interior of the proximal portion of catheter 406. Such a material may locally increase the catheter's bending stiffness and provide enhanced buckling support. Thus catheter 406 may be proximally stiffened so that the length of the catheter proximally extending from sheath cartridge 404 is less likely to buckle during relative translation, as the entire length of catheter 406 extends into sheath 410.

For the manipulator and cartridge assemblies discussed below, a similarly stiffened proximal portion may be provided when catheter and sheath cartridges are used in the manner described above.

Referring to FIGS. 1-7f, the first embodiment of robotic catheter manipulator assembly 302 will be described in detail.

Figure 2:
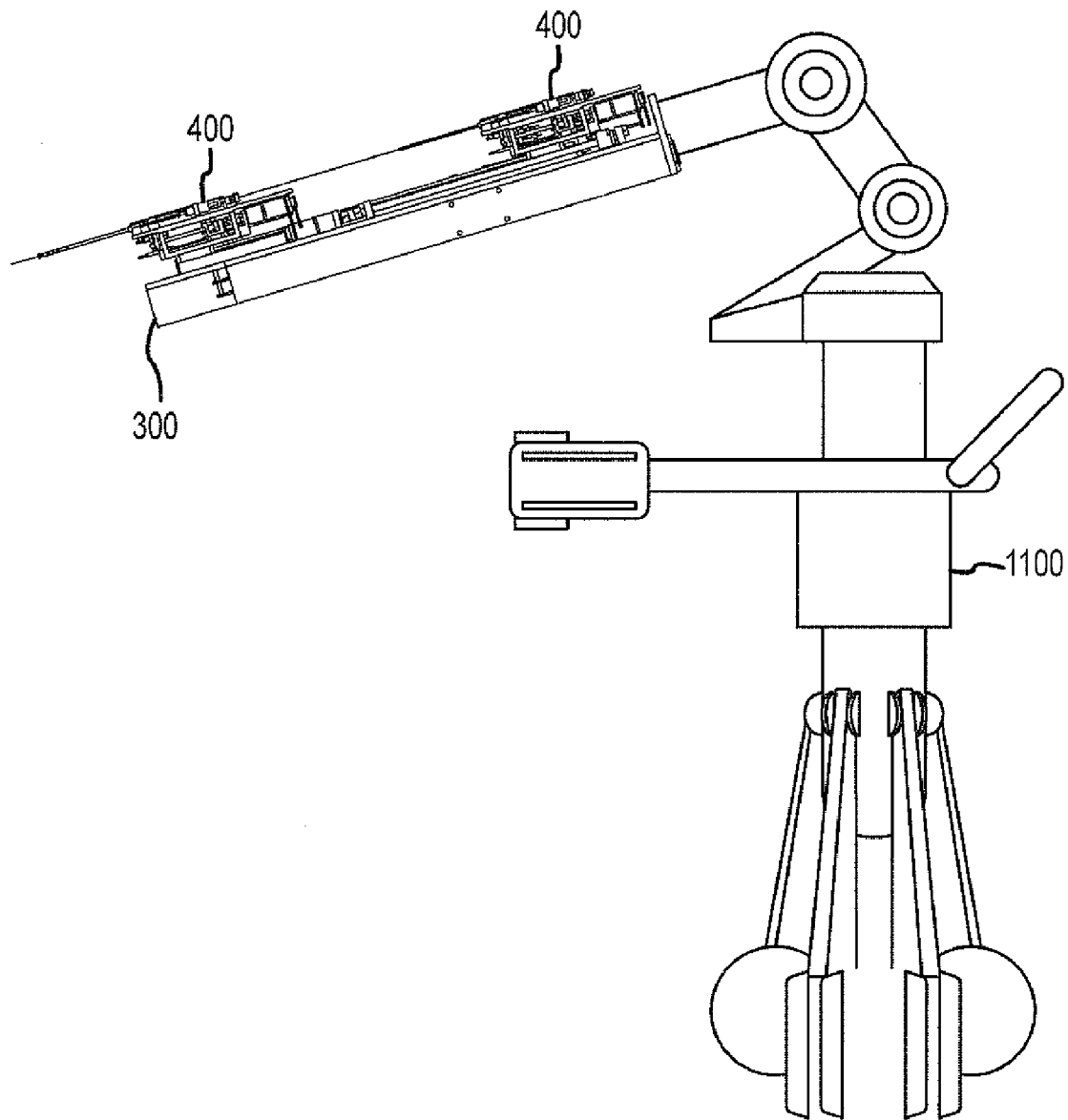
FIG. 2 is an isometric diagrammatic view of a first embodiment of a robotic catheter manipulator support structure, illustrating a robotic catheter manipulator slightly angled from a generally horizontal position.
Figure 3A:
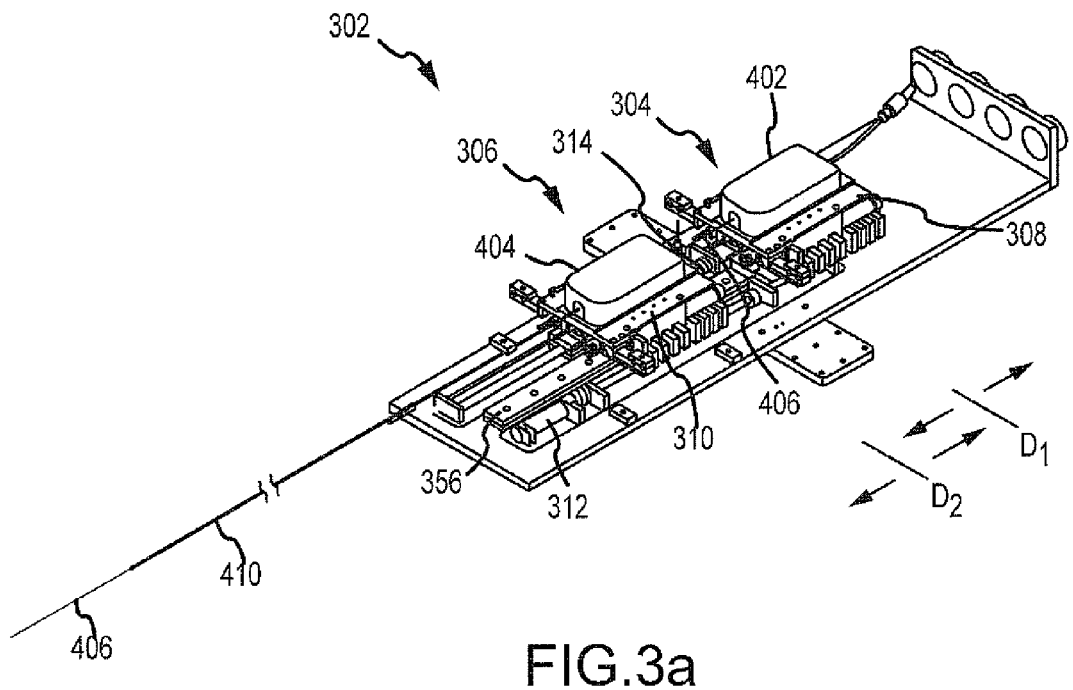
FIGS. 3a and 3b are enlarged isometric views.
Figure 3B:
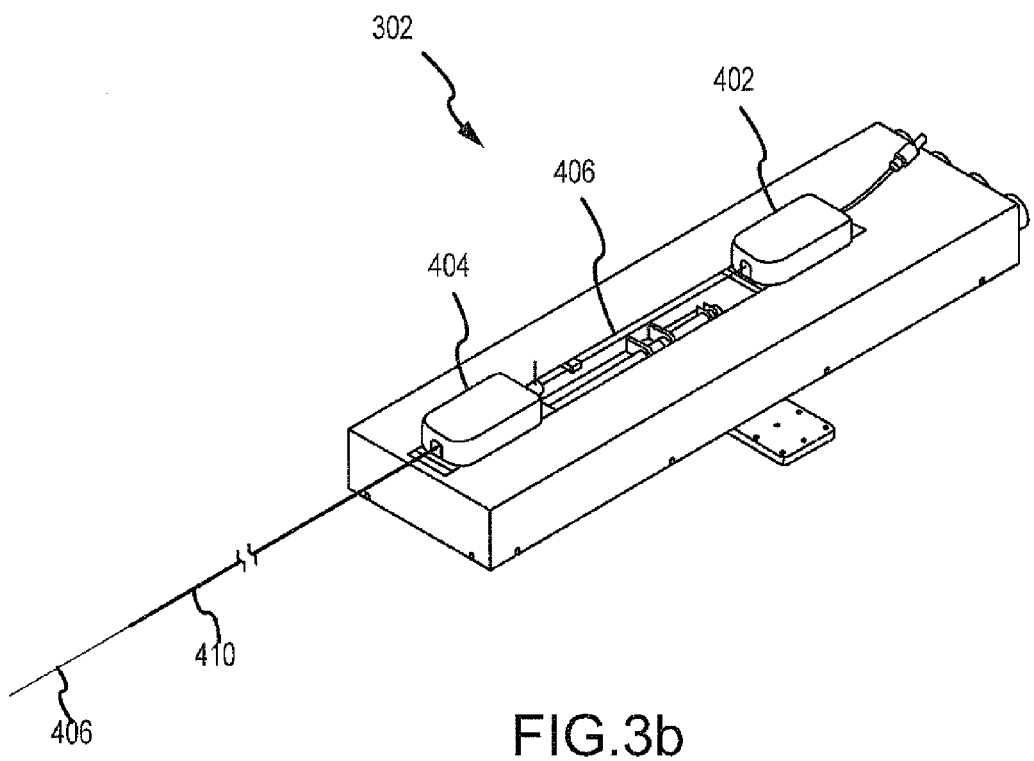
Figure 3C:
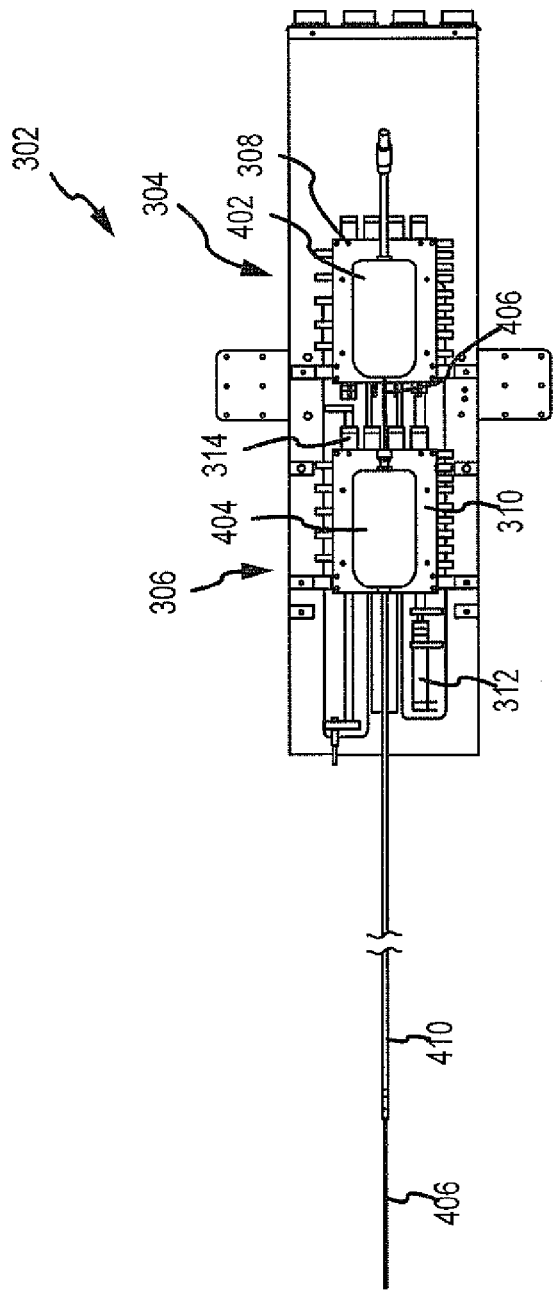
FIGS. 3c and 3d are respectively top and front views of a first embodiment of a robotic catheter manipulator assembly.
Figure 3D:
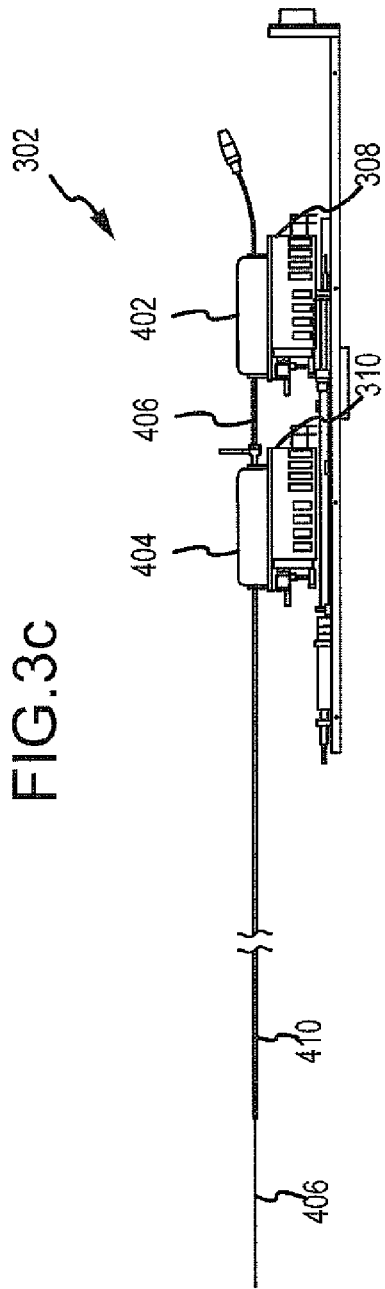
Figure 3E:
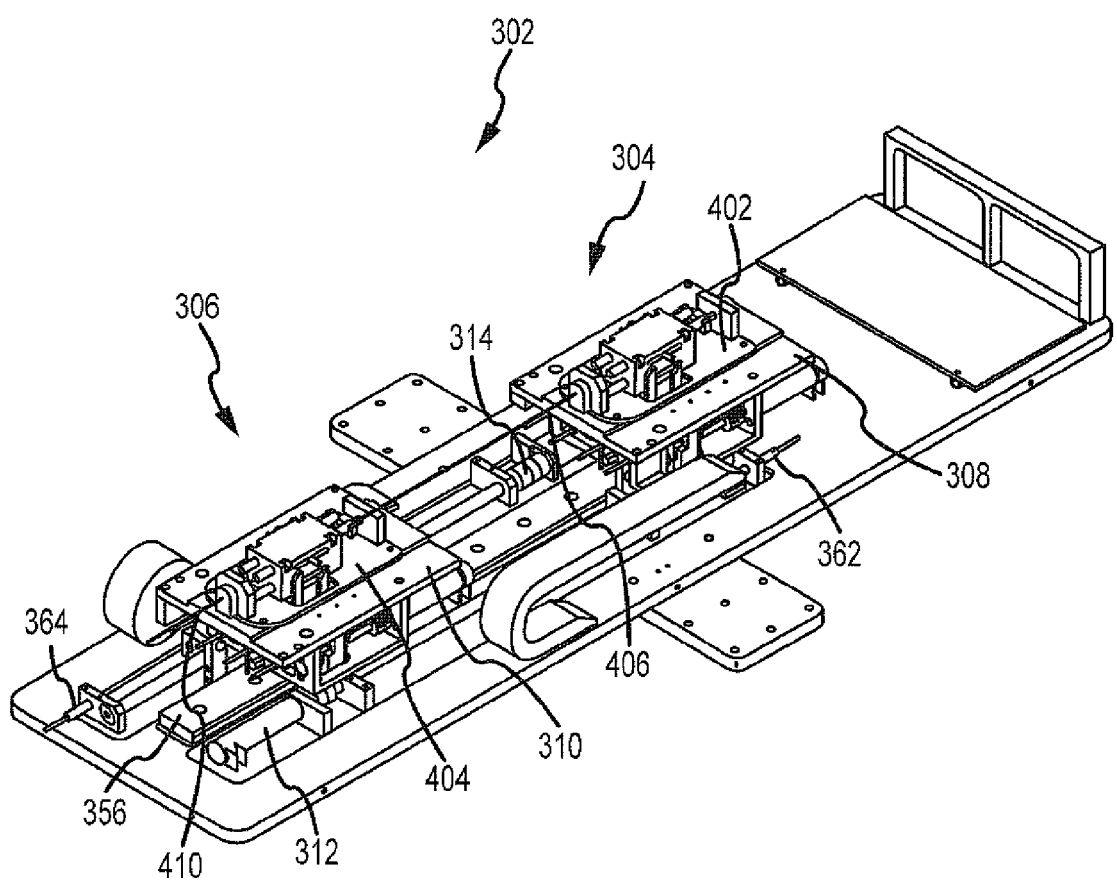
FIG. 3e is an enlarged isometric view of the robotic catheter manipulator assembly of FIG. 3a, with certain components removed for clarity.
Figure 4A:
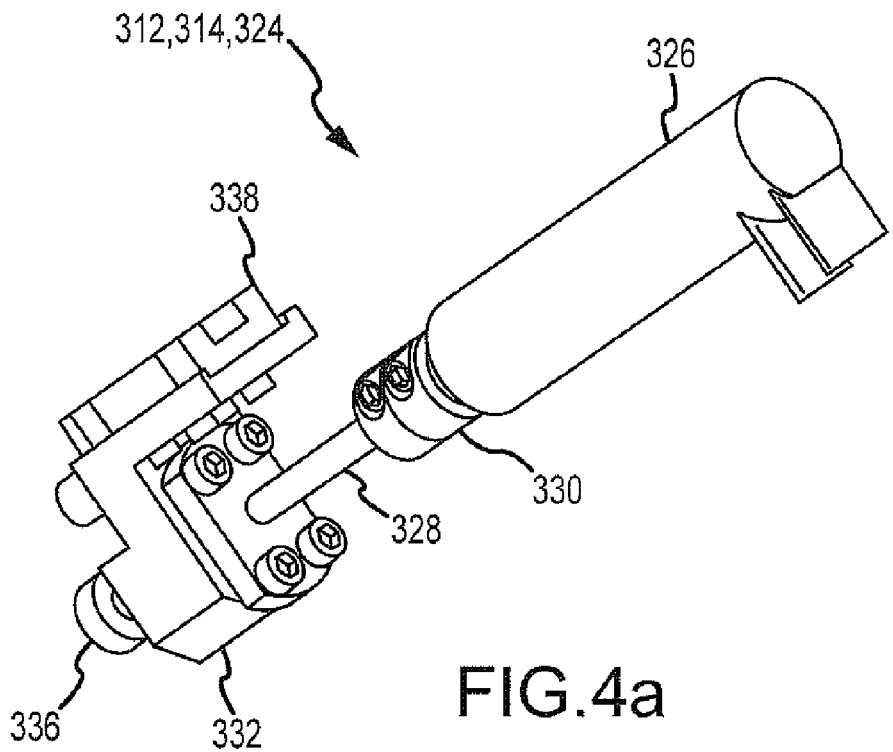
FIGS. 4a and 4b are enlarged isometric views.
Figure 4B:
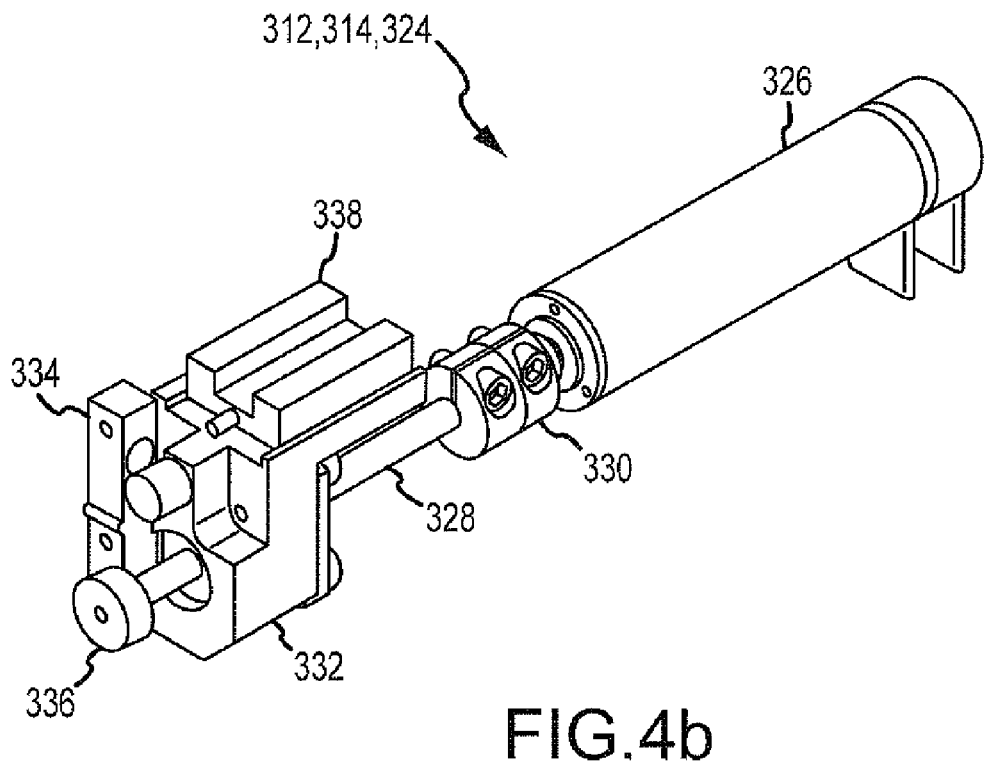

As generally shown in FIGS. 1-7f, robotic catheter system 10 which includes one or more robotic catheter manipulator assemblies 300, includes the first embodiment of robotic catheter manipulator assembly 302 including both catheter and sheath manipulation mechanisms 304, 306 for manipulating, for example, the first embodiment of catheter and sheath cartridges 402, 404 (see FIGS. 3a-3e). Manipulator assembly 302 may include interconnected/interlocking manipulation bases 308, 310 for catheter and sheath cartridges 402, 404, and likewise may include electrical "handshake" functionality as discussed below. Each interlocking manipulation base 308, 310 may be capable of travel in the longitudinal direction of the catheter/sheath ($D_1$, $D_2$ respectively). In an embodiment, $D_1$ and $D_2$ may each represent a translation of approximately 8 linear inches. As shown in FIGS. 3a, 3c and 3e, each interlocking base may be translated by high precision drive mechanisms 312, 314. Such drive mechanisms may include, for example and without limitation, a motor driven lead screw or ball screw (or alternatively, a belt drive, a rolling ring linear drive, or a piezo motor drive).

As shown in FIGS. 3e, 5a-5c, 6d and 7e, for each cartridge 402, 404, an associated manipulation base 308, 310 may include a plurality of fingers 316, 318, 320, 322, (e.g., one per steering wire) that extend or protrude upwardly to contact and interact with the steering wire pins 412, 414, 416, 418 to independently tension select steering wires 420, 422, 424, 426. As shown in FIGS. 3e and 6d, pins 414 and 418 may be respectively longer than pins 412 and 416 for engagement with extended fingers 318, 322. Each finger can be configured to be independently actuated by a precision drive mechanism, such as a motor driven ball screw 324 (see FIGS. 4a-4d), and may be outfitted with force sensors to measure corresponding steering wire tension. Each motor driven ball screw (for both finger control and cartridge translation control) may further include encoders to measure a relative and/or an absolute position of each element of the system. Home sensors 358, 362, 364 may be provided for respectively guiding catheter and sheath high precision drive mechanisms 312, 314 and associated manipulation bases 308, 310 to a safe position.

Figure 5A:
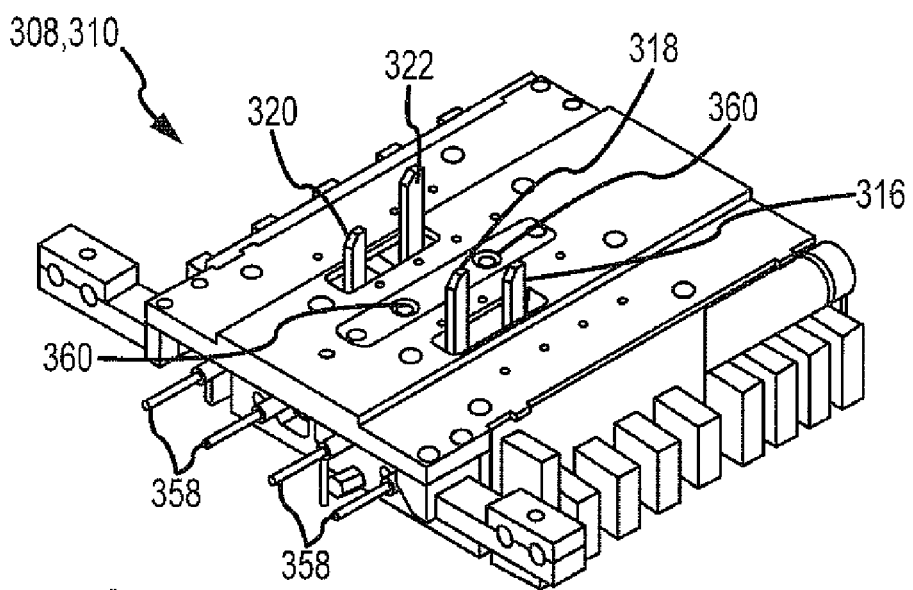
FIGS. 5a and 5b are enlarged isometric views of a first embodiment of a manipulation base, with FIG. 3a illustrating an exemplary usage of the manipulation base.
Figure 5B:
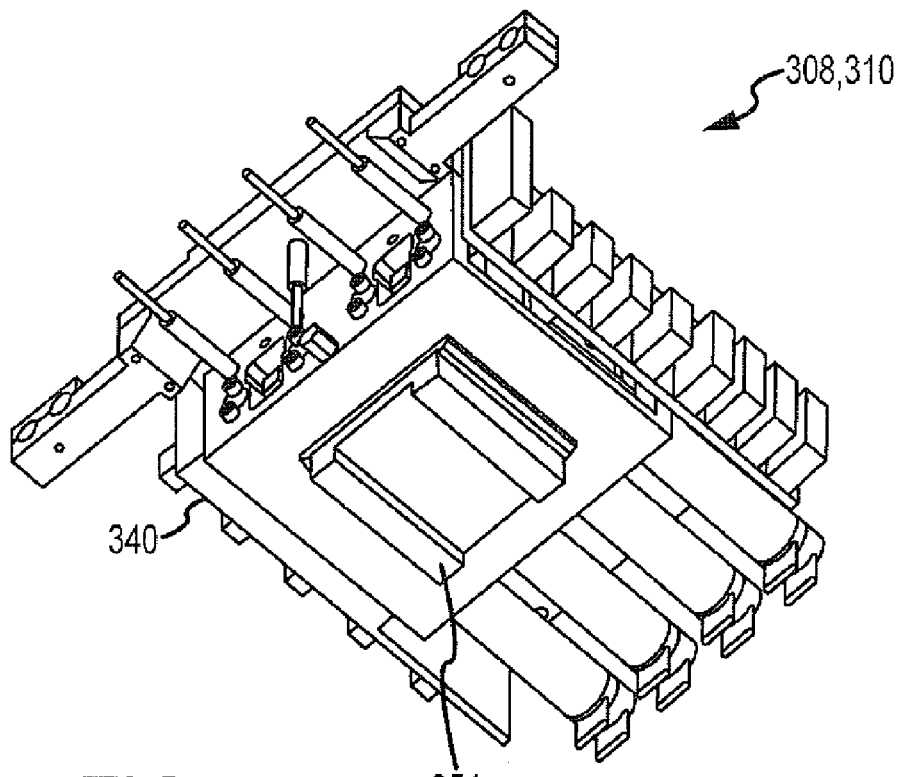
Figure 5C:
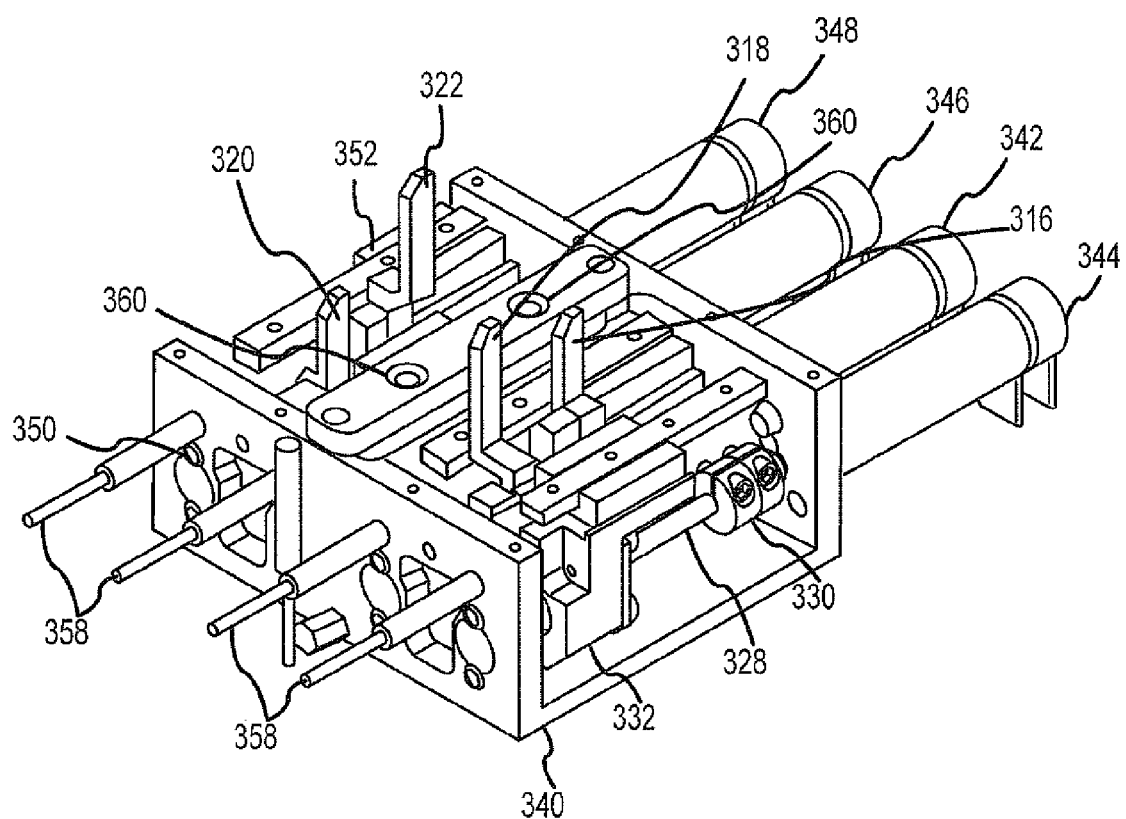
FIG. 5c is an enlarged isometric view of the manipulator base of FIG. 5a with certain components removed for clarity.

Referring to FIGS. 4a-4d, motor driven ball screw 324 may include exemplary components such as motor 326, leadscrew 328, coupler 330, bearing mount 332, strain gauge 334, radial bearing 336, and bearing 338. As shown in FIGS. 5a-5c, a respective bearing mount 332 and coupler 330 may engage frame 340 of manipulation bases 308, 310 and a corresponding finger 316, 318, 320 or 322 may be mounted adjacent strain gauge 334 (see FIG. 4b) for measuring the corresponding steering wire tension.

Referring to FIGS. 5a-5c, manipulation bases 308, 310 may include exemplary components such as motors 342, 344, 346 and 348, respectively coupled to fingers 316, 318, 320 and 322. A motor PC board 350 and a strain gauge PC board 352 may be mounted to frame 340 as shown, and a bearing 354 may be provided for sliding of each manipulation base 308, 310 on track 356

Manipulator assembly 302 may be disposed in a vertical configuration (see FIG. 1) for minimizing both the approach angle of the catheter and the distance the catheter must extend from the patient, or slightly angled from a generally horizontal position (see FIG. 2). In the vertical configuration of FIG. 1, the approach angle and catheter extension distance may be minimized by vertically orienting the backplane of the manipulator head, with the interlocking cartridges positioned at the lower extreme such that they may travel nearly horizontally and substantially in line with the point of entry into the patient (e.g., as generally illustrated in FIG. 1). In such an embodiment, with the backplane of the manipulator head vertically oriented, the positioning of the manipulator head structure may allow the proximal control of the catheter/sheath to be held closely to the patient's body without substantial structural interference.

Referring to FIGS. 1-3e and 5a-7f, the first embodiment of catheter and sheath cartridges 402, 404 will be described in detail.

As briefly discussed above, robotic catheter system 10 may include one or more cartridges 400, with the first embodiment of manipulator assembly 302 including at least two cartridges 402, 404, each of which may be respectively designed to control the distal movement of either catheter or sheath 406, 410. With respect to catheter cartridge 402, catheter 406 may be substantially connected or affixed to cartridge 402, so that advancement of cartridge 402 correspondingly advances catheter 406, and retraction of the cartridge retracts the catheter. As further shown in FIGS. 6a-6e and 7a-7f and briefly discussed above, in an embodiment, each cartridge 402, 404 may include a plurality of steering wire pins (such as pins 412, 414, 416, 418), each rigidly (and independently) connected or affixed to one of a plurality of catheter steering wires 420, 422, 424, 426 in a manner that permits independent tensioning of each steering wire. In a particular embodiment, pins 412, 414, 416, 418 may be movable to respectively pull steering wires 420, 422, 424, 426 in the down pull, left pull, right pull and up pull directions. The cartridges may be provided as a disposable item that is capable of being easily positioned (e.g., snapped) into place in an overall assembly. In an embodiment, as discussed in detail below, each cartridge may include an electrical "handshake" device or component to allow the system to properly identify the cartridge (e.g., by type and/or proper placement/positioning). Sheath cartridge 404 (FIGS. 7a-7f) may be designed in a similar manner as the catheter cartridge 402 (FIGS. 6a-6e), but will typically be configured to provide for the passage of catheter 406 via sheath opening 408. Manipulator assembly 302 may include a plurality (e.g., as many as ten or more) of independent driving mechanisms (e.g. motor driven ball screws 324).

For some embodiments, catheter and sheath cartridges 402, 404 can be designed to be substantially similar, and in that context a reference to either may relate to both. For example, as shown in FIGS. 6a-7f, the design of catheter and sheath cartridges 402, 404 may include upper and lower cartridge housing sections 428, 430. The system is not generally limited to specific material selection or formation techniques. However, in an embodiment, the upper and lower cartridge sections 428, 430 may be injection molded using a polycarbonate material. As discussed above, each steering wire pin 412, 414, 416, 418 may be connected to a separate catheter steering wire 420, 422, 424, 426, and may be formed of a Teflon-like material such as, for example, Delrin AF. When in contact with the cartridge block 432, such Teflon-like pins may maintain a low static and dynamic coefficient of friction and avoid the need for additional lubrication.

Referring to FIGS. 6a-7f, catheter and sheath cartridges 402, 404 may be configured to secure or lock down onto respective interconnecting catheter and sheath manipulation bases 308, 310. In order to couple cartridges 402, 404 with bases 308, 310, one or more locking/locating pins (e.g., 434 in FIGS. 6c, 6e, 7c and 7f) on the cartridge may engage one or more mating recesses in the base (e.g., 360 in FIG. 5c). In an embodiment, such recesses 360 may include an interference lock such as a spring detent or other locking means. In an embodiment, such other locking means may include a physical interference that may require affirmative/positive action by the user to release the cartridge. In the embodiment illustrated, cartridges 402, 404 may be snapped in and released from bases 308, 310 by exerting sufficient force to remove the cartridges. Catheter cartridge 402 (and sheath cartridge 404) may also include an electrical connection 436 for catheter instrumentation.

Figure 6C:
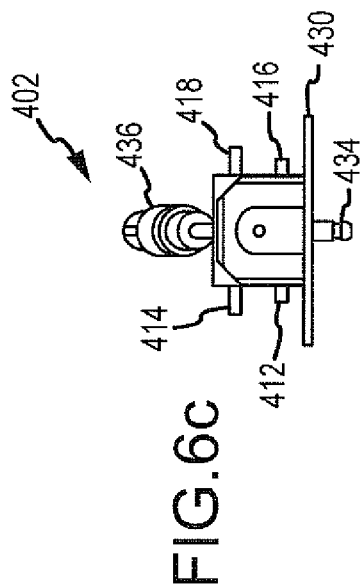
Figure 6B:
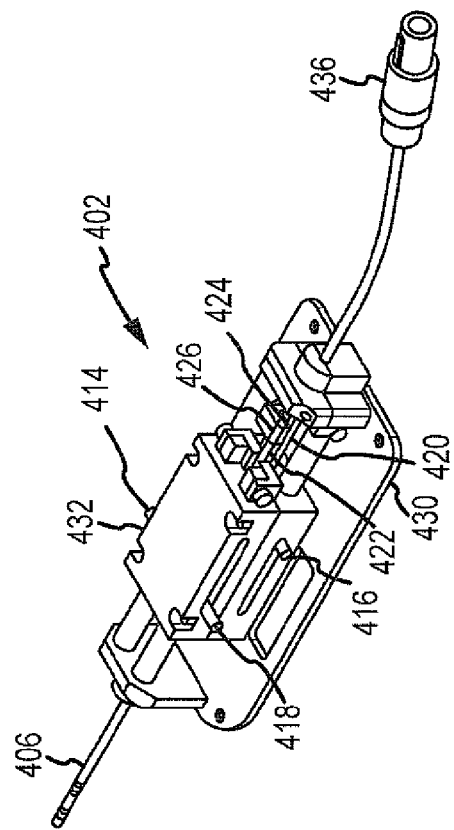
FIGS. 6a and 6b are enlarged isometric views.
Figure 6A:
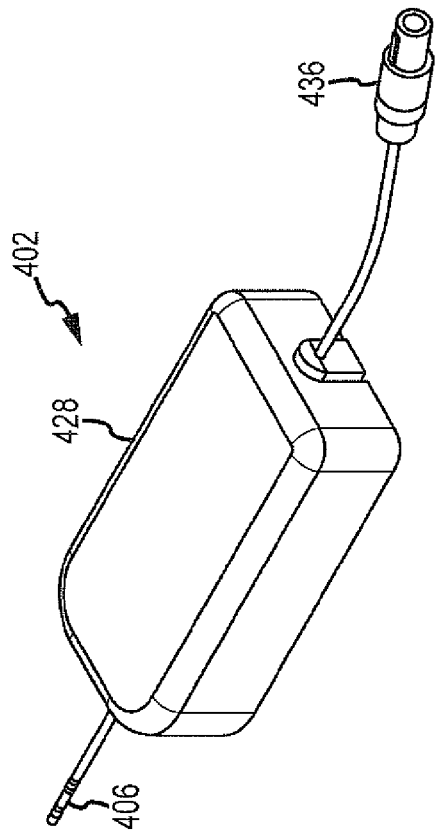

In an embodiment, a user (e.g. an EP) may first manually position catheter and sheath 406, 410 (with catheter 406 inserted in sheath 410) within the vasculature of a patient. Once the devices are roughly positioned in relation to the heart, the user may then engage or connect (e.g., "snap-in") the catheter cartridge into place on interconnecting/interlocking base 308, for example, by inserting the locking/locating pins 434 of the cartridge into mating recesses 360 of base 308. When the cartridge is interconnected with the base, each of the plurality of fingers 316, 318, 320, 322 respectively engage steering wire pins 412, 414, 416, 418, as discussed above. Each finger is designed to be actuated in a proximal direction to correspondingly push each respective steering wire pin (note: the embodiment of FIG. 6b shows pins 418 in a fully extended position before being moved by finger 322 to a fully retracted position, such as that of pin 416).

With sufficiently rigid coupling between each steering wire pin and a corresponding steering wire, pushing a steering wire pin in a proximal direction may cause an attached steering wire to tension and thus laterally deflect the distal end of catheter 406 and sheath 410. For example, as discussed above, pushing pins 412, 414, 416, 418 may respectively pull steering wires 420, 422, 424, 426 in the down pull, left pull, right pull and up pull directions. Moreover, in such an embodiment, because there is no rigid connection between each finger and its associated steering wire pin, manipulator assembly 302 cannot pull the steering wire in a forward direction. That is, when each steering wire pin is actuated, it is only possible to tension the steering wire.

Figure 8A:
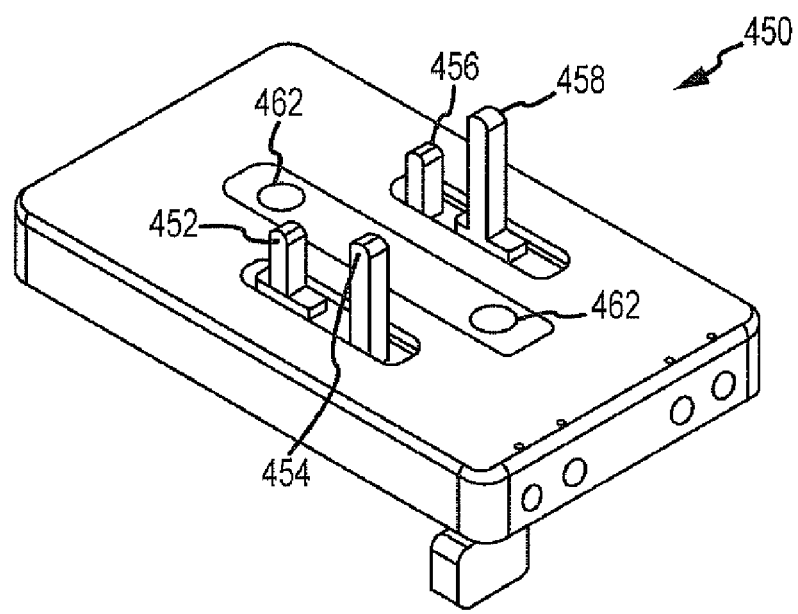
FIGS. 8a and 8b are enlarged isometric views of an override assembly.
Figure 8B:
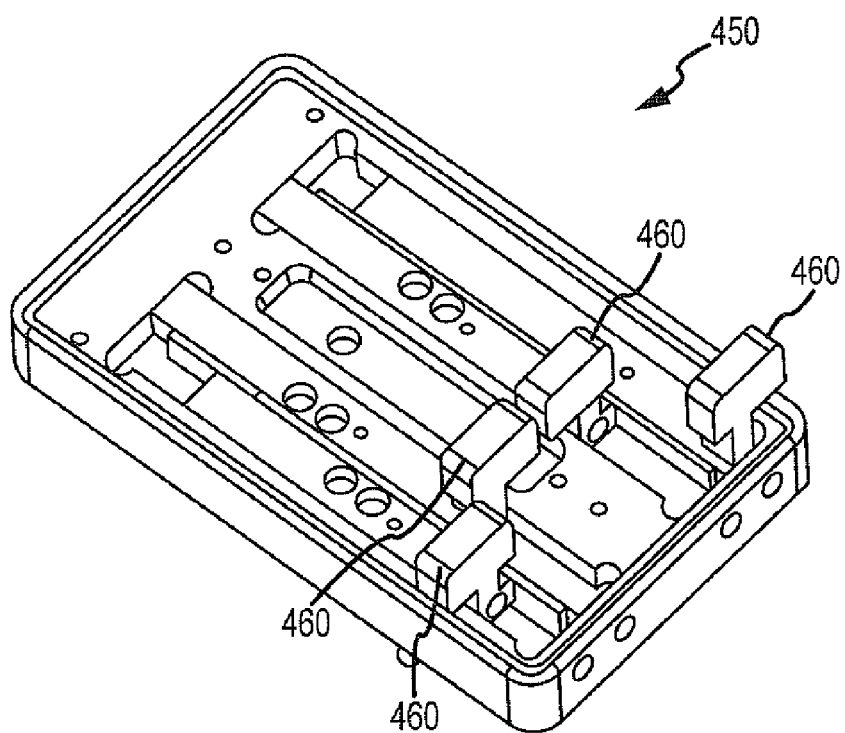

Referring to FIGS. 8a and 8b, an override assembly 450 will be described in detail.

Override assembly 450 may be provided to operate with manipulator assembly 302 as a secondary means for manually moving pins 412, 414, 416, 418. Override assembly may include fingers 452, 454, 456, 458 that respectively engage with pins 412, 414, 416, 418 of catheter or sheath cartridges 402, 404. Each finger 452, 454, 456, 458 may include a manual handle 460 for operating a respective finger. Thus in use, a user may attach a cartridge 402, 404 to override assembly 450 by inserting locking/locating pins 434 of the cartridge into mating recesses 462. Once the cartridge is snapped onto override assembly 450, the user may manually pull an appropriate handle 460 to manually move pins 412, 414, 416, 418 and therefore steering wires 420, 422, 424, 426.

Referring to FIGS. 1, 2 and 9a-11e, a second embodiment of robotic catheter manipulator assembly 500 will be described in detail.

Figure 9A:
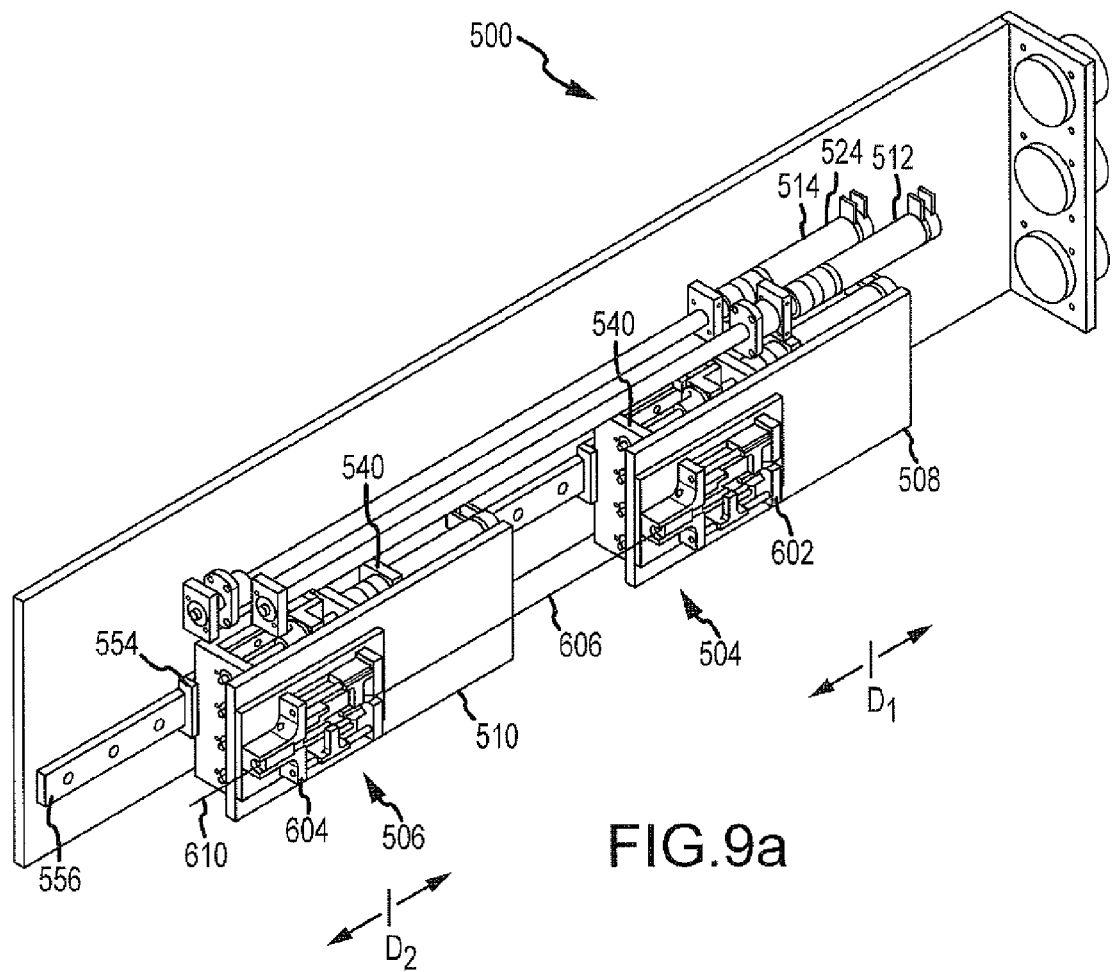
Figure 10A:
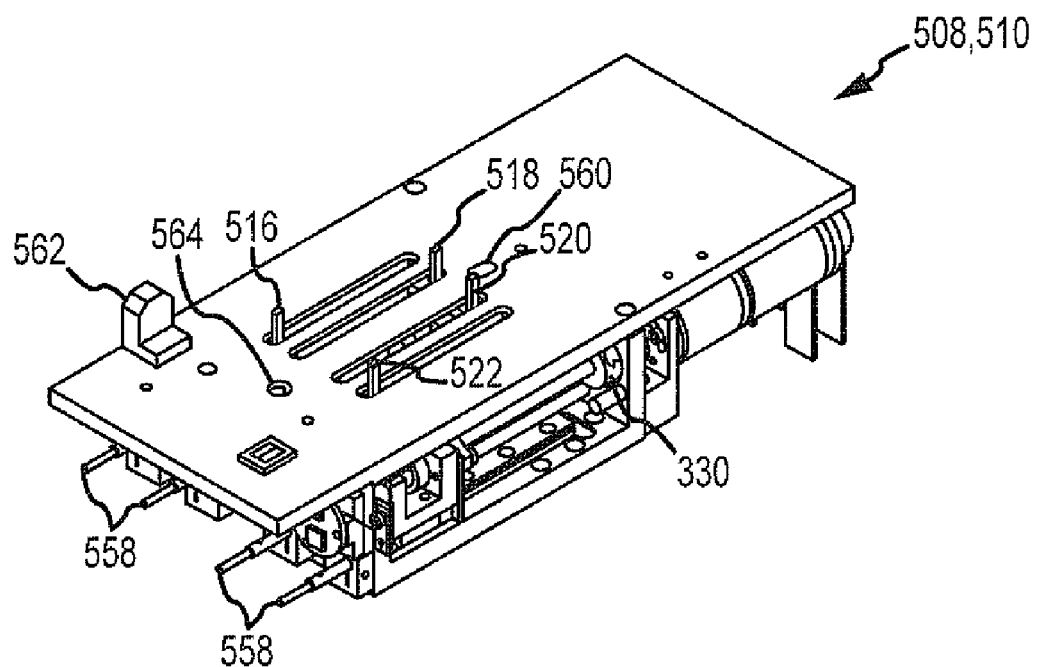
FIGS. 10a-10c are enlarged isometric views.
Figure 10B:
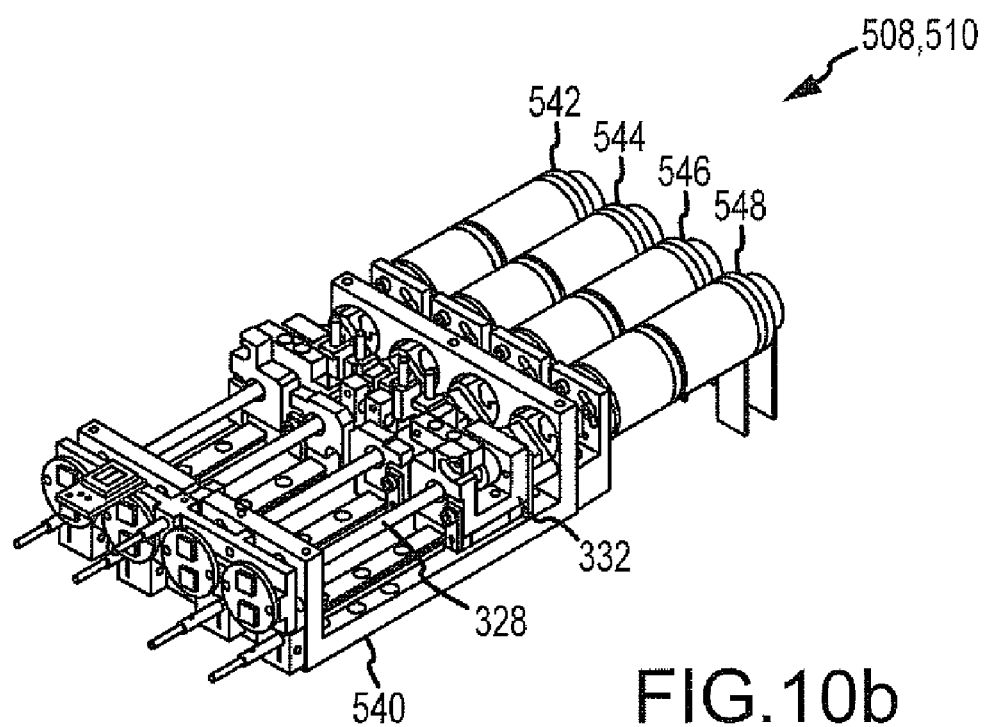
Figure 10C:
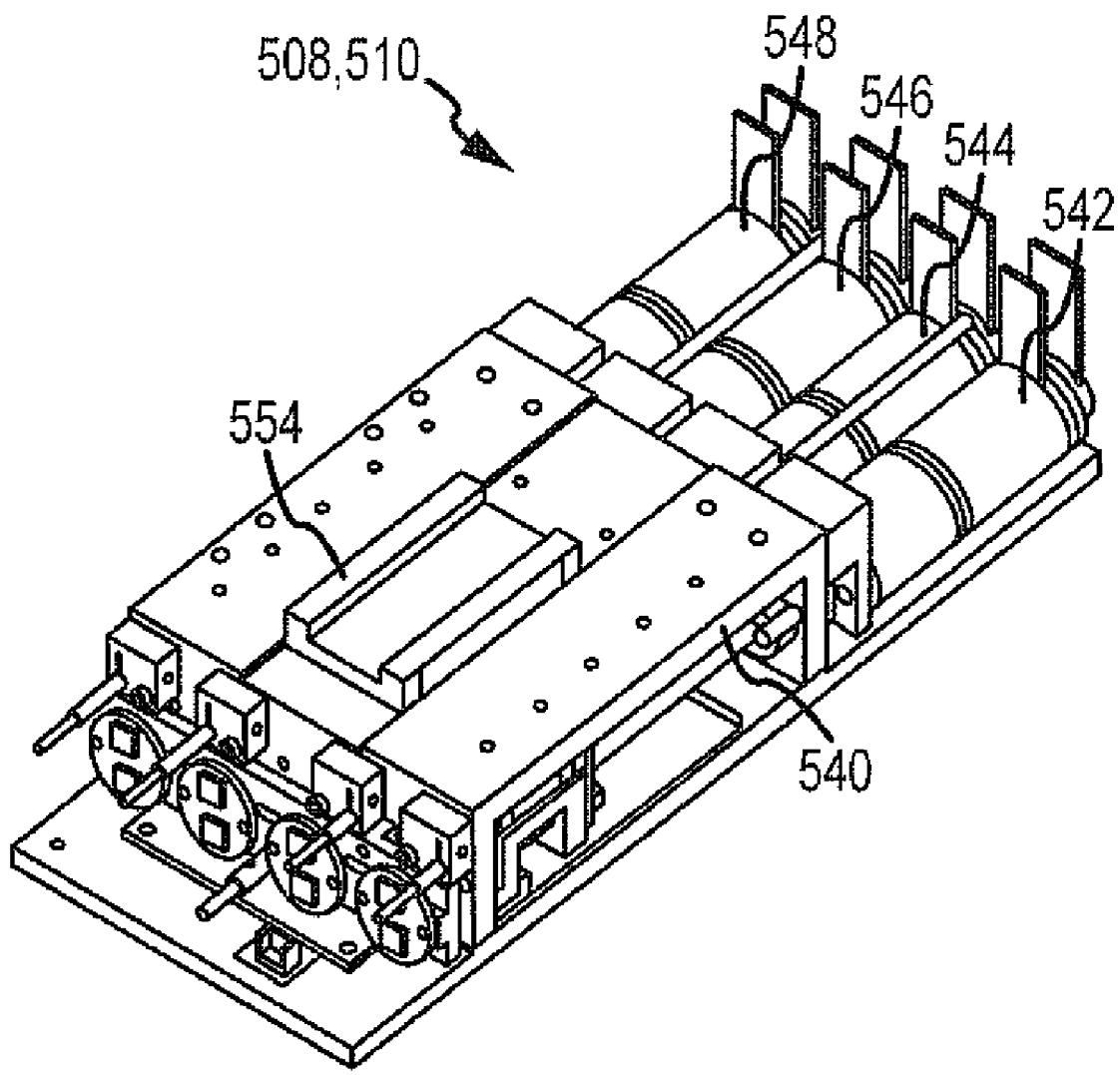

As generally shown in FIGS. 1, 2 and 9a-11e, robotic catheter system 10 which includes one or more robotic catheter manipulator assemblies 300, includes the second embodiment of robotic catheter manipulator assembly 500 including both catheter and sheath manipulation mechanisms 504, 506 for manipulating, for example, a second embodiment of catheter and sheath cartridges 602, 604 (see FIGS. 11a-11e). Manipulator assembly 500 may include interconnected/interlocking manipulation bases 508, 510 for catheter and sheath cartridges 602, 604, and likewise may include electrical "handshake" functionality as discussed below. Each interlocking base 508, 510 may be capable of travel in the longitudinal direction of the catheter/sheath ($D_1$, $D_2$ respectively). In an embodiment, $D_1$ and $D_2$ may each represent a translation of approximately 8 linear inches. As shown in FIG. 9a (similar to the first embodiment of manipulator assembly 302 for FIGS. 3a, 3c and 3e), each interlocking base may be translated by high precision drive mechanisms 512, 514. Such drive mechanisms may include, for example and without limitation, a motor driven lead screw or ball screw (or alternatively, a belt drive, a rolling ring linear drive, or a piezo motor drive).

As shown in FIGS. 9a-11e, for each cartridge 602, 604, an associated manipulation base 508, 510 may include a plurality of fingers 516, 518, 520 and 522, (e.g., one per steering wire) that extend or protrude upwardly to contact and interact with the steering wire slider blocks 612, 614, 616, 618 to independently tension select steering wires 620, 622, 624, 626. Each finger can be configured to be independently actuated by a precision drive mechanism, such as a motor driven ball screw 524 (see also FIGS. 4a-4d and description above for a detailed description of ball screw 324), and may be outfitted with force sensors to measure corresponding steering wire tension. Each motor driven ball screw (for both finger control and cartridge translation control) may further include encoders to measure a relative and/or an absolute position of each element of the system.

As discussed above, referring to FIGS. 4a-4d, motor driven ball screw 324 may include exemplary components such as motor 326, leadscrew 328, coupler 330, bearing mount 332, strain gauge 334, radial bearing 336, and bearing 338. As shown in FIGS. 10a-10g, a respective bearing mount 332 and coupler 330 may engage frame 540 of manipulation bases 508, 510 and a corresponding finger 516, 518, 520 or 522 may be mounted adjacent strain gauge 334 (see FIGS. 4a-4d) for measuring the corresponding steering wire tension.

Referring to FIGS. 10a-10g, manipulation bases 508, 510 may include exemplary components such as motors 542, 544, 546 and 548, respectively coupled to fingers 516, 518, 520 and 522. A bearing 554 may be provided for sliding of each manipulation base 508, 510 on track 556. A plurality of inductive sensors (e.g. home sensors) 558 may be provided for guiding each manipulation base to a safe position.

As with manipulator assembly 302, manipulator assembly 500 may be disposed in a vertical configuration (see FIG. 1) for minimizing both the approach angle of the catheter and the distance the catheter must extend from the patient, or slightly angled from a generally horizontal position (see FIG. 2). In the vertical configuration of FIG. 1, the approach angle and catheter extension distance may be minimized by vertically orienting the backplane of the manipulator head, with the interlocking cartridges positioned at the lower extreme such that they may travel nearly horizontally and substantially in line with the point of entry into the patient (e.g., as generally illustrated in FIG. 1). In such an embodiment, with the backplane of the manipulator head vertically oriented, the positioning of the manipulator head structure may allow the proximal control of the catheter/sheath to be held closely to the patient's body without substantial structural interference. In an embodiment, high-precision drive mechanisms 512, 514 that are capable of translating each of the catheter and sheath cartridges 602, 604 may be positioned on the mid-to-upper extreme of the assemblies to allow the respective cartridges to be positioned lower (e.g., with a lower profile) on the manipulator. By holding a close distance, the ingress angle of the catheter/sheath may be minimized, and the manipulator control may be positioned more closely to an insertion site.

Referring to FIGS. 1, 2 and 9a-11e, the second embodiment of catheter and sheath cartridges 602, 604 will be described in detail.

As briefly discussed above, robotic catheter system 10 may include one or more cartridges 400, with the second embodiment of manipulator assembly 500 including at least two cartridges 602, 604, each of which may be respectively designed to control the distal movement of either the catheter or the sheath. With respect to catheter cartridge 602, catheter 606 may be substantially connected or affixed to cartridge 602, so that advancement of cartridge 602 correspondingly advances catheter 606, and retraction of the cartridge retracts the catheter. As further shown in FIGS. 11a-11e and discussed above, in an embodiment, each cartridge 602, 604 may include slider blocks (e.g., 612, 614, 616, 618), each rigidly (and independently) connected or affixed to one of a plurality of catheter steering wires (e.g., 620, 622, 624, 626) in a manner that permits independent tensioning of each steering wire. Each slider block 612, 614, 616, 618 may be slidably disposed on a respective rod 636, 638, 640, 642. The cartridge may be provided as a disposable item that is capable of being easily positioned (e.g., snapped) into place in an overall assembly. In an embodiment, as discussed in detail below, the cartridge may include an electrical "handshake" device or component to allow the system to properly identify the cartridge (e.g., by type and/or proper placement/positioning). Sheath cartridge 604 may be designed in a similar manner as the catheter cartridge 602, but will typically be configured to provide for the passage of catheter 606. Manipulator assembly 500 may include a plurality (e.g., as many as ten or more) of independent driving mechanisms (e.g. motor driven ball screws 524).

For some embodiments, the catheter and sheath cartridge can be designed to be substantially similar, and in that context a reference to either may relate to both. For example, as shown in FIGS. 11a-11e, the design of the catheter, sheath cartridge 602, 604 may include upper and lower cartridge sections 628, 630, and independent slider blocks 612, 614, 616, 618. The system is not generally limited to specific material selection or formation techniques. However, in an embodiment, the upper and lower cartridge sections 628, 630, may be injection molded using a polycarbonate material. Each slider block 612, 614, 616, 618 may be connected to a separate catheter steering wire 620, 622, 624, 626, and may be formed of a Teflon-like material such as, for example, Delrin AF. When in contact with rods 636, 638, 640, 642, such Teflon-like slider blocks may maintain a low static and dynamic coefficient of friction and may avoid the need for additional lubrication.

Figure 11A:
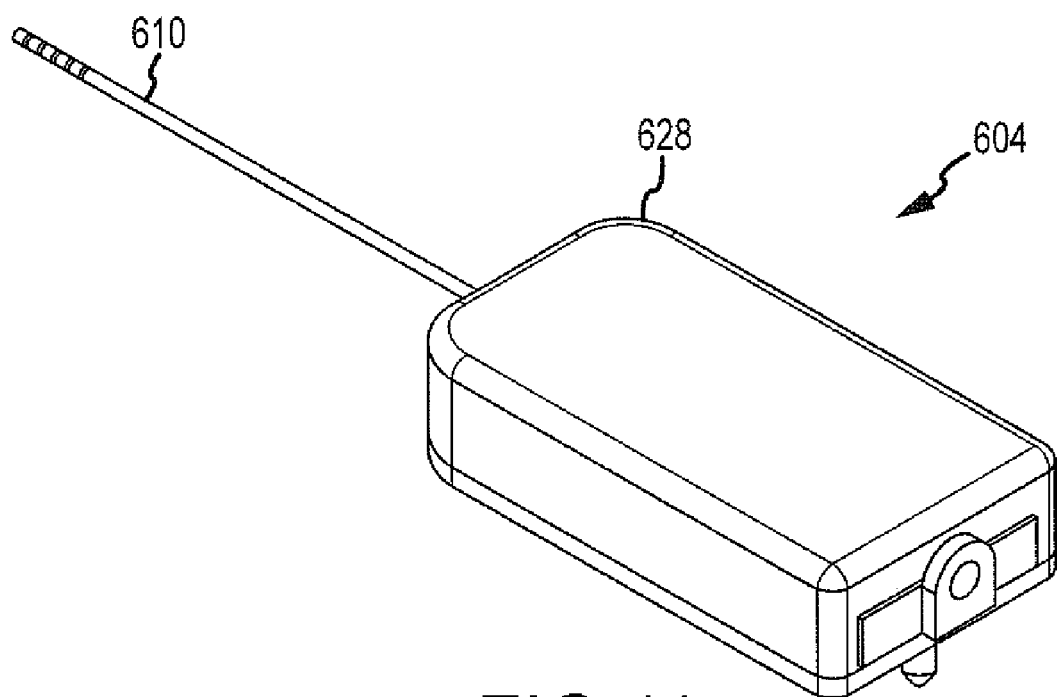
FIGS. 11a and 11b (with certain components removed) are enlarged isometric views.
Figure 11B:
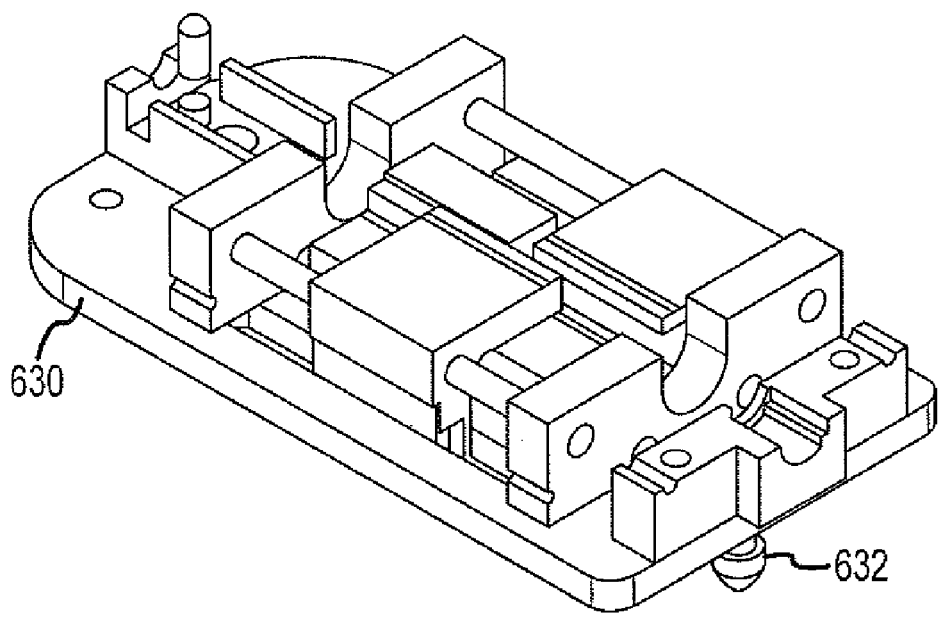
Figure 11C:
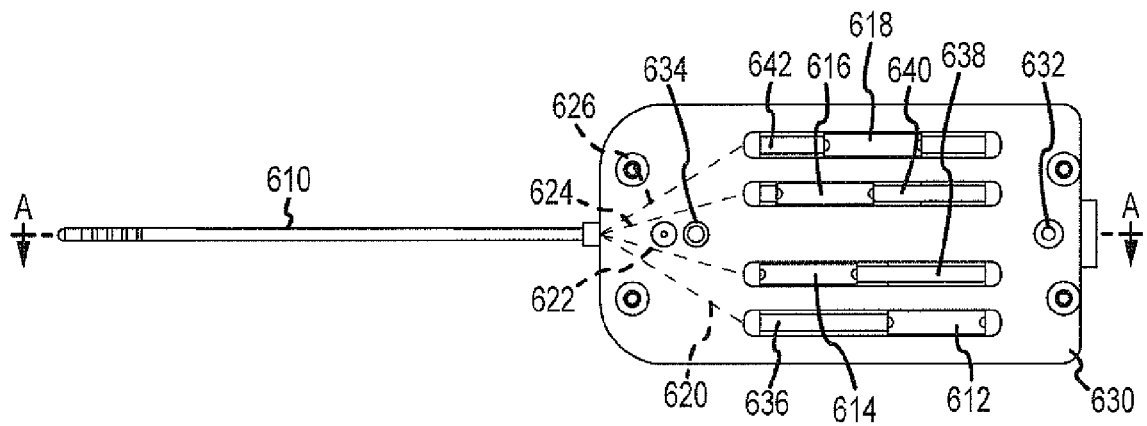
FIG. 11c-11e are respectively enlarged bottom, front and section A-A taken generally along line A-A in FIG. 11c, views of a second embodiment of a robotic sheath device cartridge, with FIG. 9a illustrating an exemplary usage of the robotic sheath device cartridge.
Figure 11D:
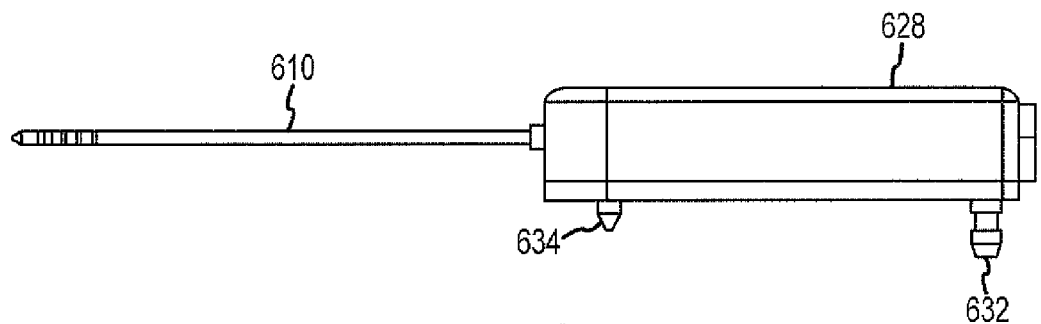
Figure 11E:
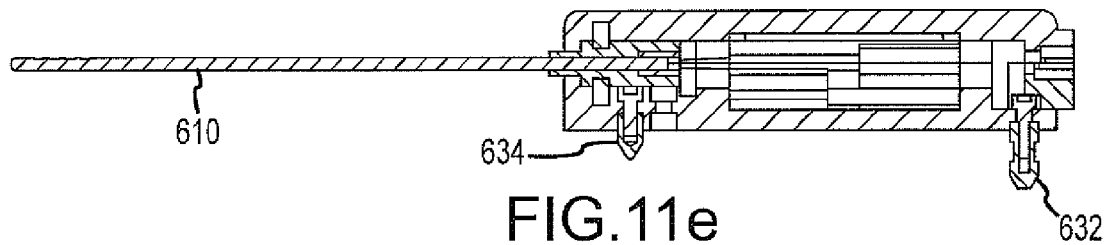

Referring to FIGS. 11a-11e, catheter and sheath cartridges 602, 604 may be configured to secure or lock down onto respective interconnecting catheter and sheath manipulation bases 508, 510. To couple cartridge 602 (and 604) with base 508 (and 510), one or more locking pins (e.g., 632 in FIGS. 11c and 11e) on the cartridge may engage one or more mating recesses 560 in the base (see FIG. 10a). In an embodiment, such recesses 560 may include an interference lock such as a spring detent or other locking means. In an embodiment, such other locking means may include a physical interference that may require affirmative/positive action by the user to release the cartridge. Such action may include or require actuation of a release lever 562. Additionally, as shown in FIGS. 11c and 11e, cartridge 602 (and 604) may include one or more locator pins 634 that are configured to passively fit into mating holes on the base (e.g., 564 in FIG. 10a).

In an embodiment, a user (e.g. an EP) may first manually position catheter 606 and sheath 610 (with catheter 606 inserted in sheath 610) within the vasculature of a patient. Once the devices are roughly positioned in relation to the heart, the user may then engage or connect (e.g., "snap-in") the catheter cartridge into place on interconnecting/interlocking base 508 of manipulator assembly 500, for example, by inserting the locking/locating pins 632, 634 of the cartridge into mating recesses 560, 564 of base 508. When the cartridge is interconnected with the base, each of the plurality of fingers 516, 518, 520 or 522 may fit into recesses formed between the distal edge of slider blocks 612, 614, 616, 618 and lower cartridge section 630. Such recesses are shown in, for example, FIG. 11c.

Each finger may be designed to be actuated in a proximal direction to correspondingly push each respective slider block. The slider block can be configured to force the finger to self center on its geometry when contact is first made. Such a centering feature may be facilitated by the contact surface of the slider block. For example, as shown in FIG. 11c, the slider block may include an engagement surface (e.g., shaped as a semi-cylindrical recess in the forward facing portion). This surface may be configured to mate or communicate with a matching round portion of a corresponding finger.

With sufficiently rigid coupling between each slider block and a corresponding steering wire, pushing a slider block in a proximal direction may cause an attached steering wire to tension and thus laterally deflect the distal end of the catheter and sheath 606, 610. Moreover, in such an embodiment, because there is no rigid connection between each finger and its associated slider block, the manipulator assembly 500 cannot pull the steering wire in a forward direction. That is, when each block is actuated, it is only possible to tension the steering wire.

Referring to FIGS. 1, 2 and 12a-14e, a third embodiment of robotic catheter manipulator assembly 700 will be described in detail.

Figure 12A:
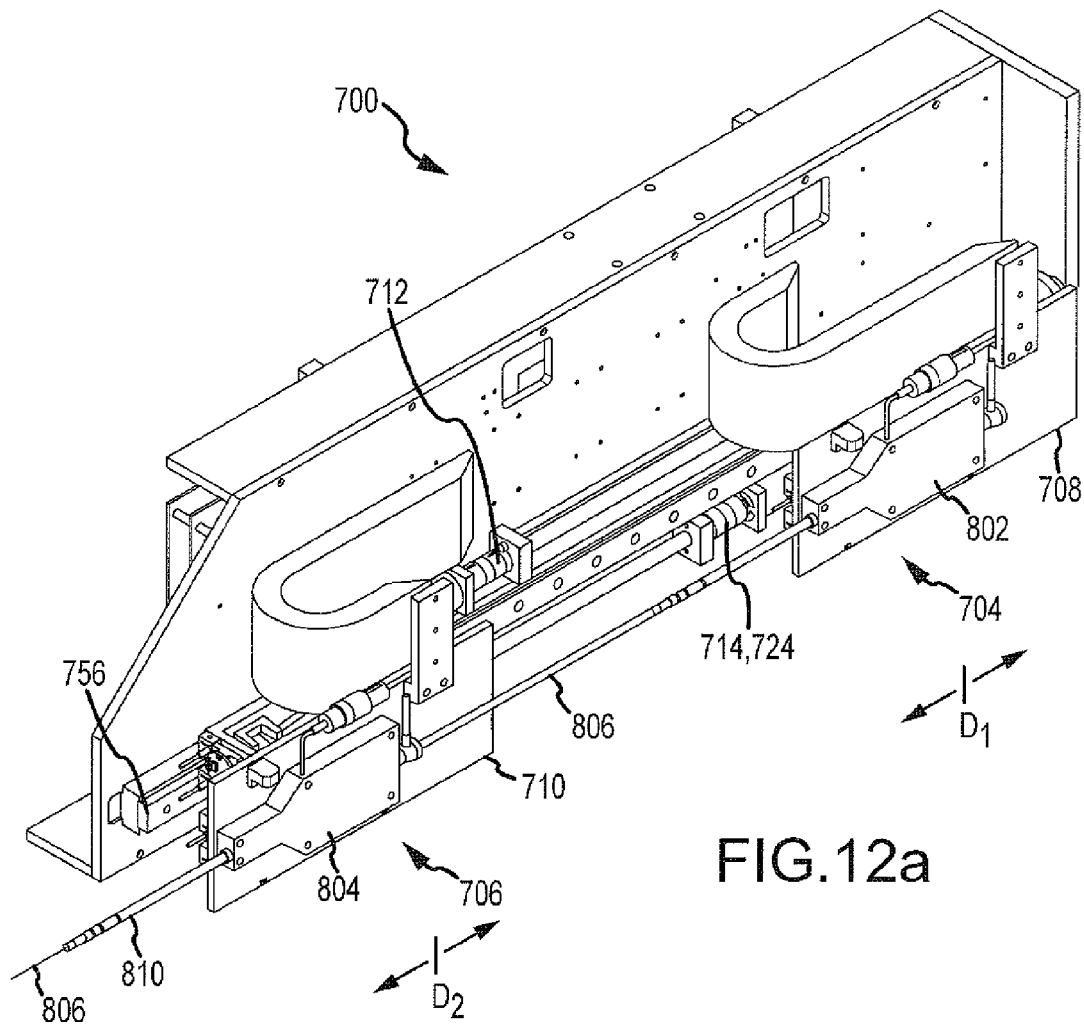
FIGS. 12a-12c are enlarged isometric.
Figure 12B:
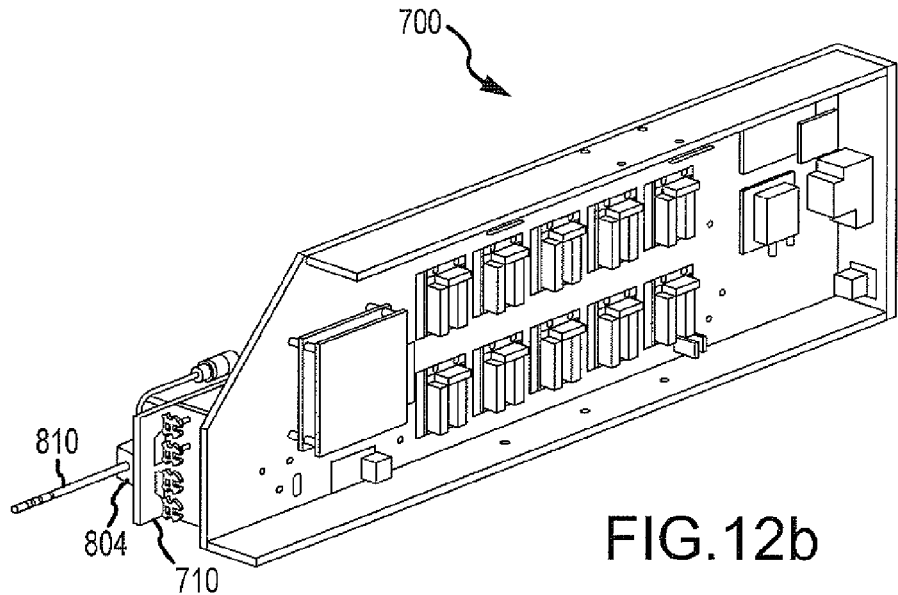
Figure 12C:
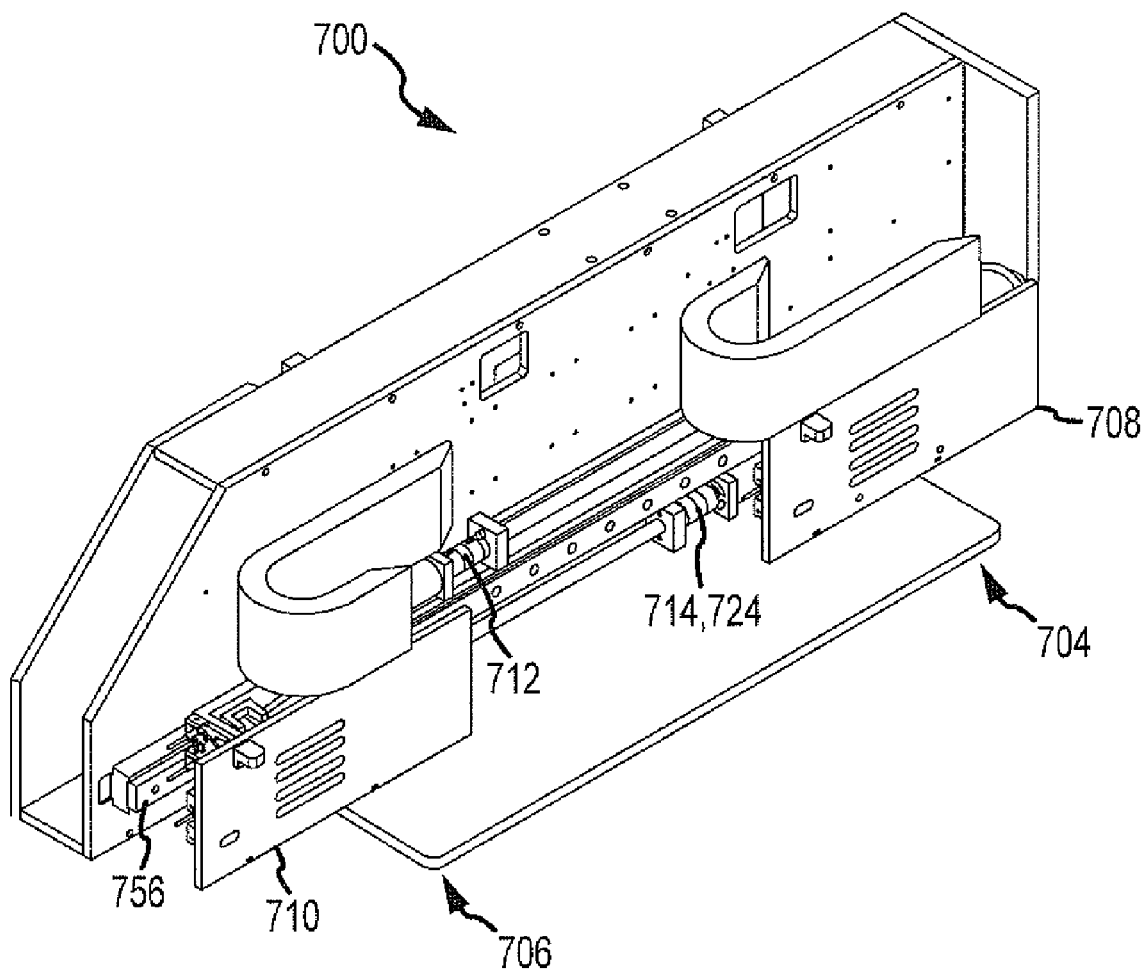
Figure 12H:
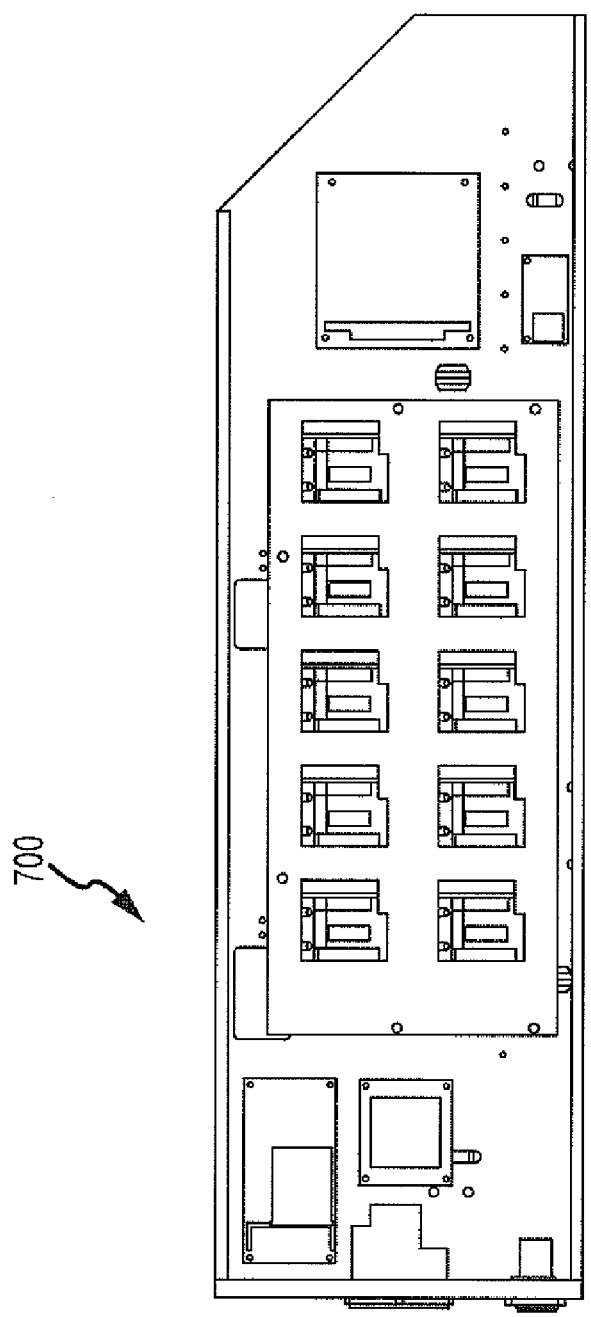
Figure 12I:
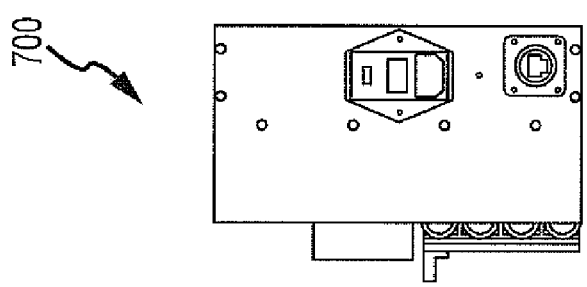
Figure 12K:
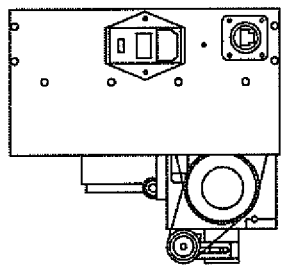
FIGS. 12j-12m are respectively enlarged left side, right side, top and front views of the robotic catheter manipulator assembly of FIG. 12a, illustrating use of the manipulator assembly with a robotic catheter rotatable device cartridge.
Figure 12L:
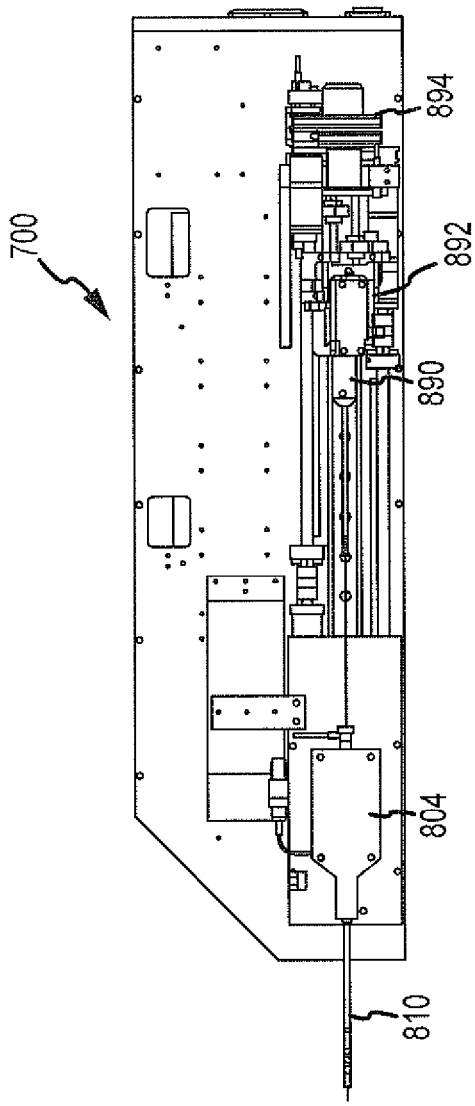

As generally shown in FIGS. 1, 2 and 12a-14e, robotic catheter system 10 which includes one or more robotic catheter manipulator assemblies 300, includes the third embodiment of robotic catheter manipulator assembly 700 including both catheter and sheath manipulation mechanisms 704, 706 for manipulating, for example, a third embodiment of catheter and sheath cartridges 802, 804 (see FIGS. 14a-14e). Manipulator assembly 700 may include interconnected/interlocking manipulation bases 708, 710 for catheter and sheath cartridges 802, 804, and likewise may include electrical "handshake" functionality as discussed below. Each interlocking base 708, 710 may be capable of travel in the longitudinal direction of the catheter/sheath ($D_1$, $D_2$ respectively). In an embodiment, $D_1$ and $D_2$ may each represent a translation of approximately 8 linear inches. As shown in FIG. 12a (similar to the first embodiment of manipulator assembly 302 for FIGS. 3a, 3c and 3e), each interlocking base may be translated by high precision drive mechanisms 712, 714. Such drive mechanisms may include, for example and without limitation, a motor driven lead screw or ball screw (or alternatively, a belt drive, a rolling ring linear drive, or a piezo motor drive).

As shown in FIGS. 12a-12i and 13a-13g, for each cartridge 802, 804, an associated manipulation base 708, 710 may include a plurality of fingers 716, 718, 720 and 722, (e.g., one per steering wire) that extend or protrude upwardly to contact and interact with the steering wire slider blocks (such as slider blocks 812, 814, 816, 818) to independently tension select steering wires 820, 822, 824, 826. Each finger can be configured to be independently actuated by a precision drive mechanism, such as a motor driven ball screw 724 (see also FIGS. 4a-4d and description above for a detailed description of ball screw 324), and may be outfitted with force sensors to measure corresponding steering wire tension. Each motor driven ball screw (for both finger control and cartridge translation control) may further include encoders to measure a relative and/or an absolute position of each element of the system.

Figure 13A:
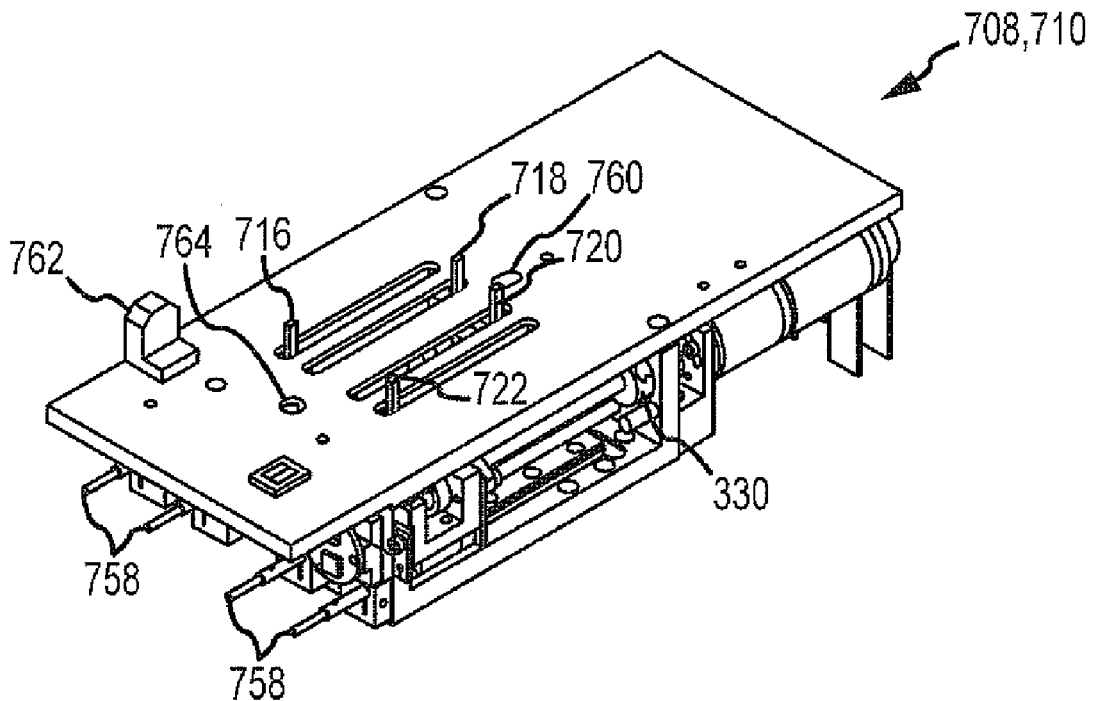
FIGS. 13a-13c are enlarged isometric views.
Figure 13B:
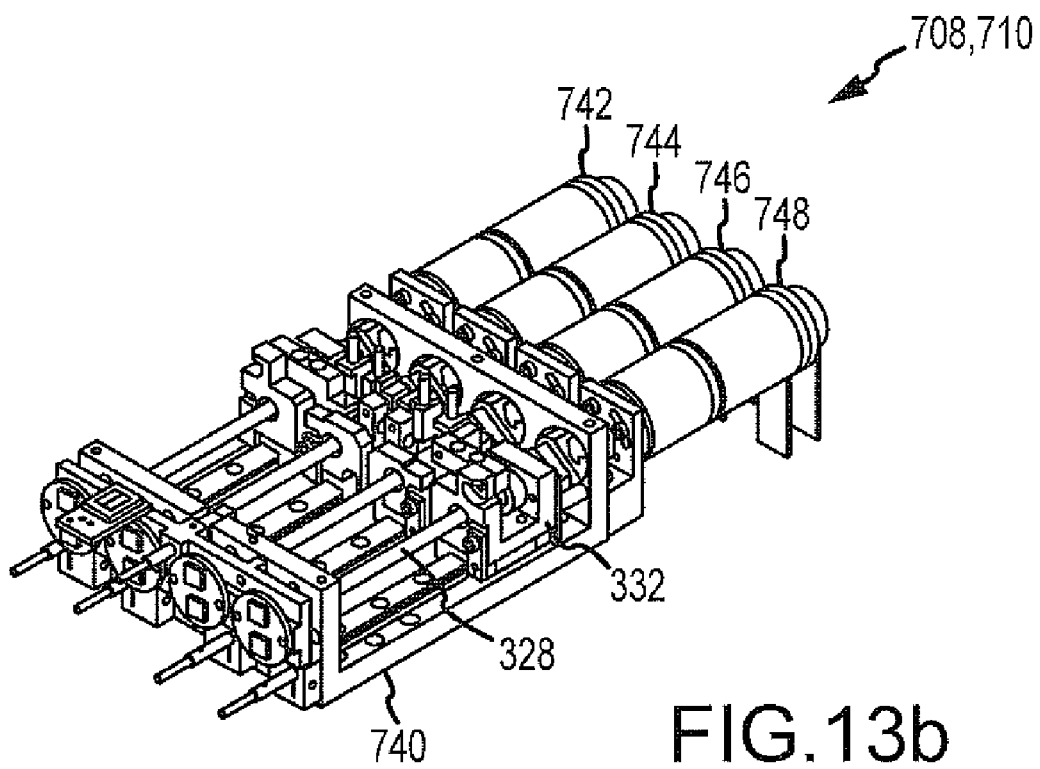
Figure 13C:
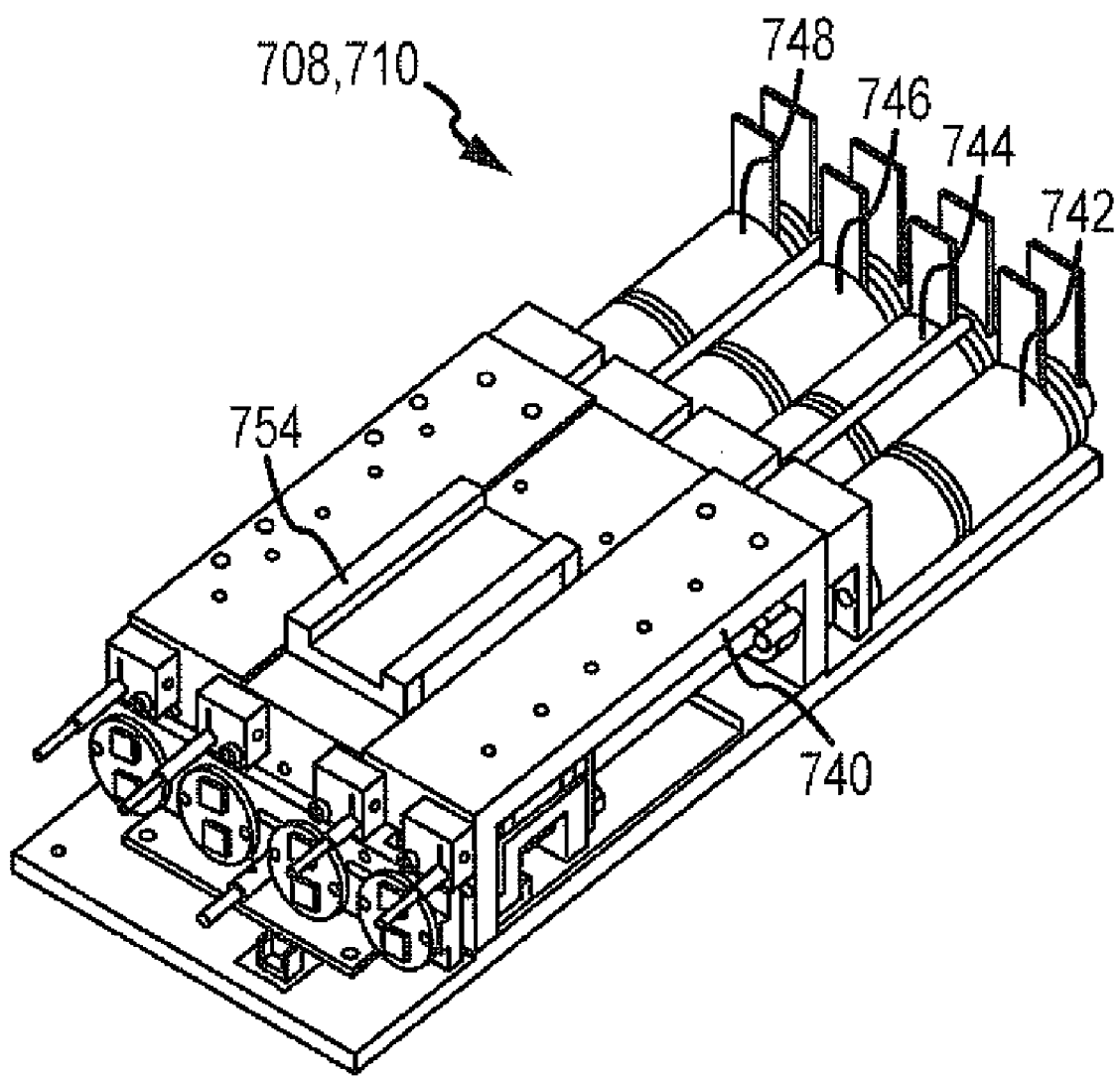
Figure 13D:
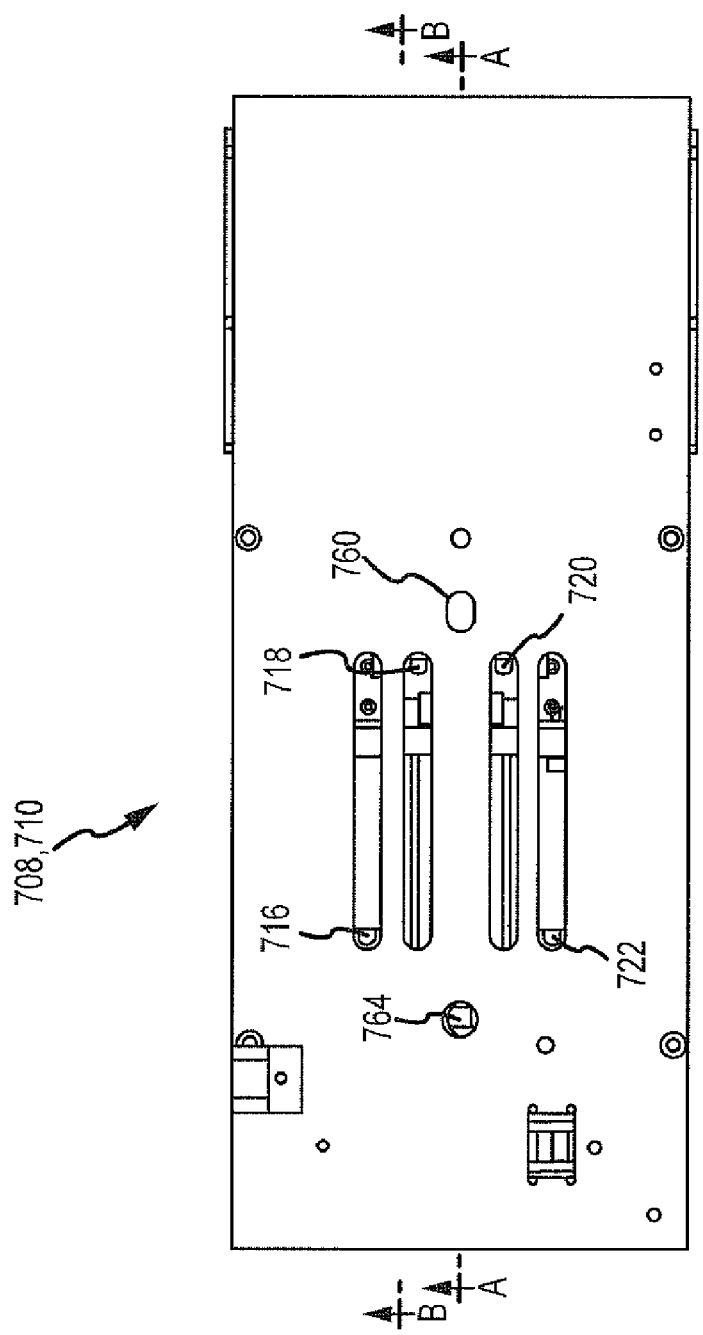
FIGS. 13d-13g are respectively enlarged top and right side, and respectively sections A-A and B-B taken generally along lines A-A and B-B in FIG. 13d, of a third embodiment of a manipulation base.
Figure 13E:
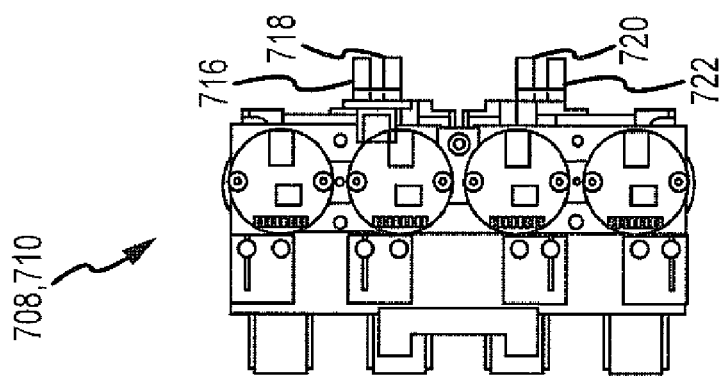
Figure 13F:
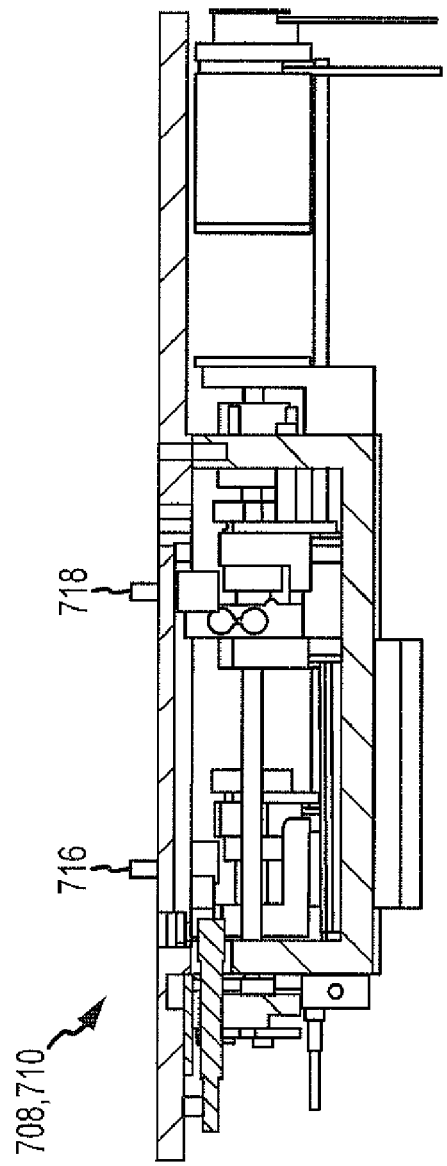
Figure 13G:
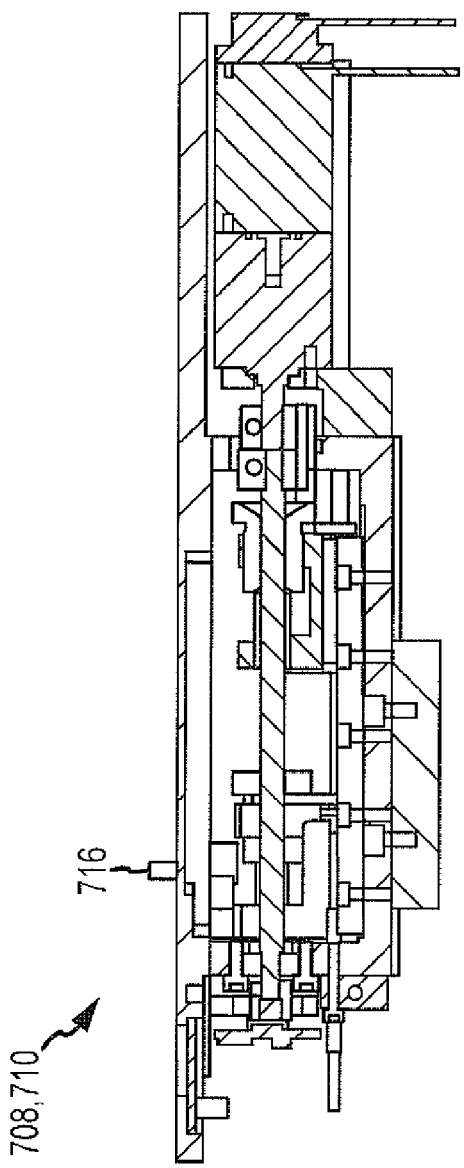

As discussed above, referring to FIGS. 4a-4d, motor driven ball screw 724 (and ball screw 324) may include exemplary components such as motor 326, leadscrew 328, coupler 330, bearing 332, strain gauge 334, radial bearing 336, and bearing 338. As shown in FIG. 13a, bearing 332 and coupler 330 may engage frame 740 (similar to frame 340) of respective bases 708, 710 and a corresponding finger 716, 718, 720 or 722 may be mounted adjacent strain gauge 334 (see FIGS. 4a-4d) for measuring the corresponding steering wire tension.

Referring to FIGS. 13a-13g, bases 708, 710 may include exemplary components such as motors 742, 744, 746 and 748, respectively coupled to fingers 716, 718, 720 and 722. A motor PC board (not shown) and a strain gauge PC board (not shown) may be mounted to frame 740 in a similar manner as bases 308, 310, and a bearing 754 may be provided for sliding of bases 708, 710 on track 756. A plurality of inductive sensors (e.g. home sensors) 758 may be provided for guiding each manipulation base to a safe position.

As with manipulator assembly 302, manipulator assembly 700 may be disposed in a vertical configuration (see FIG. 1) for minimizing both the approach angle of the catheter and the distance the catheter must extend from the patient, or slightly angled from a generally horizontal position (see FIG. 2). In the vertical configuration of FIG. 1, the approach angle and catheter extension distance may be minimized by vertically orienting the backplane of the manipulator head, with the interlocking cartridges positioned at the lower extreme such that they may travel nearly horizontally and substantially in line with the point of entry into the patient (e.g., as generally illustrated in FIG. 1). In such an embodiment, with the backplane of the manipulator head vertically oriented, the positioning of the manipulator head structure may allow the proximal control of the catheter/sheath to be held closely to the patient's body without substantial structural interference. In an embodiment, high-precision drive mechanisms 712, 714 for translating each of the catheter and sheath cartridges 802, 804 may be positioned generally below the manipulator bases 708, 710 to allow the respective cartridges to be positioned toward the lower area of the manipulator. By holding a close distance, the ingress angle of the catheter/sheath may be minimized, and the manipulator control may be positioned more closely to an insertion site.

Figure 12M:
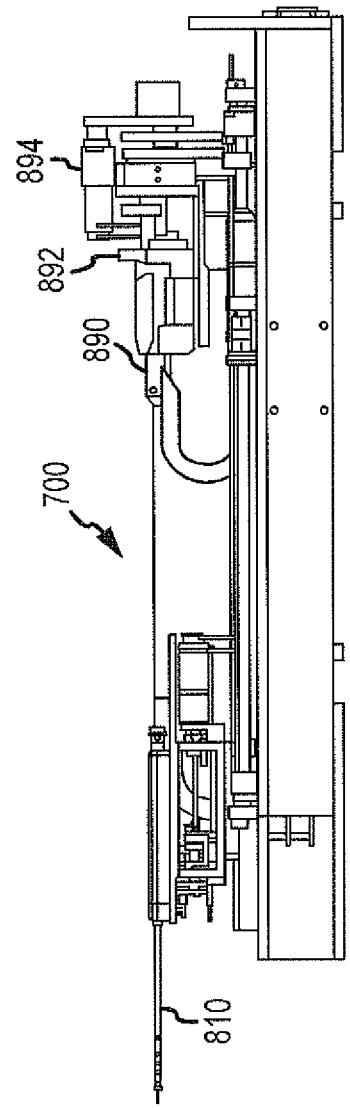
Figure 12J:
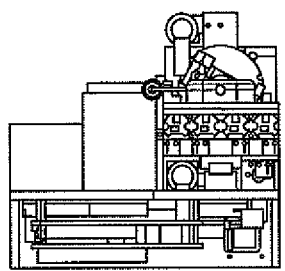

Referring to FIGS. 1, 2 and 12a-12m, particularly FIGS. 12j-12m, the third embodiment of robotic catheter manipulator assembly 700 may be usable with a robotic catheter rotatable device cartridge 890, described in detail in commonly owned and copending application titled "Robotic Catheter Rotatable Device Cartridge." As shown in FIG. 12m, manipulator base 708 may be replaced with a robotic catheter rotatable drive head 892 and a robotic catheter rotatable drive mechanism 894, described in detail in commonly owned and copending application titled "Robotic Catheter Rotatable Drive Mechanism."

Referring to FIGS. 1, 2 and 14a-14e, the third embodiment of catheter and sheath cartridges 802, 804 will be described in detail.

As briefly discussed above, robotic catheter system 10 may include one or more cartridges 400, with the third embodiment of manipulator 700 including at least two cartridges 802, 804, each of which may be respectively designed to control the distal movement of either the catheter or the sheath. With respect to catheter cartridge 802, catheter 806 may be substantially connected or affixed to cartridge 802, so that advancement of cartridge 802 correspondingly advances catheter 806, and retraction of the cartridge retracts the catheter. As further shown in FIGS. 14a-14e and discussed above, in an embodiment, each cartridge 802, 804 may include slider blocks (e.g., 812, 814, 816, 818), each rigidly (and independently) connected or affixed to one of a plurality of catheter steering wires (e.g., 820, 822, 824, 826) in a manner that permits independent tensioning of each steering wire. The cartridge may be provided as a disposable item that is capable of being easily positioned (e.g., snapped) into place in an overall assembly. In an embodiment, as discussed in detail below, the cartridge may include an electrical "handshake" device or component to allow the system to properly identify the cartridge (e.g., by type and/or proper placement/positioning). Sheath cartridge 804 may be designed in a similar manner as the catheter cartridge 802, but will typically be configured to provide for the passage of catheter 806. Assembly 700 may include a plurality (e.g., as many as ten or more) of independent driving mechanisms (e.g. motor driven ball screws 724).

For some embodiments, the catheter and sheath cartridge can be designed to be substantially similar, and in that context a reference to either may relate to both. For example, as shown in FIGS. 14a-14e, the design of the catheter/sheath cartridge may include upper and lower cartridge sections 828, 830, and independent slider blocks 812, 814, 816, 818. The system is not generally limited to specific material selection or formation techniques. However, in an embodiment, the upper and lower cartridge sections 828, 830 may be injection molded using a polycarbonate material. Each slider block 812, 814, 816, 818 may be connected to a separate catheter steering wire 820, 822, 824, 826, and may be formed of a Teflon-like material such as, for example, Delrin AF. When in contact with the cartridge housing portions 828, 830, such Teflon-like slider blocks may maintain a low static and dynamic coefficient of friction and may avoid the need for additional lubrication.

Figure 14A:
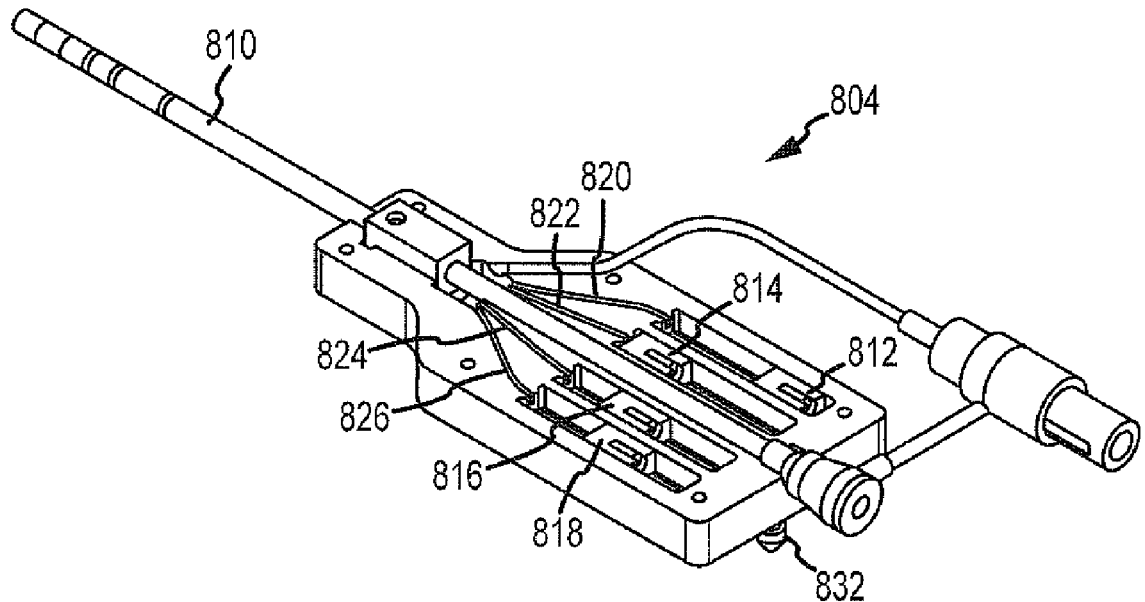
FIGS. 14a-14e are enlarged isometric views of a third embodiment of a robotic catheter device cartridge, with FIG. 12a illustrating an exemplary usage of the robotic catheter device cartridge.
Figure 14B:
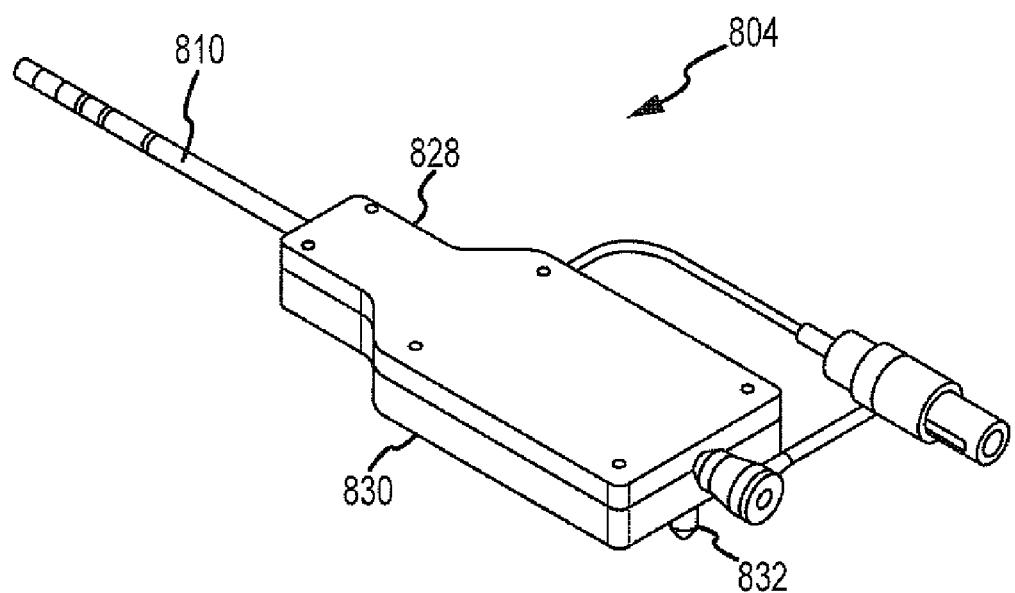
Figure 14C:
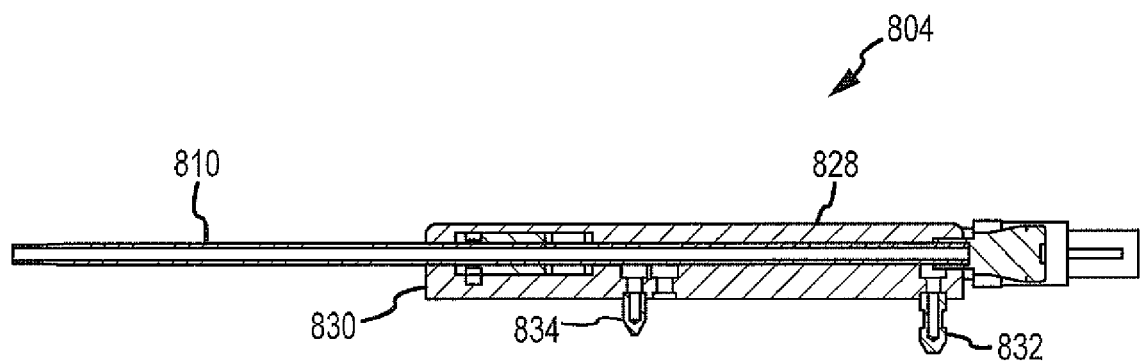
Figure 14D:
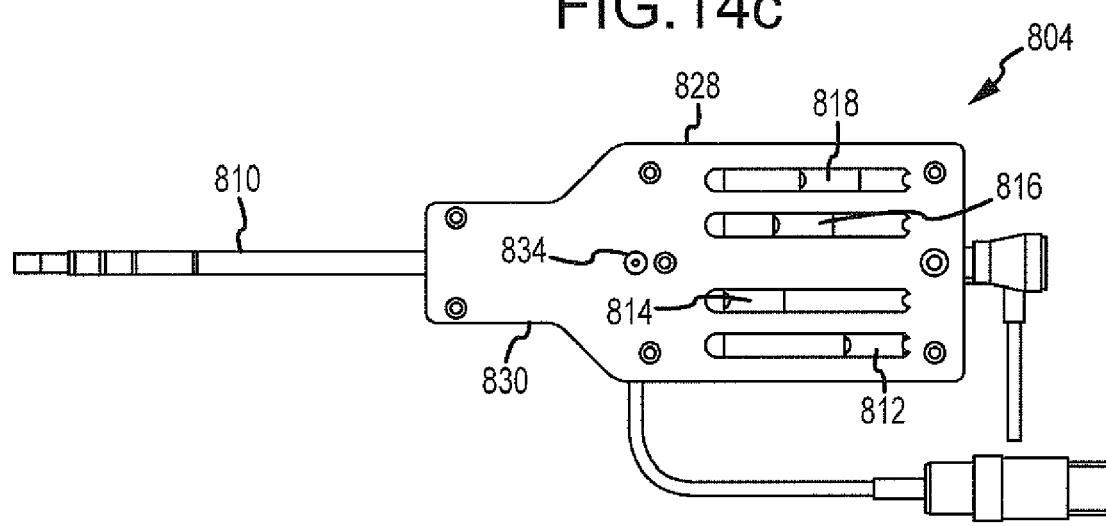
Figure 14E:
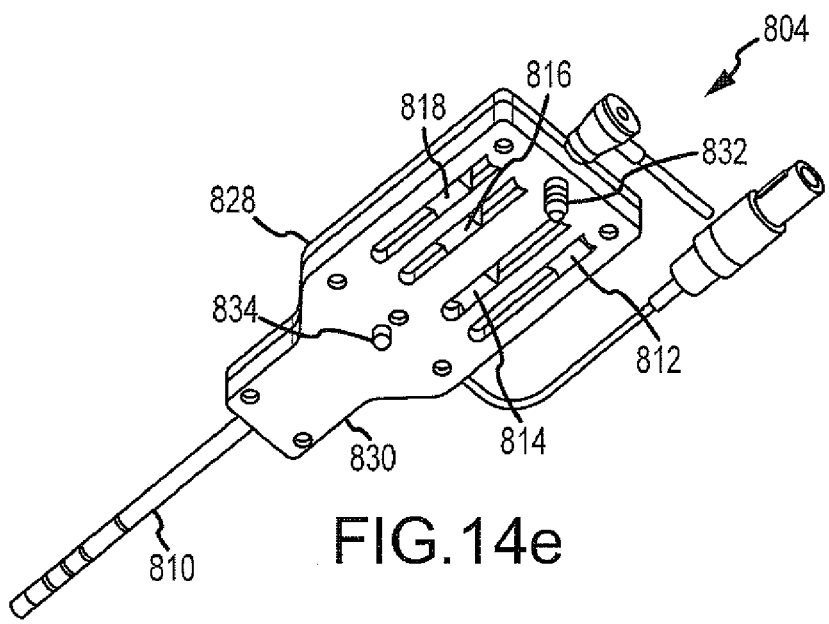
Figure 15A:
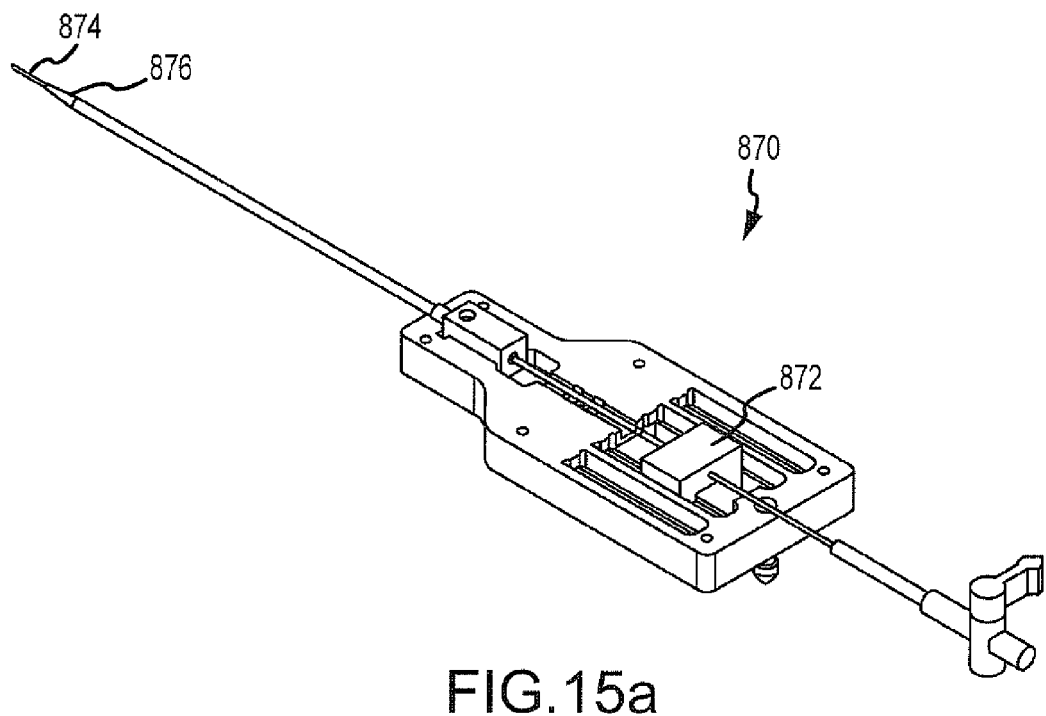
FIGS. 15a-15d are enlarged isometric views of a robotic transseptal device cartridge.
Figure 15B:
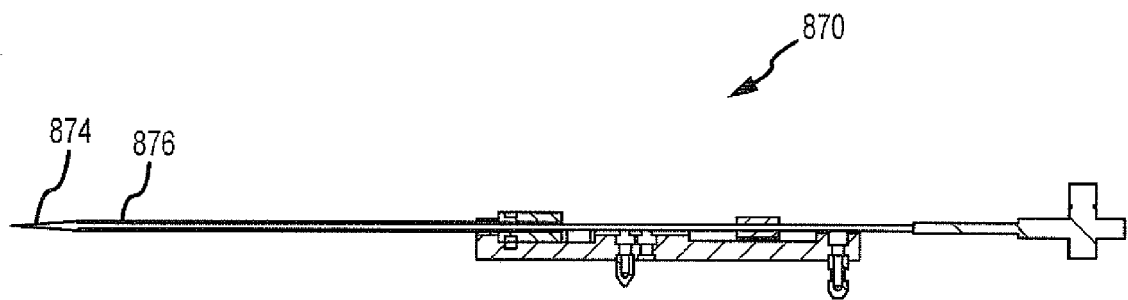
Figure 15C:
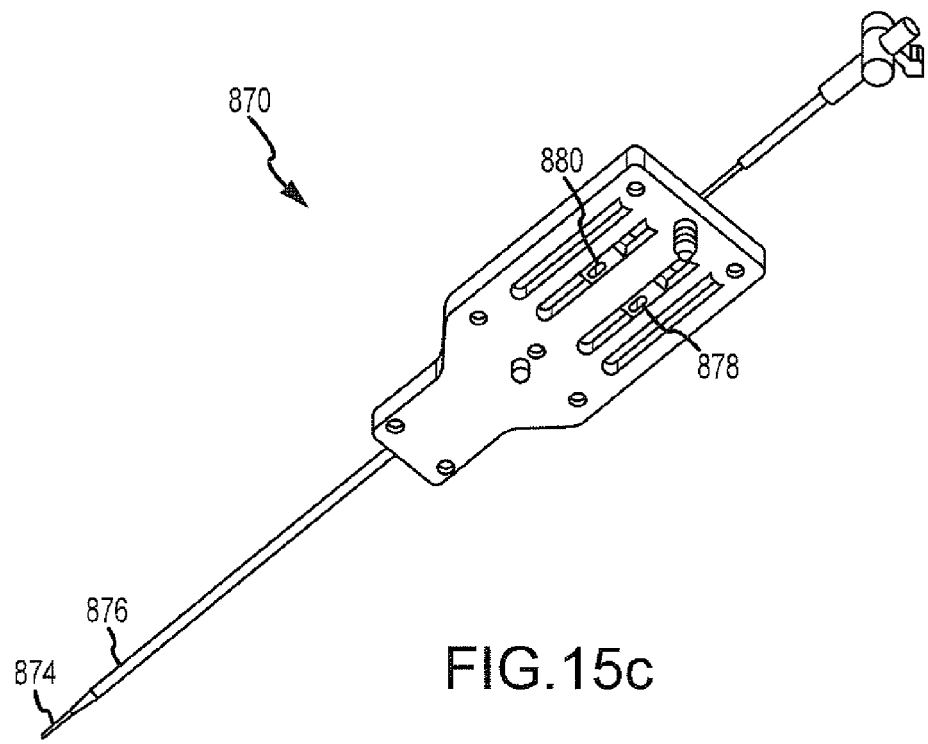
Figure 15D:
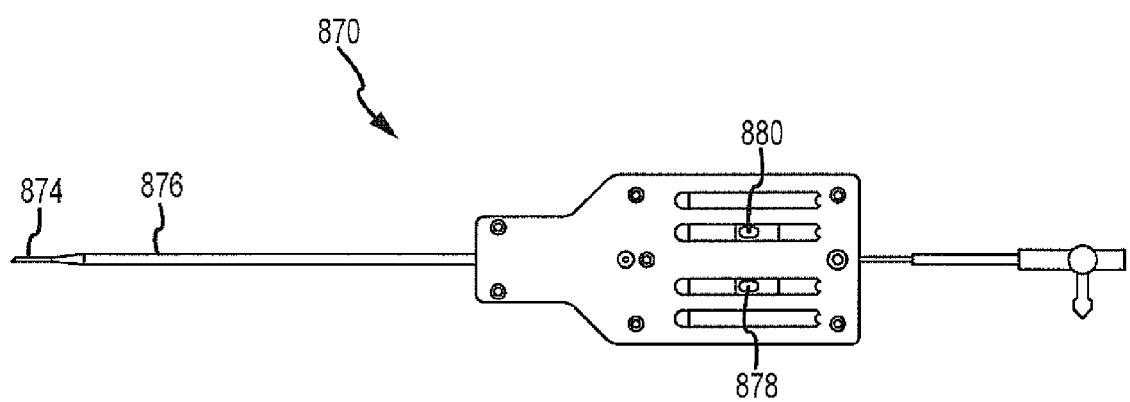

Referring to FIGS. 12a-14e and as discussed above, catheter and sheath cartridges 802, 804 may be configured to secure or lock down onto respective interconnecting catheter and sheath manipulation bases 708, 710. To couple cartridge 802 (and 804) with base 708 (and 710), one or more locking pins (e.g., 832 in FIGS. 14a, 14d and 14e) on the cartridge may engage one or more mating recesses 760 in the base (see FIG. 13a). In an embodiment, such recesses 760 may include an interference lock such as a spring detent or other locking means. In an embodiment, such other locking means may include a physical interference that may require affirmative/positive action by the user to release the cartridge. Such action may include or require actuation of a release lever 762. Additionally, as shown in FIGS. 14c, 14d and 14e, cartridge 802 (and 804) may include one or more locator pins 834 that are configured to passively fit into mating holes on the base (e.g., 764 in FIG. 13a).

In an embodiment, a user (e.g. an EP) may first manually position catheter 806 and sheath 810 (with catheter 806 inserted in sheath 810) within the vasculature of a patient. Once the devices are roughly positioned in relation to the heart, the user may then engage or connect (e.g., "snap-in") the catheter cartridge into place on interconnecting/interlocking bases 708, 710 of manipulator assembly 700, for example, by inserting the locking/locating pins 832, 834 of the cartridges into mating holes 760, 764 of respective base 708, 710. When the cartridge is interconnected with the base, each of the plurality of fingers 716, 718, 720 or 722 may fit into recesses formed between the distal edge of slider blocks 812, 814, 816, 818 and a lower portion of the cartridge housing. Such recesses are shown in, for example, FIGS. 14d and 14e.

Each finger may be designed to be actuated in a proximal direction to correspondingly push each respective slider block. The slider block can be configured to force the finger to self center on its geometry when contact is first made. Such a centering feature may be facilitated by the contact surface of the slider block. For example, as shown in FIGS. 14d and 14e, the slider block may include an engagement surface (e.g., shaped as a semi-cylindrical recess in the forward facing portion). This surface may be configured to mate or communicate with a matching round portion of a corresponding finger.

With sufficiently rigid coupling between each slider block and a corresponding steering wire, pushing a slider block in a proximal direction may cause an attached steering wire to tension and thus laterally deflect the distal end of the catheter and sheath 806, 810. Moreover, in such an embodiment, because there is no rigid connection between each finger and its associated slider block, the manipulator assembly 700 cannot pull the steering wire in a forward direction. That is, when each block is actuated, it is only possible to tension the steering wire. Furthermore, because the push-actuation of each slider block occurs near that block's bottom surface, a moment may be imposed on the block. Because such a moment may increase the likelihood of the block binding during travel, the length of the block may be optimized to reduce or minimize contact forces between the block and the cartridge housing.

The generally linear architecture of manipulation bases and cartridges described herein (including the embodiments discussed below) allows for integrated force sensors on the control elements, thus facilitating active tensioning and allowing for a "watchdog" system to limit movements that may overstress a catheter. Further, as illustrated, the cartridges may be placed on or removed from the manipulator assemblies at any time without jamming, regardless of the position of the manipulation bases. This is readily possible due to the configuration of the control fingers discussed herein that generally approach the cartridges from the de-tensioned side, and further, the home position of the manipulation bases may be designed outside of the cartridge slide block operating range.

Referring to FIGS. 1, 2, 12a-12i and 15a-15d, an embodiment of a transseptal dilator cartridge 870 will be described in detail.

Robotic catheter system 10 may be designed to operate with a variety of traditional catheter tools presently available to electrophysiologists. An example of a tool that may be configured to work with catheter manipulation base 708 is a transseptal needle/dilator. As shown in FIGS. 15a-15d, the design of this transseptal dilator cartridge 870 may include a dual-actuated slider block 872, that may be pushed in a distal direction to actuate a transseptal needle 874. In an embodiment, the system may navigate the surrounding sheath into a proper position and angle near the fossa ovalis. The rearward carriage holding the transseptal dilator cartridge 870 could then translate in a distal direction to extend the tool beyond the sheath opening. Upon actuation of slider block 872, needle 874 can extend from its retracted state within dilator 876 and puncture the septum. The rearward cartridge could then advance further so dilator 876 may expand the puncture site.

In an embodiment, to actuate slider block 872, the fingers (e.g., shown as 718, 720 in FIG. 13a) of the manipulator may operate in a distal direction to cause slider block 872 to move distally. Cartridge 870 may be connected and locked into place on the interconnecting base, and the fingers can then be configured to fit into recesses 878, 880 in slider block 872. With such an embodiment, needle 874 can be extended/actuated when manipulator fingers 718, 720 move slider 872 (and attached needle 874) in a distal direction. It may likewise be retracted into dilator 876 when slider 872 is moved in a proximal direction. In such an embodiment, the slider may be "actively" moved both distally and proximally to extend and retract the needle, respectively.

In a further embodiment, the fingers 718, 720 of the manipulator may actuate needle 874 by pushing slider block 872 in a proximal direction (similar to the actuation of a catheter steering wire). This rearward motion, however, may then be reversed by a pulley mechanism (not shown) to then extend needle 874 beyond the dilator 876. While this design may require a more complex cartridge, the operation of the manipulator could remain the same as with other steering wire control (e.g., actuation through rearward motion).

Referring to FIGS. 1, 2 and 16a-19i, a fourth embodiment of robotic catheter manipulator assembly 900 will be described in detail.

Figure 16A:
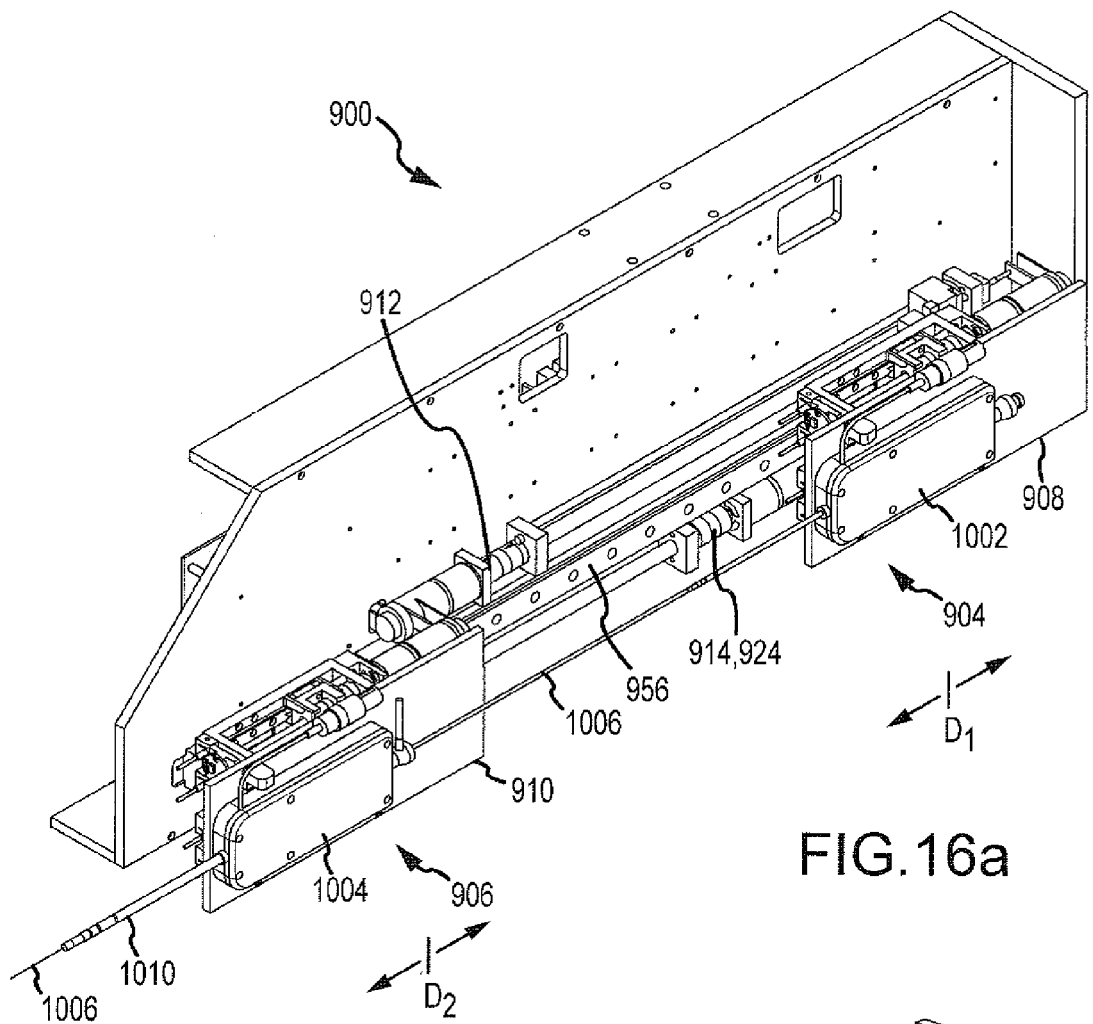
FIGS. 16a-16c are enlarged isometric.

As generally shown in FIGS. 1, 2, 16a-16i and 17a-19i robotic catheter system 10 which includes one or more robotic catheter manipulator assemblies 300, includes the fourth embodiment of robotic catheter manipulator assembly 900 including both catheter and sheath manipulation mechanisms 904, 906 for manipulating, for example, a fourth embodiment of catheter and sheath cartridges 1002, 1004. Manipulator assembly 900 may include interconnected/interlocking manipulation bases 908, 910 for catheter and sheath cartridges 1002, 1004, and likewise may include electrical "handshake" functionality as discussed below. Each interlocking base 908, 910 may be capable of travel in the longitudinal direction of the catheter/sheath ($D_1$, $D_2$ respectively). In an embodiment, $D_1$ and $D_2$ may each represent a translation of approximately 8 linear inches. As shown in FIG. 16a (similar to the first to third embodiments of manipulator assemblies 302, 500, 700), each interlocking base may be translated by high precision drive mechanisms 912, 914. Such drive mechanisms may include, for example and without limitation, a motor driven lead screw or ball screw (or alternatively, a belt drive, a rolling ring linear drive, or a piezo motor drive).

As shown in FIGS. 16a-16i and 17a-19i, for each cartridge 1002, 1004, an associated manipulation base 908, 910 may include a plurality of slider blocks 916, 918, 920 and 922, (e.g., one per steering wire) that extend up to the surface of base plate 923 and are contacted by steering wire fingers 1012, 1014, 1016, 1018 to independently tension select steering wires 1020, 1022, 1024, 1026. Each finger can be configured to be independently actuated by a precision drive mechanism, such as a motor driven ball screw 924 (see also FIGS. 4a-4d and description above for a detailed description of ball screw 324), and may be outfitted with force sensors to measure corresponding steering wire tension. Each motor driven ball screw (for both finger control and cartridge translation control) may further include encoders to measure a relative and/or an absolute position of each element of the system.

Figure 17A:
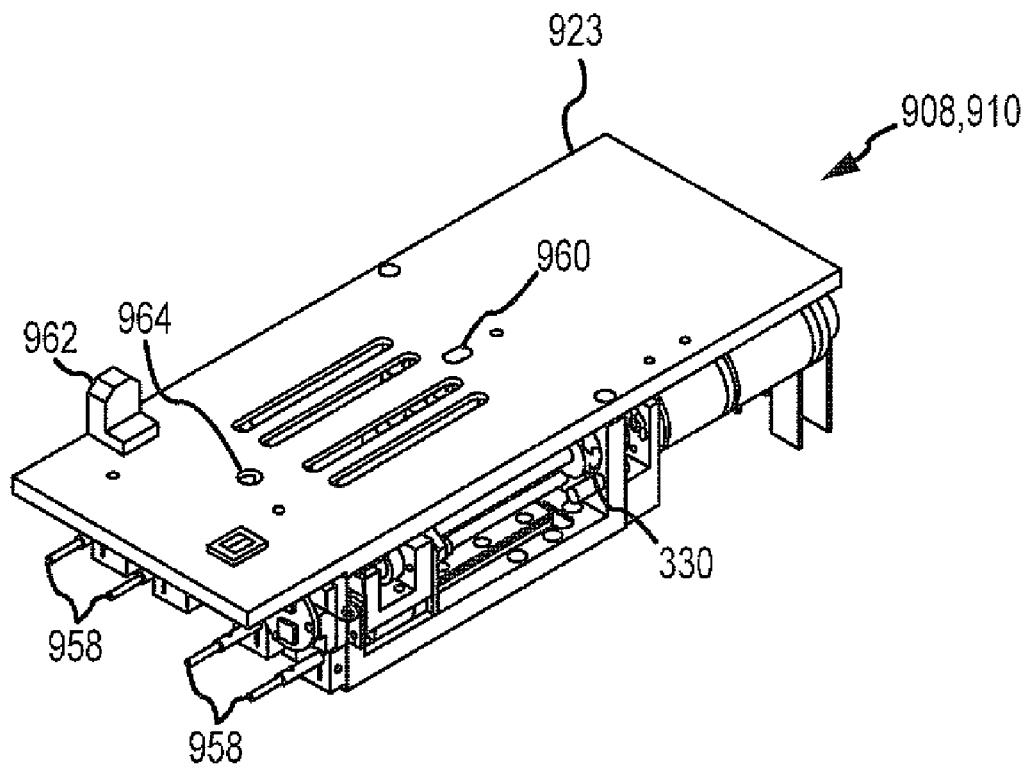
FIGS. 17a-17c are enlarged isometric views.

As discussed above, referring to FIGS. 4a-4d, motor driven ball screw 924 (and ball screw 324) may include exemplary components such as motor 326, leadscrew 328, coupler 330, bearing 332, strain gauge 334, radial bearing 336, and bearing 338. As shown in FIG. 17a, bearing 332 and coupler 330 may engage frame 940 (similar to frame 340) of bases 908, 910 and corresponding slider blocks 916, 918, 920 or 922 may be mounted adjacent strain gauge 334 (see FIGS. 4a-4d) for measuring the corresponding steering wire tension.

Referring to FIGS. 17a-17g, bases 908, 910 may include exemplary components such as motors 942, 944, 946 and 948, respectively coupled to slider blocks 916, 918, 920 and 922. A motor PC board (not shown) and a strain gauge PC board (not shown) may be mounted to frame 940 in a similar manner as bases 308, 310 (see FIGS. 5a-5c), and a bearing 954 may be provided for sliding of bases 908, 910 on track 956. A plurality of inductive sensors (e.g. home sensors) 958 may be provided for guiding each manipulation base to a safe position.

Figure 16B:
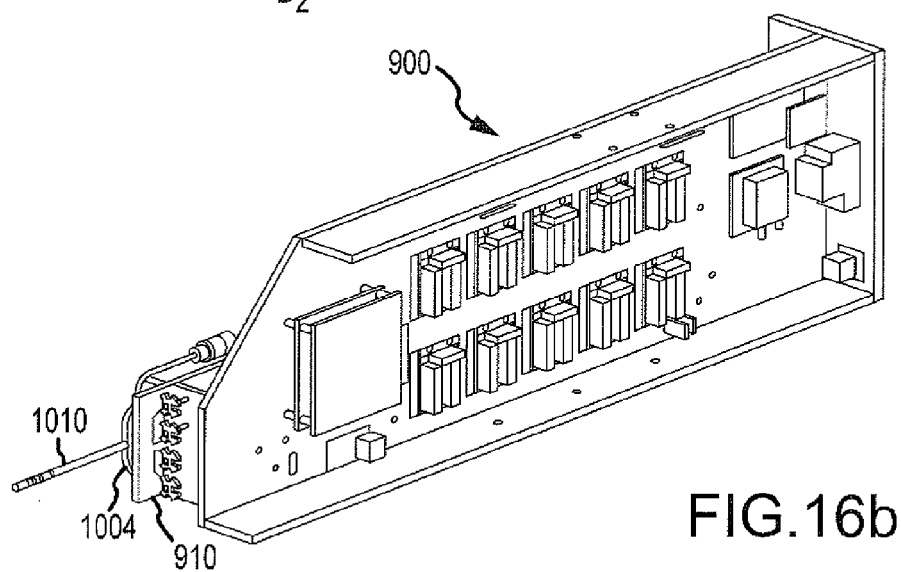
Figure 16C:
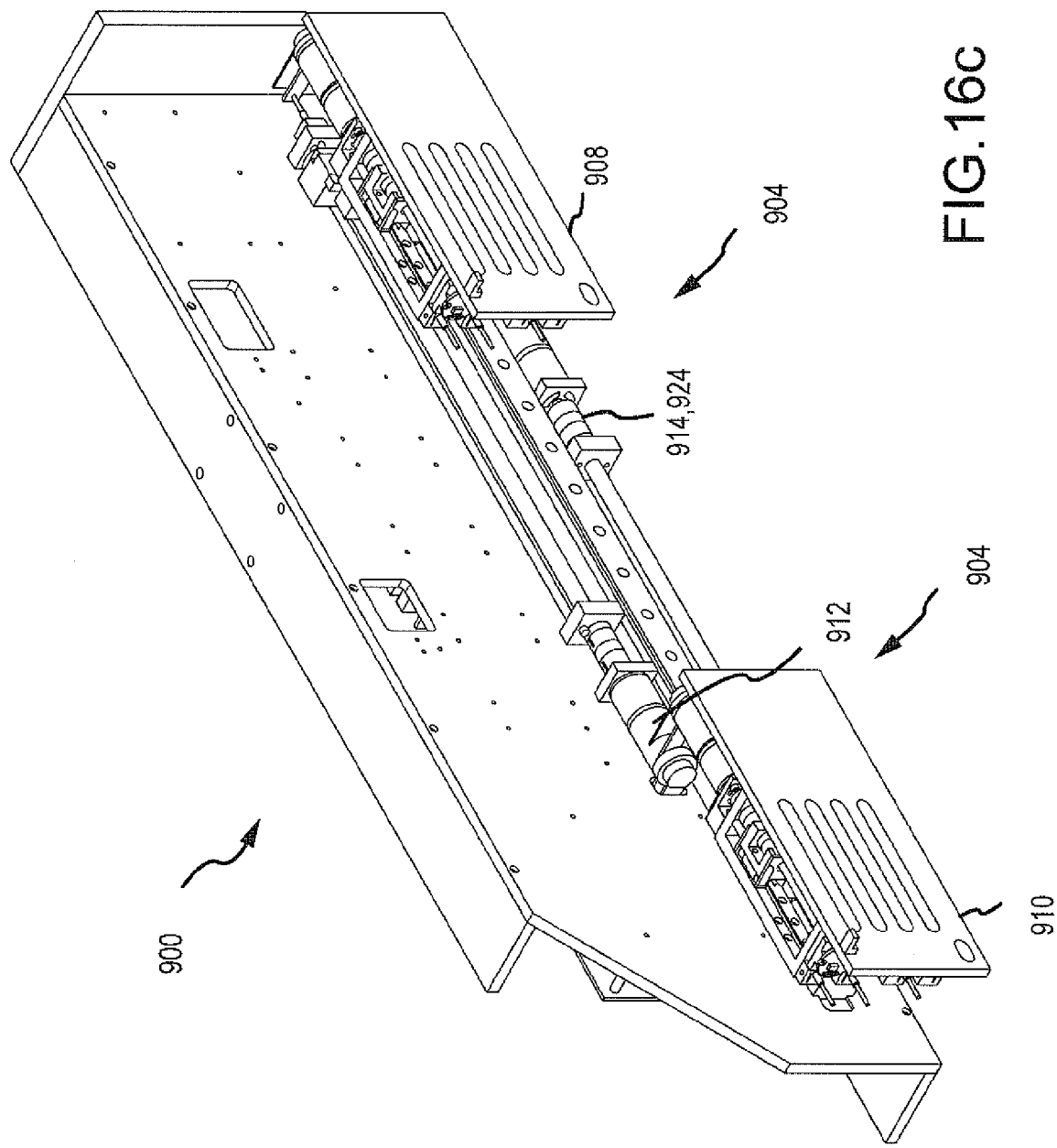
Figure 16E:
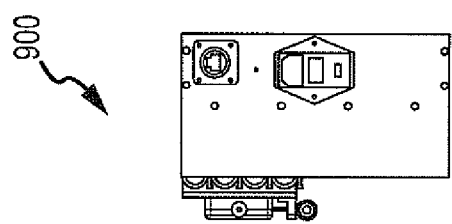
FIGS. 16d-16i are respectively enlarged left side, right side, top, front, back and a corresponding left side view of a fourth embodiment of a robotic catheter manipulator assembly.
Figure 16F:
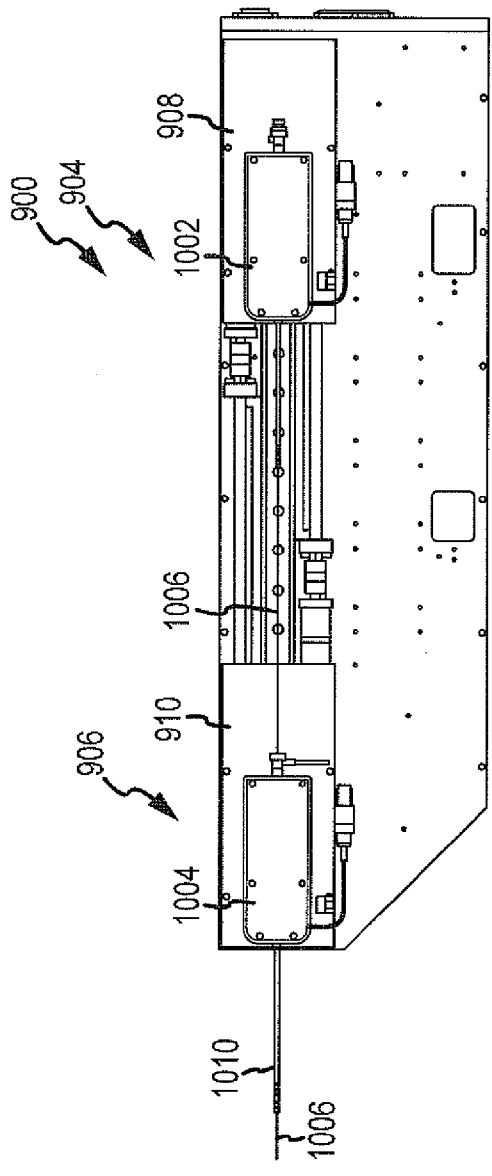
Figure 16G:
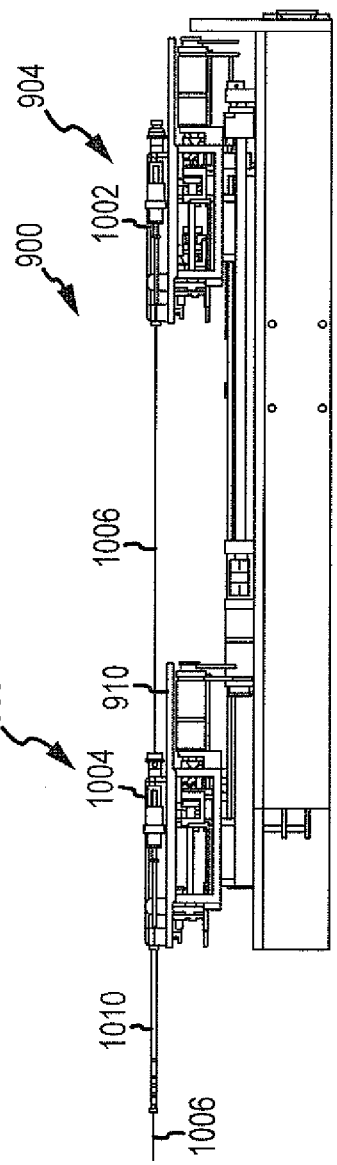
Figure 16D:
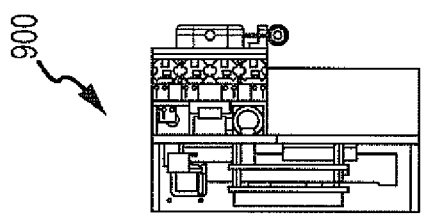
Figure 16H:
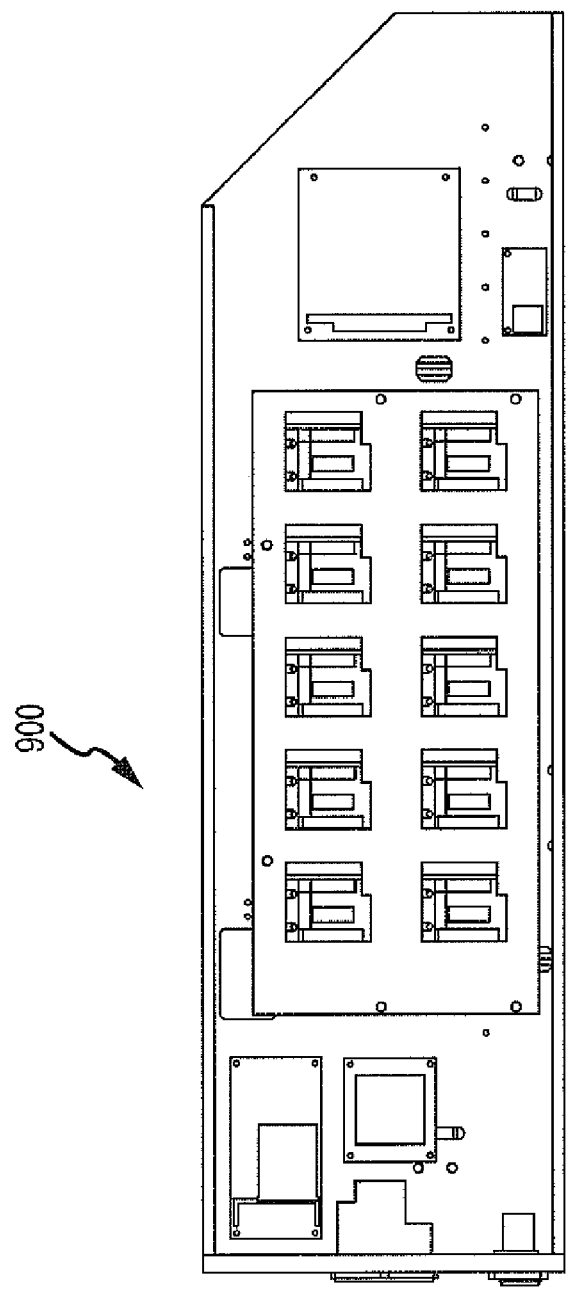
Figure 16I:
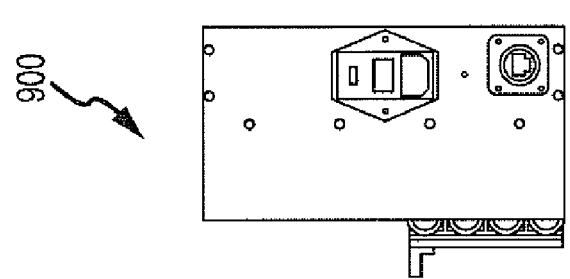
Figure 16K:
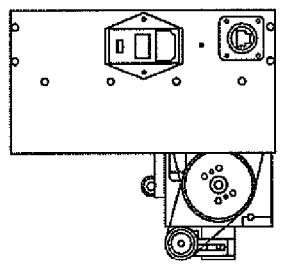
FIGS. 16j-16m are respectively enlarged left side, right side, top and front views of the robotic catheter manipulator assembly of FIG. 16a, illustrating use of the manipulator assembly with a robotic catheter rotatable device cartridge.
Figure 16L:
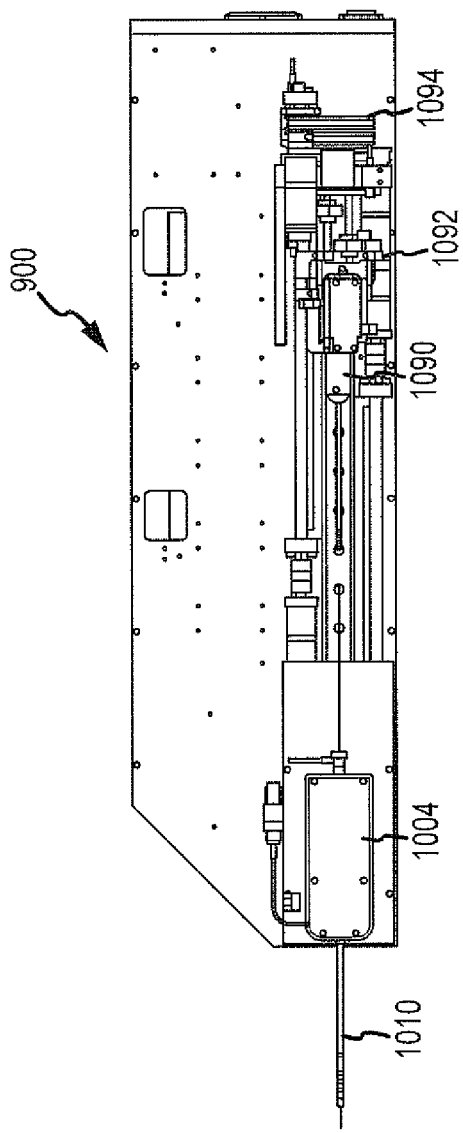
Figure 16J:
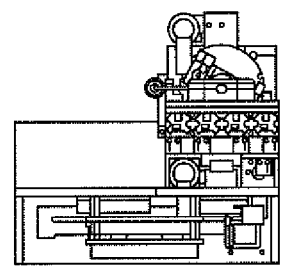

As with manipulator assembly 302, manipulator assembly 900 may be disposed in a vertical configuration (see FIG. 1) for minimizing both the approach angle of the catheter and the distance the catheter must extend from the patient, or slightly angled from a generally horizontal position (see FIG. 2). In the vertical configuration of FIG. 1, the approach angle and catheter extension distance may be minimized by vertically orienting the backplane of the manipulator head, with the interlocking cartridges positioned at the lower extreme such that they may travel nearly horizontally and substantially in line with the point of entry into the patient (e.g., as generally illustrated in FIG. 1). In such an embodiment, with the backplane of the manipulator head vertically oriented, the positioning of the manipulator head structure may allow the proximal control of the catheter/sheath to be held closely to the patient's body without substantial structural interference. In an embodiment, high-precision drive mechanisms 912, 914 for translating each of the catheter and sheath cartridges 1002, 1004 may be positioned generally below manipulator bases 908, 910 to allow the respective cartridges to be positioned toward the lower area of the manipulator. By holding a close distance, the ingress angle of the catheter/sheath may be minimized, and the manipulator control may be positioned more closely to an insertion site. Further, as shown in FIG. 16b, all electronics may be disposed on the back side of manipulator assembly 900 to render assembly 900 generally self contained, requiring only power and communication wires to be connected thereto.

Figure 16M:
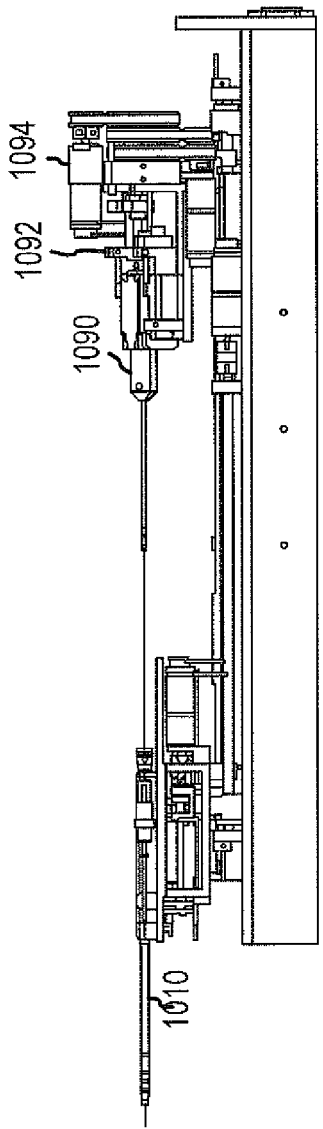

Referring to FIGS. 1, 2 and 16a-16m, particularly FIGS. 16j-16m, the fourth embodiment of robotic catheter manipulator assembly 900 may be usable with a robotic catheter rotatable device cartridge 1090, described in detail in commonly owned and copending application titled "Robotic Catheter Rotatable Device Cartridge." As shown in FIG. 16m, manipulator base 908 may be replaced with a robotic catheter rotatable drive head 1092 and a robotic catheter rotatable drive mechanism 1094, described in detail in commonly owned and copending application titled "Robotic Catheter Rotatable Drive Mechanism."

Referring to FIGS. 1, 2 and 16a-19i, the fourth embodiment of catheter and sheath cartridges 1002, 1004 will be described in detail.

As briefly discussed above, robotic catheter system 10 may include one or more cartridges 400, with the fourth embodiment of manipulator 900 including at least two cartridges 1002, 1004, each of which may be respectively designed to control the distal movement of either the catheter or the sheath. With respect to catheter cartridge 1002, catheter 1006 may be substantially connected or affixed to cartridge 1002, so that advancement of cartridge 1002 correspondingly advances catheter 1006, and retraction of the cartridge retracts the catheter. As further shown in FIGS. 18a-19i and discussed above, in an embodiment, each cartridge 1002, 1004 may include steering wire fingers 1012, 1014, 1016, 1018, each rigidly (and independently) connected or affixed to one of a plurality of catheter steering wires (e.g., 1020, 1022, 1024, 1026) in a manner that permits independent tensioning of each steering wire. The cartridge may be provided as a disposable item that is capable of being easily positioned (e.g., snapped) into place in an overall assembly. In an embodiment, as discussed in detail below, the cartridge may include an electrical "handshake" device or component to allow the system to properly identify the cartridge (e.g., by type and/or proper placement/positioning). Sheath cartridge 1004 may be designed in a similar manner as catheter cartridge 1002, but will typically be configured to provide for the passage of catheter 1006. Manipulator assembly 902 may include a plurality (e.g., as many as ten or more) of independent driving mechanisms (e.g. motor driven ball screws 924).

For some embodiments, the catheter and sheath cartridges can be designed to be substantially similar, and in that context a reference to either may relate to both. For example, as shown in FIGS. 18a-19i, the design of the catheter/sheath cartridges may include upper and lower cartridge sections 1028, 1030, and independent steering wire fingers 1012, 1014, 1016, 1018. The system is not generally limited to specific material selection or formation techniques. However, in an embodiment, the upper and lower cartridge sections 1028, 1030 may be injection molded using a polycarbonate material. Each steering wire finger 1012, 1014, 1016, 1018 via its slider 1019 may be connected to a separate catheter steering wire 1020, 1022, 1024, 1026, and may be formed of a Teflon-like material such as, for example, Delrin AF. When in contact with the cartridge housing portions 1028, 1030, such Teflon-like sliders 1019 and steering wire fingers may maintain a low static and dynamic coefficient of friction and may avoid the need for additional lubrication.

Referring to FIGS. 18a-19i, catheter and sheath cartridges 1002, 1004 may be configured to secure or lock down onto respective interconnecting catheter and sheath manipulation bases 908, 910. To couple cartridge 1002 (and 1004) with base 908 (and 910), one or more locking pins (e.g., 1032 in FIGS. 18e, 19h) on the cartridge may engage one or more mating recesses 960 in the base (see FIG. 17a). In an embodiment, such recesses 960 may include an interference lock such as a spring detent or other locking means. In an embodiment, such other locking means may include a physical interference that may require affirmative/positive action by the user to release the cartridge. Such action may include or require actuation of a release lever 962. Additionally, as shown in FIGS. 18e and 19h, cartridge 1002 (and 1004) may include one or more locator pins 1034 that are configured to passively fit into mating holes on the base (e.g., 964 in FIG. 17a).

In an embodiment, a user (e.g. an EP) may first manually position catheter 1006 and sheath 1010 (with catheter 1006 inserted in sheath 1010) within the vasculature of a patient. Once the devices are roughly positioned in relation to the heart, the user may then engage or connect (e.g., "snap-in") the catheter cartridge into place on interconnecting/interlocking bases of a manipulator, for example, by inserting the locking/locating pins 1032, 1034 of the cartridge into mating holes 960, 964 of manipulation bases 908, 910. When the cartridge is interconnected with the base, each of the plurality of steering wire fingers 1012, 1014, 1016, 1018 may fit into recesses formed at the distal edge of slider blocks 916, 918, 920, 922. Such recesses are shown in, for example, FIG. 17b.

Figure 17B:
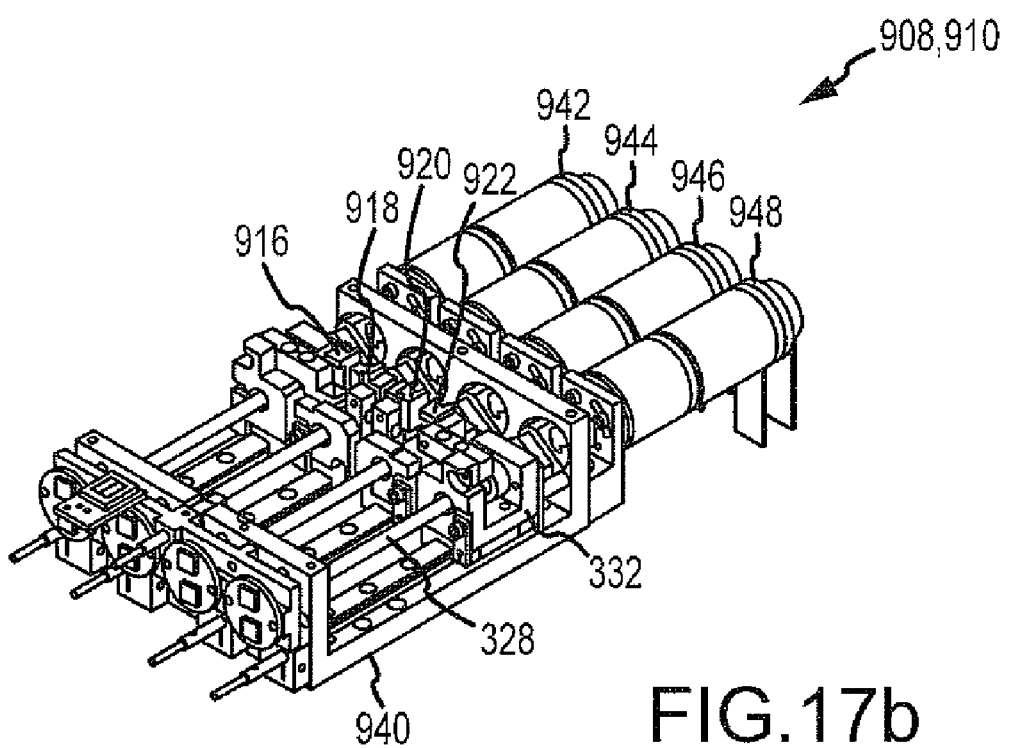
Figure 17C:
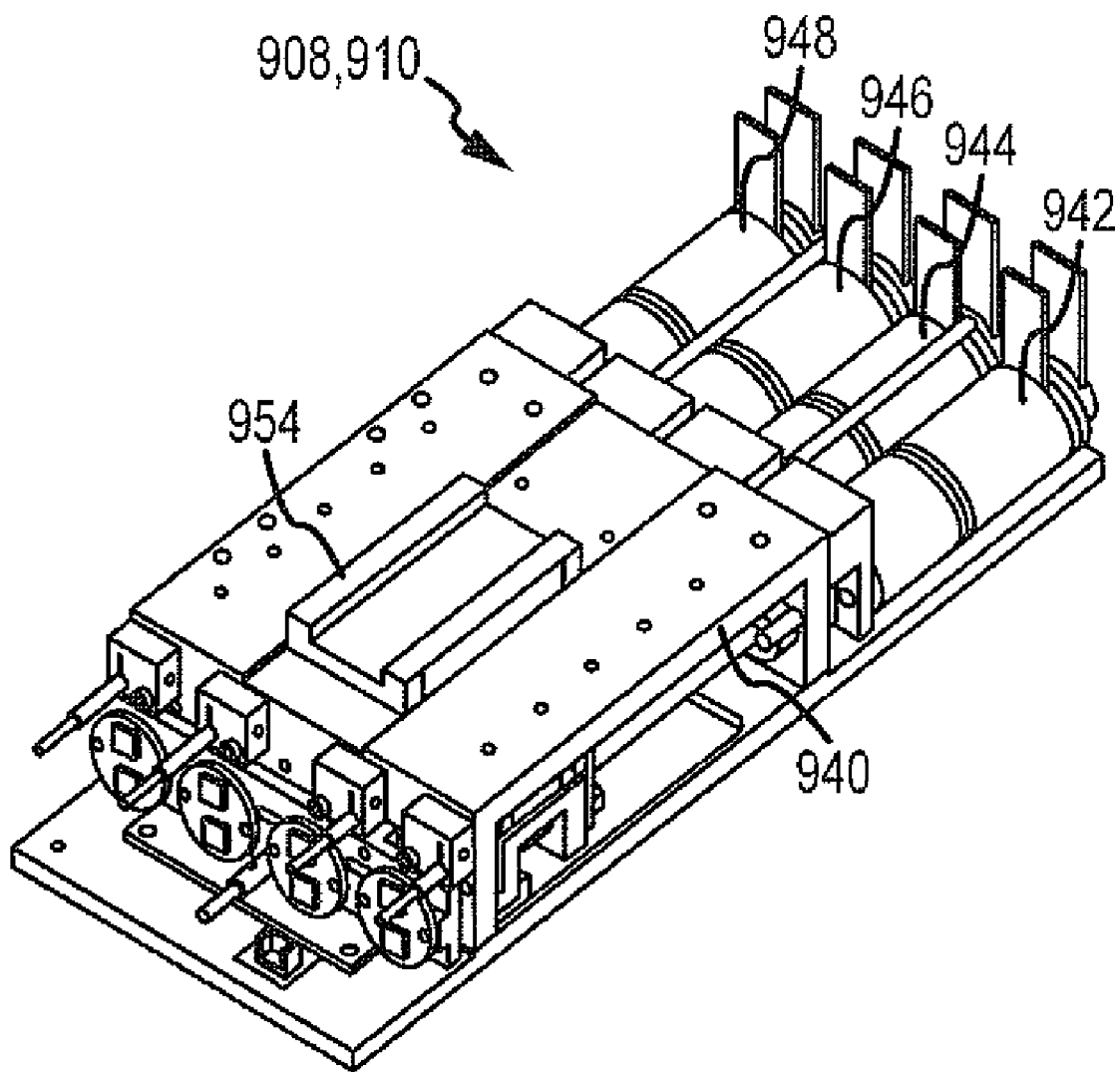
Figure 17D:
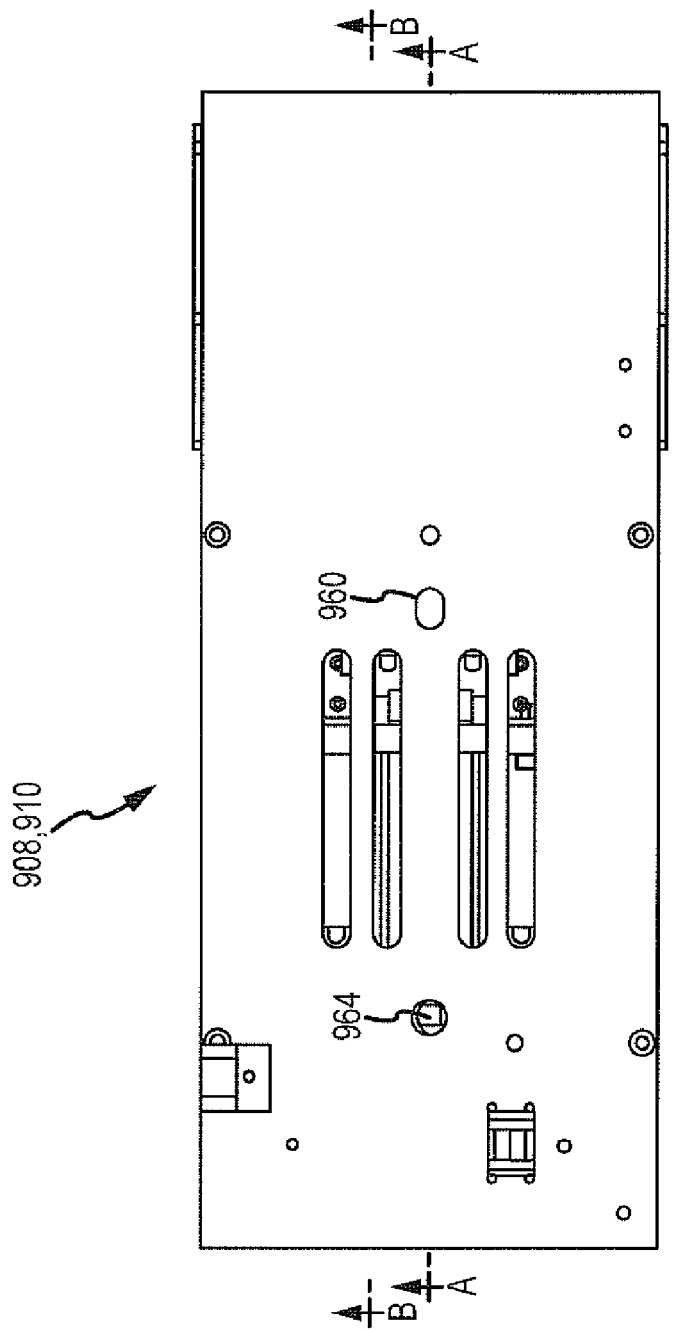
Figure 17E:
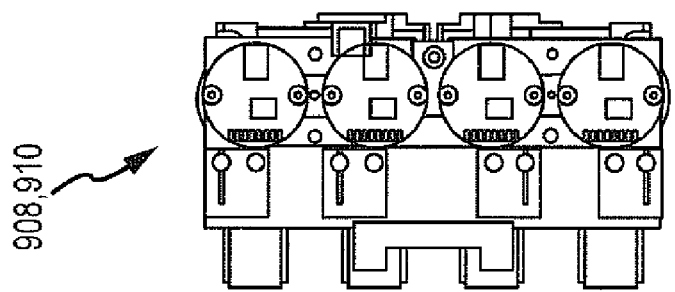
Figure 18A:
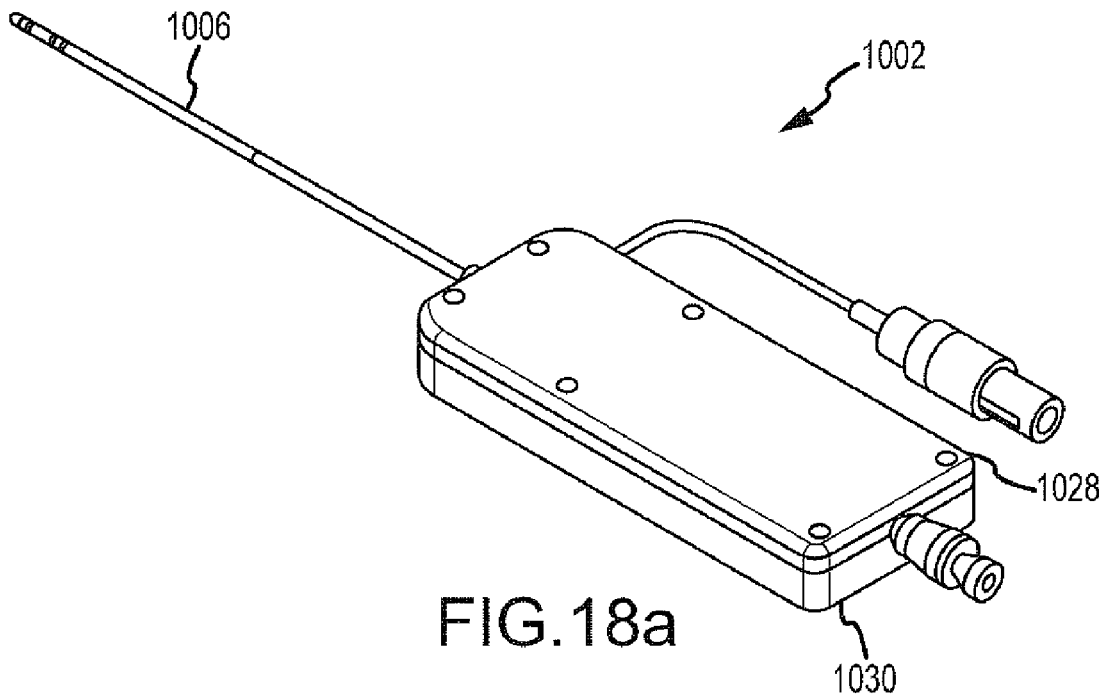
FIGS. 18a and 18b are enlarged isometric views.
Figure 18B:
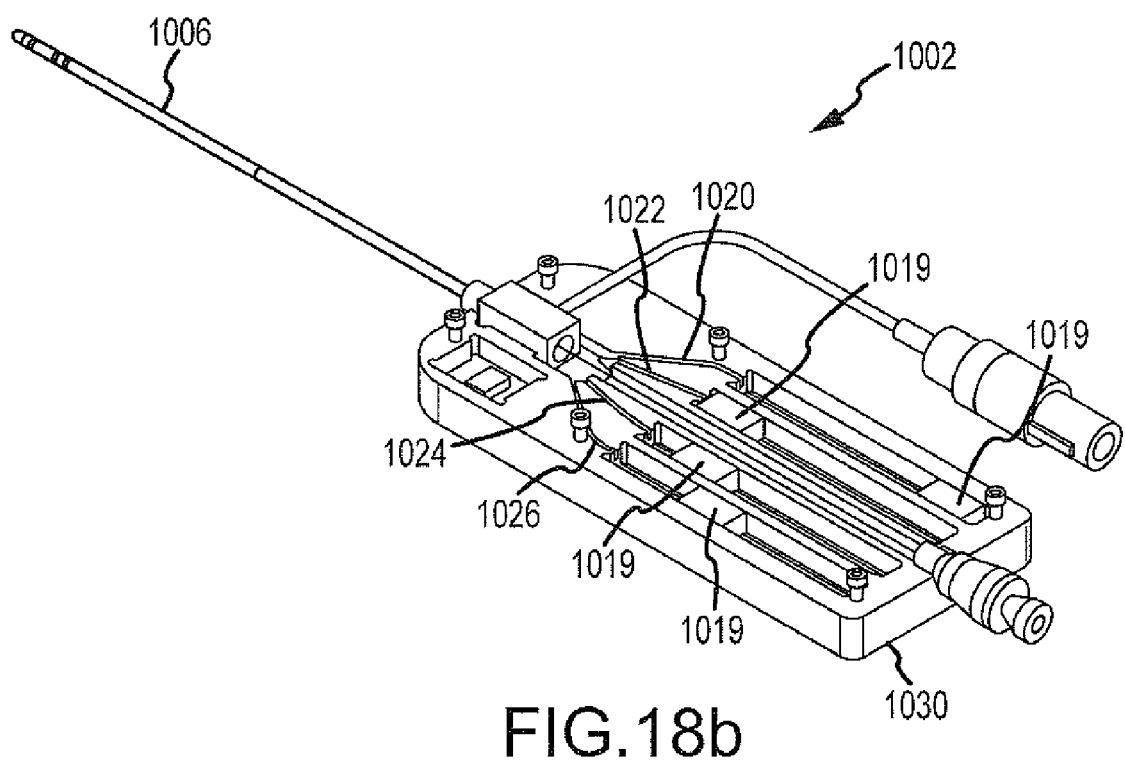
Figure 19A:
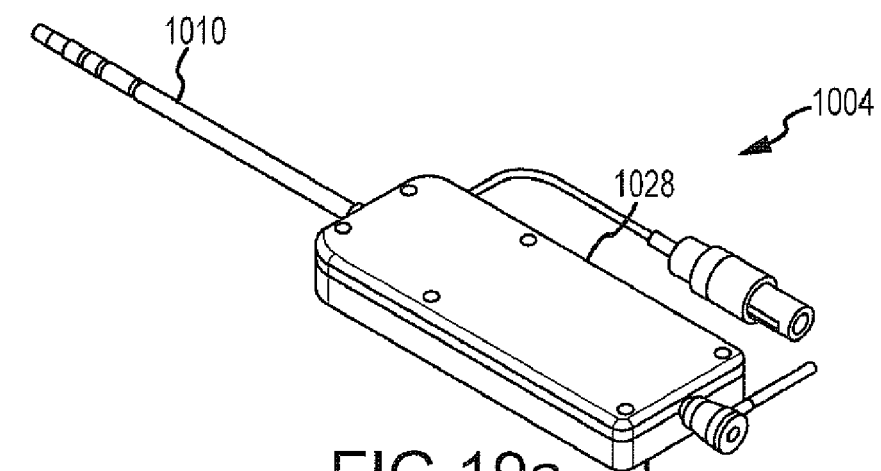
FIGS. 19a-19c are enlarged isometric views.
Figure 19B:
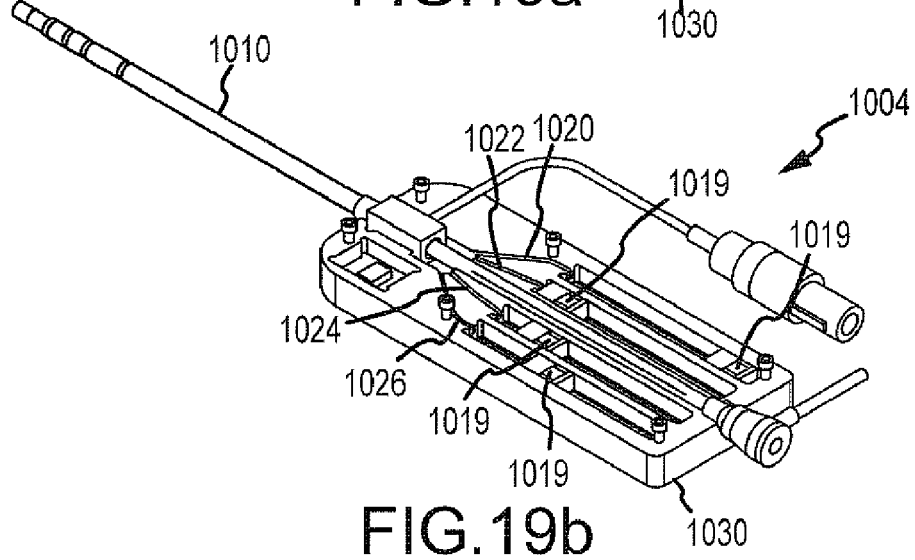
Figure 19C:
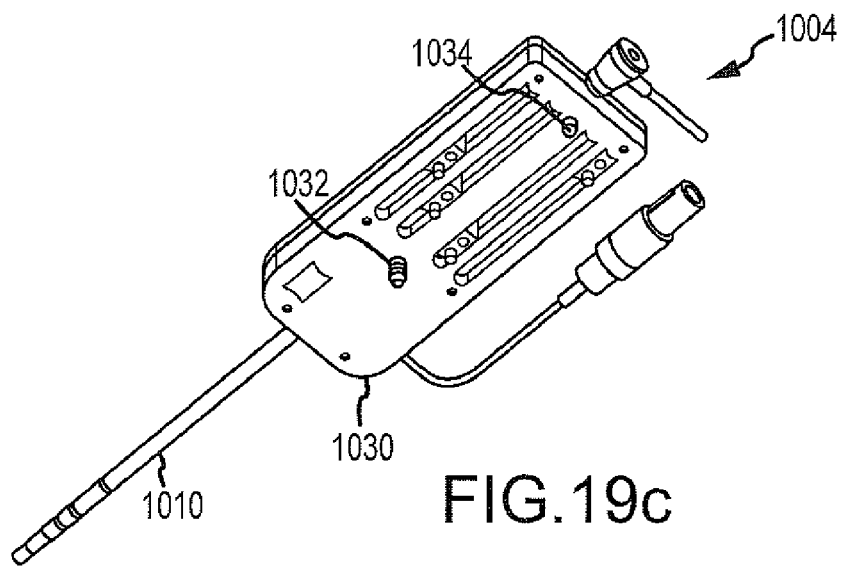
Figure 19D:
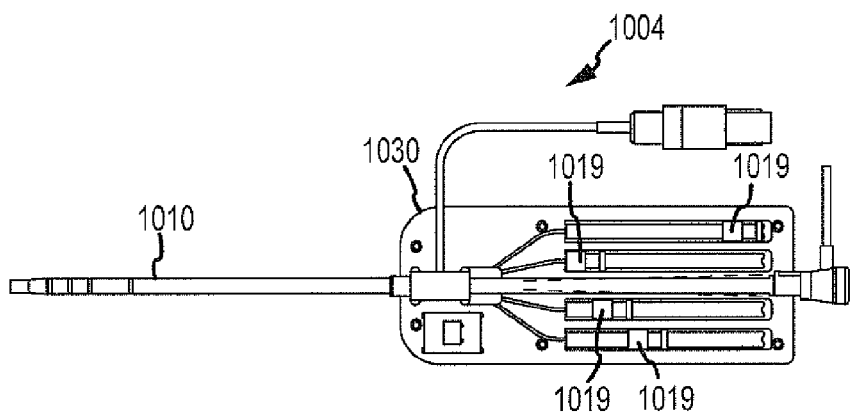
FIG. 19d-19i are respectively enlarged top, front, bottom, left side, and respectively sections A-A and B-B taken generally along lines A-A and B-B in FIG. 19f, views of a fourth embodiment of a robotic sheath device cartridge, with FIG. 16a illustrating an exemplary usage of the robotic sheath device cartridge.
Figure 19E:
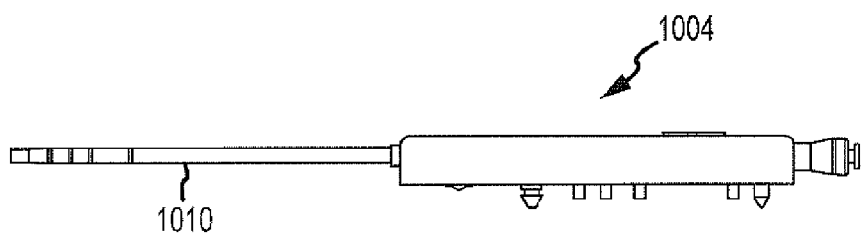
Figures 19F, 19G:
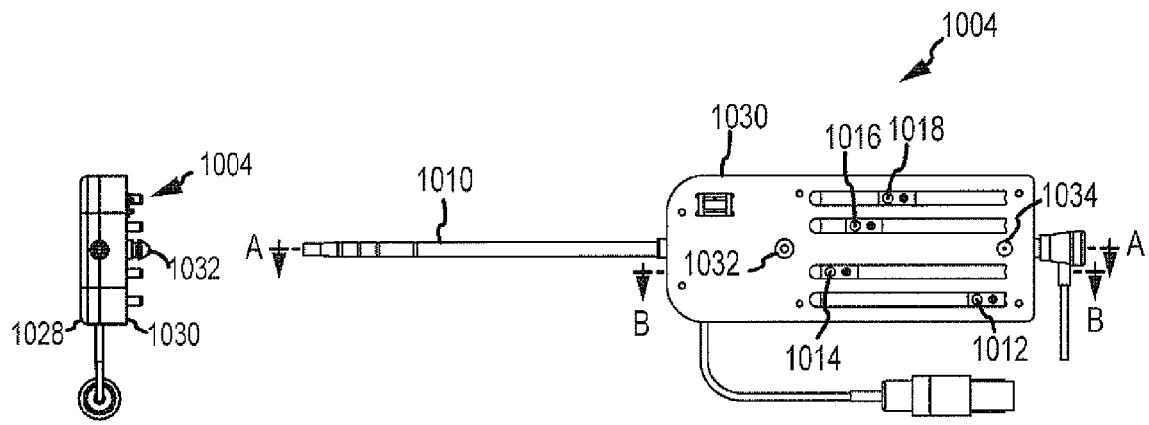
Figure 19H:
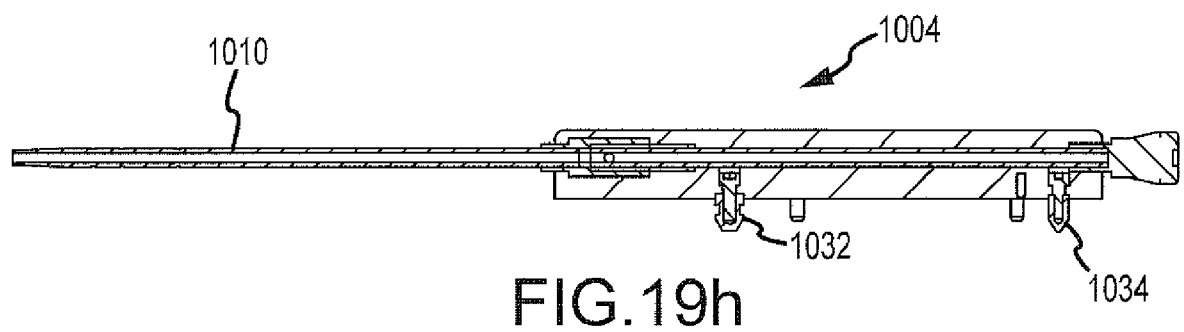
Figure 19I:
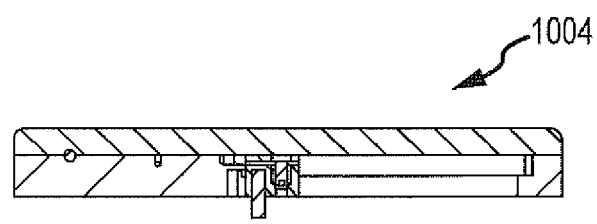

Each slider block may be designed to be actuated in a proximal direction to correspondingly push each respective finger. The finger can be configured to force the slider block to self center on its geometry when contact is first made. Such a centering feature may be facilitated by the contact surface of the slider block. For example, as shown in FIG. 17b, the slider block may include an engagement surface (e.g., shaped as a semi-cylindrical recess in the forward facing portion). This surface may be configured to mate or communicate with a matching round portion of a corresponding finger.

With sufficiently rigid coupling between each finger and a corresponding steering wire, pushing a finger in a proximal direction may cause an attached steering wire to tension and thus laterally deflect the distal end of catheter and sheath 1006, 1010. Moreover, in such an embodiment, because there is no rigid connection between each finger and its associated slider block, manipulator assembly 900 cannot pull the steering wire in a forward direction. That is, when each finger is actuated, it is only possible to tension the steering wire. Furthermore, because the push-actuation of each slider block occurs near that block's bottom surface, a moment may be imposed on the block. Because such moment may increase the likelihood of the block binding during travel, the length of the block may be optimized to reduce or minimize contact forces between the block and base plate 923.

The aforementioned electrical handshake between the manipulation bases and catheter and sheath cartridges will be described briefly.

As discussed above, robotic catheter system 10 may be useful for a variety of procedures and in connection with a variety of tools and/or catheters. Such tools and/or catheters may include, without limitation, spiral catheters, ablation catheters, mapping catheters, balloon catheters, needle/dilator tools, cutting tools, cauterizing tools, and/or gripping tools. The system may additionally include a means of identifying the nature and/or type of catheter/tool cartridge that is installed for use, and/or position or connection related information. The system may also automatically access/obtain additional information about the cartridge, such as, without limitation, its creation date, serial number, sterilization date, prior uses, etc.

Further, some embodiments of the system may include an ability to "read" or detect the type or nature of the connected cartridge through the use of memory included with the disposable cartridge together with some data/signal transmission means. By way of example, each cartridge may contain a chip (e.g., an EEPROM chip) that can be electrically interfaced by the manipulator head. Such a chip could, for instance, be programmed during the manufacturing process and may electronically store various data, such as the make; model; serial number; creation date; and/or other special features associated with the cartridge or tool. Additionally the chip may contain other worthwhile information, such as an indication of previous use, catheter specific calibration data, and/or any other information that may relate to the safety or performance of the particular device.

In an embodiment, upon interconnecting the cartridge (e.g. 400) with the manipulator head (e.g. 300), a detection means, such as an optical or magnetic sensor, may initially detect the presence of the cartridge. Once presence is detected, the manipulator may energize a chip and initiate data/signal retrieval. Such retrieved data/signal may then be used by the system to control or alter various features and/or displays based on the type of device and/or information provided. While one embodiment may use a chip (e.g., EEPROM), due to its design flexibility, another embodiment may include a wireless transmission device, such as an RFID, which may be employed to facilitate the data storage/transfer instead of, or in addition to a chip.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:

1. A robotic catheter manipulator assembly comprising:
    a support member having a longitudinal axis;
    a catheter manipulation base operably coupled to the support member;
    a sheath manipulation base operably coupled to the support member, each manipulation base configured to be linearly movable relative to the other manipulation base and to the support member along the longitudinal axis of the support member, the catheter manipulation base being releasably connectable to a catheter cartridge and the sheath manipulation base being releasably connectable to a sheath cartridge;
    wherein one of the catheter manipulation base and the catheter cartridge includes at least one finger engagable in a substantially linear motion with at least one complementary component in the other one of the catheter manipulation base and the catheter cartridge for controlling deflection of a catheter by pulling a steering wire attached to the catheter and one of the finger and the slider block; and
    at least one drive mechanism for moving the catheter and sheath manipulation bases relative to each other and to the support member.

2. The robotic catheter manipulator assembly according to claim 1, wherein the complementary component is a slider block.

3. The robotic catheter manipulator assembly according to claim 1, wherein the finger is movable by one of a motor driven lead screw, a ball screw, a belt drive, a rolling ring linear drive and a piezo motor drive.

4. The robotic catheter manipulator assembly according to claim 1, wherein one of the sheath manipulation base and the sheath cartridge includes at least one finger engageable with at least one complementary slider block in the other one of the sheath manipulation base and the sheath cartridge for controlling deflection of a sheath by pulling a steering wire attached to the sheath and one of the finger and the slider block.

5. The robotic catheter manipulator assembly according to claim 4, wherein the finger is movable by one of a motor driven lead screw, a ball screw, a belt drive, a rolling ring linear drive and a piezo motor drive.

6. The robotic catheter manipulator assembly according to claim 1, wherein one of the catheter manipulation base and the catheter cartridge includes at least one first element engageable with at least one complementary second element of the other one of the catheter manipulation base and the catheter cartridge for controlling deflection of a catheter by pulling a steering wire attached to the catheter and one of the first and second elements.

7. The robotic catheter manipulator assembly according to claim 1, wherein one of the sheath manipulation base and the sheath cartridge includes at least one first element engageable with at least one complementary second element of the other one of the sheath manipulation base and the sheath cartridge for controlling deflection of a sheath by pulling a steering wire attached to the sheath and one of the first and second elements.

8. The robotic catheter manipulator assembly according to claim 1, wherein the drive mechanism is one of a motor driven lead screw, a ball screw, a belt drive, a rolling ring linear drive and a piezo motor drive.

9. The robotic catheter manipulator assembly according to claim 1, further comprising at least one recess in one of the catheter manipulation base and the catheter cartridge for engagement with one of:
  at least one complementary locator detent on the other one of the catheter manipulation base and the catheter cartridge for alignment of the catheter cartridge relative to the catheter manipulation base, and
  at least one complementary locking detent on the other one of the catheter manipulation base and the catheter cartridge for releasable locking of the catheter cartridge with the catheter manipulation base.

10. The robotic catheter manipulator assembly according to claim 1, further comprising at least one recess in one of the sheath manipulation base and the sheath cartridge for engagement with one of:
  at least one complementary locator detent on the other one of the sheath manipulation base and the sheath cartridge for alignment of the sheath cartridge relative to the sheath manipulation base, and
  at least one complementary locking detent on the other one of the sheath manipulation base and the sheath cartridge for releasable locking of the sheath cartridge with the sheath manipulation base.

11. The robotic catheter manipulator assembly according to claim 1, further comprising means for at least one of aligning and releasably locking the catheter manipulation base with the catheter cartridge.

12. The robotic catheter manipulator assembly according to claim 1, further comprising means for at least one of aligning and releasably locking the sheath manipulation base with the sheath cartridge.

13. The robotic catheter manipulator assembly according to claim 1, wherein the catheter and sheath manipulation bases each include a release lever operable to release a respectively connected catheter and sheath cartridge.

14. The robotic catheter manipulator assembly according to claim 1, wherein the support member lies in a plane disposed at an acute angle relative to a generally horizontally disposed operation bed.

15. The robotic catheter manipulator assembly according to claim 1, wherein the support member lies in a plane disposed generally orthogonal to a generally horizontally disposed operation bed.

16. The robotic catheter manipulator assembly according to claim 1, wherein the catheter and sheath manipulation bases are movable in a plane disposed at an acute angle relative to a generally horizontally disposed operation bed.

17. The robotic catheter manipulator assembly according to claim 1, wherein the catheter and sheath manipulation bases are movable in a plane disposed generally orthogonal to a generally horizontally disposed operation bed.

18. The robotic catheter manipulator assembly according to claim 1, wherein the catheter manipulation base is disposed generally behind the sheath manipulation base to allow insertion of a catheter into a sheath respectively connected to the catheter and sheath cartridges.

19. A robotic manipulator assembly comprising:
  a support member having a longitudinal axis;
  a manipulation base operably coupled to the support member and releasably connectable to a cartridge, wherein the manipulation base is configured to be linearly movable along the longitudinal axis of the support member, and wherein one of the manipulation base and the cartridge includes at least one finger engageable in a linear motion with at least one complementary slider block of the other one of the manipulation base and the cartridge for controlling deflection of a component connected to the cartridge; and
  a drive mechanism for linearly moving at least one of the finger and the slider block along the longitudinal axis of the support member.

20. The robotic manipulator assembly according to claim 19, wherein the cartridge is one of a transseptal cartridge, a catheter cartridge and a sheath cartridge, and the component is respectively one of a transseptal needle, a catheter and a sheath.

21. The robotic manipulator assembly according to claim 19, wherein the drive mechanism is one of a motor driven lead screw, a ball screw, a belt drive, a rolling ring linear drive and a piezo motor drive.

22. The robotic manipulator assembly according to claim 19, wherein the manipulation base is movable by one of a motor driven lead screw, a ball screw, a belt drive, a rolling ring linear drive and a piezo motor drive.

23. The robotic manipulator assembly according to claim 19, further comprising at least one recess in one of the manipulation base and the cartridge for engagement with one of:
  at least one complementary locator detent on the other one of the manipulation base and the cartridge for alignment of the cartridge relative to the manipulation base, and
  at least one complementary locking detent on the other one of the manipulation base and the cartridge for releasable locking of the cartridge with the manipulation base.

24. The robotic manipulator assembly according to claim 19, further comprising means for aligning and releasably locking the manipulation base with the cartridge.

25. The robotic manipulator assembly according to claim 19, wherein the manipulation base includes a release lever operable to release a connected cartridge.

26. The robotic manipulator assembly according to claim 19, wherein the support member lies in a plane disposed at an acute angle relative to a generally horizontally disposed operation bed.

27. The robotic manipulator assembly according to claim 19, wherein the support member lies in a plane disposed generally orthogonal to a generally horizontally disposed operation bed.

28. The robotic manipulator assembly according to claim 19, wherein the manipulation base is movable in a plane disposed at an acute angle relative to a generally horizontally disposed operation bed.

29. The robotic manipulator assembly according to claim 19, wherein the manipulation base is movable in a plane disposed generally orthogonal to a generally horizontally disposed operation bed.

30. A robotic manipulator assembly comprising:
  a support member having a longitudinal axis,
  a manipulation base operably coupled to the support member and releasably connectable to a cartridge, wherein the manipulation base is configured to be linearly movable along the longitudinal axis of the support member, and wherein one of the manipulation base and the cartridge includes at least one first element engageable in a linear motion with at least one complementary second element of the other one of the manipulation base and the cartridge for controlling deflection of a component connected to the cartridge; and
  a drive mechanism for linearly moving at least one of the first and second elements along the longitudinal axis of the support member.

31. The robotic manipulator assembly according to claim 30, wherein the cartridge is one of a transseptal cartridge, a catheter cartridge and a sheath cartridge, and the component is respectively one of a transseptal needle, a catheter and a sheath.

32. The robotic manipulator assembly according to claim 30, wherein the component is a surgically insertable device.

33. The robotic manipulator assembly according to claim 30, wherein the drive mechanism is one of a motor driven lead screw, a ball screw, a belt drive, a rolling ring linear drive and a piezo motor drive.

34. The robotic manipulator assembly according to claim 30, wherein manipulation base is movable by one of a motor driven lead screw, a ball screw, a belt drive, a rolling ring linear drive and a piezo motor drive.

35. The robotic manipulator assembly according to claim 30, further comprising at least one recess in one of the manipulation base and the cartridge for engagement with at least one complementary locator detent on the other one of the manipulation base and the cartridge for alignment of the cartridge relative to the manipulation base.

36. The robotic manipulator assembly according to claim 30, further comprising at least one recess in one of the manipulation base and the cartridge for engagement with at least one complementary locking detent on the other one of the manipulation base and the cartridge for releasable locking of the cartridge with the manipulation base.

37. The robotic manipulator assembly according to claim 30, further comprising means for aligning and releasably locking the manipulation base with the cartridge.

38. The robotic manipulator assembly according to claim 30, wherein the manipulation base includes a release lever operable to release a connected cartridge.

39. The robotic manipulator assembly according to claim 30, wherein the support member lies in a plane disposed at an acute angle relative to a generally horizontally disposed operation bed.

40. The robotic manipulator assembly according to claim 30, wherein the support member lies in a plane disposed generally orthogonal to a generally horizontally disposed operation bed.

41. The robotic manipulator assembly according to claim 30, wherein the manipulation base is movable in a plane disposed at an acute angle relative to a generally horizontally disposed operation bed.

42. The robotic manipulator assembly according to claim 30, wherein the manipulation base is movable in a plane disposed generally orthogonal to a generally horizontally disposed operation bed.

43. The robotic manipulator assembly according to claim 30, wherein one of the first and second elements is a finger and the other of the first and second elements is a pin.

44. The robotic manipulator assembly according to claim 30, wherein one of the first and second elements is a finger and the other of the first and second elements is a slider block.

45. The robotic manipulator assembly according to claim 30, further comprising integrated force sensors operatively connected to the cartridge for permitting active tensioning of steering wires for controlling deflection of the component connected to the cartridge.

46. The robotic manipulator assembly according to claim 30, further comprising integrated force sensors operatively connected to the cartridge for limiting stress on the component by limiting movement of the cartridge.

\* \* \* \* \*